United States Patent
Fraunhofer et al.

(10) Patent No.: US 8,753,839 B2
(45) Date of Patent: Jun. 17, 2014

(54) COMPOSITIONS AND METHODS FOR CRYSTALLIZING ANTIBODIES

(75) Inventors: Wolfgang Fraunhofer, Newton, MA (US); David W. Borhani, Hartsdale, NY (US); Gerhard Winter, Penzberg (DE); Stefan Gottschalk, Grunwald (DE)

(73) Assignee: Abbvie Inc., North Chicago, IL (US)

( * ) Notice: Subject to any disclaimer, the term of this patent is extended or adjusted under 35 U.S.C. 154(b) by 715 days.

(21) Appl. No.: 12/228,038

(22) Filed: Aug. 8, 2008

(65) Prior Publication Data
US 2009/0148513 A1    Jun. 11, 2009

Related U.S. Application Data

(60) Provisional application No. 60/963,964, filed on Aug. 8, 2007.

(51) Int. Cl.
| | |
|---|---|
| *C12P 21/06* | (2006.01) |
| *A61K 39/395* | (2006.01) |
| *A01N 61/00* | (2006.01) |
| *C07K 16/24* | (2006.01) |
| *A61K 39/00* | (2006.01) |

(52) U.S. Cl.
CPC ......... *C07K 16/241* (2013.01); *A61K 2039/505* (2013.01); *C07K 2299/00* (2013.01); *C07K 2316/96* (2013.01)
USPC ............................. 435/69.1; 424/130.1; 514/1

(58) Field of Classification Search
None
See application file for complete search history.

(56) References Cited

U.S. PATENT DOCUMENTS

| | | | |
|---|---|---|---|
| 5,231,024 | A | 7/1993 | Moeller et al. |
| 5,656,272 | A | 8/1997 | Le |
| 6,090,382 | A | 7/2000 | Salfeld et al. |
| 6,258,562 | B1 | 7/2001 | Salfeld et al. |
| 6,448,380 | B2 | 9/2002 | Rathjen |
| 6,451,983 | B2 | 9/2002 | Rathjen |
| 6,498,237 | B2 | 12/2002 | Rathjen |
| 6,509,015 | B1 | 1/2003 | Salfeld et al. |
| 7,070,775 | B2 | 7/2006 | Le |
| 7,192,584 | B2 | 3/2007 | Le |
| 7,223,394 | B2 | 5/2007 | Salfeld et al. |
| 7,250,165 | B2 | 7/2007 | Heavner |
| 7,276,239 | B2 | 10/2007 | Le |

(Continued)

FOREIGN PATENT DOCUMENTS

| | | |
|---|---|---|
| EP | 0260610 B1 | 9/1993 |
| WO | WO 97/29131 | 8/1997 |

(Continued)

OTHER PUBLICATIONS

Weber, Overview of Crystallization Methods. Methods in Enzymology, 1997, vol. 276, pp. 13-22.*

(Continued)

*Primary Examiner* — Alexander Kim
(74) *Attorney, Agent, or Firm* — McCarter & English, LLP; Cristin H. Cowles; Soo-Hwa Kim

(57) ABSTRACT

The present invention relates to a batch crystallization method for crystallizing anti-human TNFalpha (hTNFalpha) antibody and antibody fragments which allows the production of said antibody on an industrial scale; a method of controlling the size of antibody crystals, for example, crystals of anti-hTNFalpha antibody fragments, compositions containing said crystals as well as methods of use of said crystals and compositions.

57 Claims, 6 Drawing Sheets

Yield of MAK195F crystals at different rpm

(56) References Cited

U.S. PATENT DOCUMENTS

| | | |
|---|---|---|
| 7,541,031 B2 | 6/2009 | Salfeld et al. |
| 7,588,761 B2 | 9/2009 | Salfeld et al. |
| 7,863,426 B2 | 1/2011 | Wan et al. |
| 7,919,264 B2 | 4/2011 | Maksymowych et al. |
| 7,960,516 B2 | 6/2011 | Matheus et al. |
| 8,034,906 B2 | 10/2011 | Borhani et al. |
| 8,168,760 B2 | 5/2012 | Borhani et al. |
| 8,206,714 B2 | 6/2012 | Salfeld et al. |
| 8,372,401 B2 | 2/2013 | Salfeld et al. |
| 8,414,894 B2 | 4/2013 | Salfeld et al. |
| 8,436,149 B2 | 5/2013 | Borhani et al. |
| 2002/0136719 A1 | 9/2002 | Shenoy et al. |
| 2003/0012786 A1 | 1/2003 | Teoh et al. |
| 2003/0049725 A1 | 3/2003 | Heavner |
| 2003/0161828 A1 | 8/2003 | Abdelghany et al. |
| 2003/0206898 A1 | 11/2003 | Fischkoff et al. |
| 2003/0219438 A1 | 11/2003 | Salfeld et al. |
| 2003/0235585 A1 | 12/2003 | Fischkoff et al. |
| 2004/0009172 A1 | 1/2004 | Fischkoff et al. |
| 2004/0033228 A1 | 2/2004 | Krause et al. |
| 2004/0120952 A1 | 6/2004 | Knight |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0166111 A1 | 8/2004 | Kaymakcalan et al. |
| 2004/0219142 A1 | 11/2004 | Banerjee et al. |
| 2005/0019794 A1 | 1/2005 | Nassef et al. |
| 2005/0123541 A1 | 6/2005 | Heavner |
| 2005/0147610 A1 | 7/2005 | Ghayur et al. |
| 2005/0249735 A1 | 11/2005 | Le |
| 2006/0009385 A1 | 1/2006 | Hoffman et al. |
| 2006/0018907 A1 | 1/2006 | Le |
| 2006/0083741 A1 | 4/2006 | Hoffman et al. |
| 2006/0153846 A1 | 7/2006 | Krause et al. |
| 2006/0246073 A1 | 11/2006 | Knight |
| 2007/0003548 A1 | 1/2007 | Heavner |
| 2007/0041905 A1 | 2/2007 | Hoffman et al. |
| 2007/0071747 A1 | 3/2007 | Hoffman et al. |
| 2007/0081996 A1 | 4/2007 | Hoffman et al. |
| 2007/0172897 A1 | 7/2007 | Maksymowych et al. |
| 2007/0196373 A1 | 8/2007 | Le |
| 2007/0202104 A1 | 8/2007 | Banerjee et al. |
| 2007/0298040 A1 | 12/2007 | Le |
| 2008/0025976 A1 | 1/2008 | Le |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0227136 A1 | 9/2008 | Pla et al. |
| 2008/0292642 A1 | 11/2008 | Borhani et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0068172 A1 | 3/2009 | Kaymakcalan et al. |
| 2009/0110679 A1 | 4/2009 | Li et al. |
| 2009/0123378 A1 | 5/2009 | Wong et al. |
| 2009/0148513 A1 | 6/2009 | Fraunhofer et al. |
| 2009/0155205 A1 | 6/2009 | Salfeld et al. |
| 2009/0202557 A1 | 8/2009 | Argiriadi et al. |
| 2009/0226530 A1 | 9/2009 | Lassner et al. |
| 2009/0239259 A1 | 9/2009 | Hsieh et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong et al. |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0160894 A1 | 6/2010 | Julian et al. |
| 2010/0278822 A1 | 11/2010 | Fraunhofer et al. |
| 2011/0002935 A1 | 1/2011 | Wan et al. |
| 2011/0054414 A1 | 3/2011 | Shang et al. |
| 2011/0171227 A1 | 7/2011 | Okun et al. |
| 2011/0300151 A1 | 12/2011 | Okun et al. |
| 2012/0014956 A1 | 1/2012 | Kupper et al. |
| 2012/0039900 A1 | 2/2012 | Stuhlmuller et al. |
| 2012/0077213 A1 | 3/2012 | Pla et al. |
| 2012/0107783 A1 | 5/2012 | Julian et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0258114 A1 | 10/2012 | Salfeld et al. |
| 2012/0282262 A1 | 11/2012 | Okun et al. |
| 2012/0282270 A1 | 11/2012 | Krause et al. |
| 2013/0004507 A1 | 1/2013 | Fischkoff et al. |
| 2013/0028903 A1 | 1/2013 | Wan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0243786 A1 | 9/2013 | Banerjee et al. |

FOREIGN PATENT DOCUMENTS

| | | |
|---|---|---|
| WO | WO 02/12502 | 2/2002 |
| WO | WO 02/072636 A2 | 9/2002 |
| WO | WO 2004/009776 A2 | 1/2004 |
| WO | WO 2005/121177 A2 | 12/2005 |
| WO | WO 2006/012500 A2 | 2/2006 |
| WO | WO 2006/069036 A2 | 6/2006 |
| WO | WO 2008/121301 A1 | 10/2008 |
| WO | WO 2009/020654 A1 | 2/2009 |

OTHER PUBLICATIONS

Drenth, "Principles of Protein X-Ray Crystallography", 2nd Edition, 1999, Springer-Verlag New York Inc., pp. 1-21.*

Klyushnichenko, Protein crystallization: From HTS to kilogram-scale, Curr. Op. Drug Discovery, 2003, vol. 6(6), pp. 848-854.*

Yang et al., Crystalline monoclonal antibodies for subcutaneous delivery, PNAS Jun. 10, 2003, vol. 100, pp. 6934-6939.*

Scheinfeld, 2004, Journal of Drugs in Dermatology, Off-label uses and side effects of infliximab.*

Ahamed et al. "Phase Behaviour of Intact Monoclonal Antibody," Biochemical Journal, Jul. 2007, vol. 93, pp. 610-619.

Baldock, "A comparison of microbatch and vapour diffusion for initial screening of crystallization conditions," *Journal of Crystal Growth*, Oct. 1996, vol. 168, No. 1-4, pp. 170-174.

Benevenuti et al., "Crystallization of Soluble Proteins in Vapor Diffusion for X-ray Crystallography," Nature Protocols, published online Jun. 28, 2007, 2(7):1633-1651.

Connell, G. E., et al., "A Human IgG Myeloma Protein Crystallizing with Rhombohedral Symmetry," Can. J. Biochem., 1973, vol. 51, pp. 1137-1141.

Cudney R., "Protein Crystallization and Dumb Luck," The Rigaku Journal, 1999, vol. 16, No. 1, pp. 1-7.

Data Sheet: Drum Rollers—Portable Drum Rotators Drum Mixers, URL<:http://web.archive.org/web/20070117013405/http://www.morsemfgeo.com/products/201-Portable-Drum-Roller.htm>., Jan. 2007 [retrieved on Dec. 2, 2008].

Data Sheet: Fisher Scientific. Hematology/Chemistry Mixer Fisher Scientific, http://www.fishersci.com/, 2008 [Retrieved on Dec. 2, 2008].

Drenth, "Principles of Protein X-Ray Crystallography", 2nd Edition, 1999, Springer-Verlag New York Inc., Chapter 1, p. 1-21.

Harris, L. J., et al., "The Three-dimensional Structure of an Intact Monoclonal Antibody for Canine Lymphoma," Nature, 1992, vol. 360, pp. 369-372.

Huber, R., et al., "Crystallographic Structure Studies of an IgG Molecule and an Fc Fragment," Nature, 1976, vol. 264, pp. 415-420.

(56) References Cited

OTHER PUBLICATIONS

International Preliminary Report on Patentability for Application No. PCT/US08/04006, dated Aug. 28, 2009.
International Search Report for Application No. PCT/US09/000568, dated May 13, 2009.
International Search Report for Application No. PCT/US08/009549, dated Dec. 17, 2008.
International Search Report and Written Opinion for Application No. PCT/US08/04006, dated Jul. 2, 2008.
International Search Report for Application No. PCT/US07/022622, dated Sep. 4, 2008.
Jen et al., "Diamonds in the Rough: Protein Crytsals from a Formulation Perspective," *Pharmaceutical Research*, 2001, vol. 18, No. 11, pp. 1483-1488.
Jentoft, J. E., et al., "Characterization of a Human Cryoglobulin Complex: A Crystalline Adduct of a Monoclonal Immunoglobulin G and Albumin," Biocehmistry, 1982, vol. 21, pp. 289-294.
Jones, H. B., "On a New Substance Occurring in the Urine of a Patient with Mollities Ossium," Phil. Tr. Royal Soc. London, 1848, vol. 138, pp. 55-62.
Kundrot, C.E., "Which Strategy for a Protein Crystallization Project?" Cellular Molecular Life Science, 2004, vol., 61, pp. 525-536.
McPherson, "A comparison of salts for the crystallization of macromolecules," *Protein Science*, 2001, vol. 10, pp. 418-422.
McPherson, A., "Current Approaches to Macromolecular Crystallization" European Journal of Biochemistry, 1990, vol. 189, pp. 1-23.
Mills, L. E., et al., "Crystallocryoglobulinemia Resulting from Human Monoclonal Antibodies to Albumin," Annals of Internal Medicine, 1983, vol. 99, pp. 601-604.
Nisonoff, A., et al. "Properties of Crystallized Rabbit Anti-p-Azobenzoate Antibody," Cold Spring Harb. Symp. Quant. Biol., 1967, vol. 32, pp. 89-93.
Putnam, F. W., "Abnormal Human Serum Globulins," 1955, Science, vol. 122, pp. 275-277.
Rajan, S. S., et al., "Three-Dimensional Structure of the Mcg IgG1 Immunoglobulin," 1983, Molecular Immunology, vol. 20, pp. 787-799.
Sarma, V. R., et al., "The Three-Dimensional Structure at 6 A Resolution of a Human γG1 Immunoglobulin Molecule," The Journal of Biological Chemistry, 1971, vol. 246, pp. 3753-3759.
Terry, W. D., et al., "Crystallographic Studies of a Human Immunoglobulin," Nature, 1968, vol. 220, pp. 239-241.
Von Bonsdorff, B., et al., "On the Presence of a High-molecular Crystallizable Protein in Blood Serum in Myeloma," Folia Haemat., 1938, vol. 59:, p. 184-208.
Weber, P.C., "Overview of Crystallization Methods," Methods in Enzymology, 1997, vol. 276, pp. 13-22.
Yang et al., "Crystalline Monoclonal Antibodies for Subcutaneous Delivery," *Proceedings of the National Academy of Sciences* Jun. 10, 2003. vol. 100, No. 12, pp. 6934-6939.
Klyushnichenko, V., "Protein Crystallization: From HTS to Kilogram Scale," *Curr. Opin. In Drug Discovery & Development*, 6(6): 848-854, 2003.
English Abstract of European Patent No. EP 0350690.
Supplementary European Search Report for EP 08795162.

\* cited by examiner

A: MAK195F crystals, 10 rpm

B: MAK195F crystals, 20 rpm

C: MAK195F crystals, 40 rpm

D: MAK195F crystals, 60 rpm

E: MAK195F crystals, 80 rpm

```
                              SEQUENCE LISTING

<160> NUMBER OF SEQ ID NOS: 9

<210> SEQ ID NO 1
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Val Met Thr Gln Ser His Lys Phe Met Ser Thr Thr Val Gly
1               5                   10                  15

Asp Arg Val Ser Ile Thr Cys Lys Ala Ser Gln Ala Val Ser Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Val Thr Asp Phe Thr Leu Thr Ile His Asn Leu Gln Ala
65                  70                  75                  80

Glu Asp Leu Ala Leu Tyr Tyr Cys Gln Gln His Tyr Ser Thr Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 2
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Asn Trp Val Arg Gln Pro Pro Gly Lys Gly Leu Glu Trp Leu
```

```
             35                  40                  45
Gly Met Ile Trp Gly Asp Gly Ser Thr Asp Tyr Asp Ser Thr Leu Lys
 50                  55                  60

Ser Arg Leu Ser Ile Ser Lys Asp Asn Ser Lys Ser Gln Ile Phe Leu
 65                  70                  75                  80

Lys Met Asn Ser Leu Gln Thr Asp Asp Thr Ala Arg Tyr Tyr Cys Ala
                 85                  90                  95

Arg Glu Trp His His Gly Pro Val Ala Tyr Trp Gly Gln Gly Thr Leu
            100                 105                 110

Val Thr Val Ser Ala Ala Thr Thr Ala Pro Ser Val Tyr Pro Leu
        115                 120                 125

Val Pro Gly Cys Ser Asp Thr Ser Gly Ser Ser Val Thr Leu Gly Cys
        130                 135                 140

Leu Val Lys Gly Tyr Phe Pro Glu Pro Val Thr Val Lys Trp Asn Tyr
145                 150                 155                 160

Gly Ala Leu Ser Ser Gly Val Arg Thr Val Ser Ser Val Leu Gln Ser
                165                 170                 175

Gly Phe Tyr Ser Leu Ser Ser Leu Val Thr Val Pro Ser Ser Thr Trp
            180                 185                 190

Pro Ser Gln Thr Val Ile Cys Asn Val Ala His Pro Ala Ser Lys Thr
        195                 200                 205

Glu Leu Ile Lys Arg Ile Glu Pro Arg Ile Pro Lys Pro Ser Thr Pro
        210                 215                 220

Pro Gly Ser Ser Cys Pro Pro Gly Asn Ile Leu Gly Gly Pro Ser Val
225                 230                 235                 240

Phe Ile Phe Pro Pro Lys Pro Lys Asp Ala Leu Met Ile Ser Leu Thr
                245                 250                 255

Pro Lys Val Thr Cys Val Val Val Asp Val Ser Glu Asp Asp Pro Asp
            260                 265                 270

Val His Val Ser Trp Phe Val Asp Asn Lys Glu Val His Thr Ala Trp
        275                 280                 285

Thr Gln Pro Arg Glu Ala Gln Tyr Asn Ser Thr Phe Arg Val Val Ser
    290                 295                 300

Ala Leu Pro Ile Gln His Gln Asp Trp Met Arg Gly Lys Glu Phe Lys
305                 310                 315                 320

Cys Lys Val Asn Asn Lys Ala Leu Pro Ala Pro Ile Glu Arg Thr Ile
                325                 330                 335

Ser Lys Pro Lys Gly Arg Ala Gln Thr Pro Gln Val Tyr Thr Ile Pro
            340                 345                 350

Pro Pro Arg Glu Gln Met Ser Lys Lys Val Ser Leu Thr Cys Leu
        355                 360                 365

Val Thr Asn Phe Phe Ser Glu Ala Ile Ser Val Glu Trp Glu Arg Asn
    370                 375                 380

Gly Glu Leu Glu Gln Asp Tyr Lys Asn Thr Pro Pro Ile Leu Asp Ser
385                 390                 395                 400

Asp Gly Thr Tyr Phe Leu Tyr Ser Lys Leu Thr Val Asp Thr Asp Ser
                405                 410                 415

Trp Leu Gln Gly Glu Ile Phe Thr Cys Ser Val Val His Glu Ala Leu
            420                 425                 430

His Asn His His Thr Gln Lys Asn Leu Ser Arg Ser Pro Gly Lys
        435                 440                 445

<210> SEQ ID NO 3
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Pro Gly Asn
1

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Pro Gly Asn Ile Leu
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Pro Gly Asn Ile Leu Gly
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Ile Leu Gly Gly Pro Ser
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Ile Leu Gly Gly Pro Ser Val
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Ile Leu Gly Gly Pro Ser Val Phe
1               5
```

```
<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Ile Leu Gly
1
```

COMPOSITIONS AND METHODS FOR CRYSTALLIZING ANTIBODIES

CROSS REFERENCE TO RELATED APPLICATION

This application is a continuation-in-part and claims priority to U.S. Provisional Application Ser. No. 60/963,964 filed on Aug. 8, 2007, which is incorporated herein in its entirety.

FIELD OF THE INVENTION

The present invention relates to compositions and methods for crystallizing antibodies, including antibody fragments, and uses thereof. In an embodiment, the invention relates to methods of crystallizing antibody fragments, such as anti-human tumor necrosis factor alpha (hTNFalpha) antibody fragments, on an industrial scale, as well as methods of controlling the size of the antibody and antibody fragment crystals.

BACKGROUND OF THE INVENTION

With over 100 monoclonal antibodies currently being evaluated in clinical study phases 2 or 3, the monoclonal antibody (mAb) market is considered one of the most promising biopharmaceutical markets. Since these drugs have to be delivered to patients in single doses that often exceed 100 mg, there is an urgent need to find suitable formulations that satisfy stability and safety requirements, as well as patient compliance.

Highly concentrated liquid mAb formulations have a higher viscosity than less concentrated formulations, which can hinder their syringeability through more patient-friendly high gauge needles. Furthermore, the tendency of mAb molecules to aggregate exponentially increases with increased concentration, preventing compliance with safety and stability requirements. The delivery of high mAb doses therefore is restricted to large volumes, which generally have to be delivered via infusion. However, this mode of dosing is cost intensive and significantly reduces patient compliance.

For this reason, mAbs in a crystal form are desirable for use as drug substance. However few attempts have been made to evaluate this strategy due to the well known unpredictability associated with crystallization conditions. Although the protein insulin has been successfully crystallized, most other proteins tend to form unordered precipitates rather than crystals. Determining the crystallization conditions for a particular protein is therefore a non-trivial task. To date, there is no general rule that allows one to reliably predict a successful crystallization condition for a protein of choice.

Several screening systems are commercially available (for example, Hampton 1 and 2 and Wizard I and II) that allow, on a microliter scale, screening for potentially suitable crystallization conditions for a specific protein. However, positive results obtained using such screening systems do not necessarily translate into successful crystallization on a larger, industrially applicable batch scale (see Jen, A. et al. (2001) Pharm. Res. 18 (11):1483).

Baldock et al. ((1996) J. Crystal Growth, 168(1-4):170-174) reported on a comparison of microbatch and vapor diffusion for initial screening of crystallization conditions. Six commercially available proteins were screened using a set of crystallization solutions. The screens were performed using a common vapor diffusion method and three variants of a microbatch crystallization method. Out of 58 crystallization conditions identified, 43 (74%) were identified by microbatch, whereas 41 (71%) were identified by vapor diffusion. Twenty-six conditions were identified by both methods, and 17 (29%) would have been missed if microbatch had not been used at all. These data show that the vapor diffusion technique, which is most commonly used in initial crystallization screens, does not guarantee positive results.

Thus, the crystallization of diverse proteins cannot be carried out successfully using defined methods or algorithms. Certainly, there have been technical advances in the last 20-30 years. For example, A. McPherson provides extensive details on tactics, strategies, reagents, and devices for the crystallization of macromolecules. He does not, however, provide a method to ensure that any given macromolecule can indeed be crystallized by a skilled person with a reasonable expectation of success. McPherson states for example: "Whatever the procedure, no effort must be spared in refining and optimizing the parameters of the system, both solvent and solute, to encourage and promote specific bonding interactions between molecules and to stabilize them once they have formed. This latter aspect of the problem generally depends on the specific chemical and physical properties of the particular protein or nucleic acid being crystallized." (McPherson, A. (1999) *Crystallization of Biological Macromolecules*. Cold Spring Harbor, N.Y., Cold Spring Harbor Laboratory Press, p. 159). It is widely accepted by those skilled in the art of protein crystallization that no one algorithm is reliable for taking a new protein of interest, apply specific process steps, and thereby obtain the desired crystals.

Antibodies are particularly difficult to crystallize, due to the flexibility of the molecule. However, examples of immunoglobulin crystals do exist, such as Bence Jones proteins, which are crystals of an abnormal Ig light chain dimer (Jones, H. B. (1848). *Philosophical Transactions of the Royal Society, London,* 138:55-62). In addition, crystals of Ig heavy chain oligomer (von Bonsdorf, B., H. Groth, et al. (1938). *Folia Haematologia* 59:184-208) and human immunoglobulins of normal structure (two heavy chains linked to two light chains) have also been described (Putnam, F. W. (1955) *Science* 122:275-7; Terry, W. D., et al. (1968) *Nature* 220(164): 239-41; Huber, R., et al. (1976). *Nature* 264(5585):415-20; Rajan, S. S., et al. (1983) *Mol. Immunol.* 20(7):787-99; Harris, L. J., et al. (1992) *Nature*) 360(6402): 369-72, Nisonoff, A., et al. (1968) *Cold Spring Harbor Symposia on Quant. Biol.* 32:89-93; Connell, G. E., et al. (1973) *Canad. J. Biochem.* 51(8):1137-41; Mills, L. E., et al. (1983) *Annals of Int. Med.* 99(5):601-4; and Jentoft, J. E., et al. (1982) *Biochem.* 21(2):289-294. For example, Margolin and co-workers reported that the therapeutic monoclonal antibody trastuzumab (Herceptin®) could be crystallized (Shenoy, Govardhan et al. 2002) and that crystalline trastuzumab suspensions were therapeutically efficacious in a mouse tumor model, thus demonstrating retention of biological activity by crystalline trastuzumab (Yang, M. X., et al. (2003) *Proc. Natl. Acad. Sci.* 100(12):6934-6939). However, a predictable and reliable method of forming homogeneous antibody crystal preparations has not been described.

WO-A-02/072636 discloses the crystallization of the whole, intact antibodies Rituximab, Infliximab and Trastuzumab. Most of the crystallization experiments were performed with chemicals that have unclear toxicity, such as imidazole, 2-cyclohexyl-ethanesulfonate (CHES), methylpentanediol, copper sulphate, and 2-morpholino-ethanesulfonate (MES). Many of the examples in this application used seed crystals to initiate crystallization.

Human TNFalpha (hTNFalpha) is considered a causative agent of numerous diseases. There is, therefore, a great need for suitable methods of treating hTNFalpha related disorders.

One promising therapeutic approach is the administration of pharmaceutically effective doses of anti-human TNFalpha antibodies. Recently one such antibody, designated D2E7, or generically Adalimumab™, is now on the market under the trade name HUMIRA® (Abbott Laboratories).

WO-A-2004/009776 discloses crystallization experiments on a microliter scale using a sitting drop vapor diffusion technique, which involves mixing equal minute volumes (1 μl) of different crystallization buffers and D2E7 F(ab)'$_2$ or Fab fragments. No methods for the size-controlled crystallization of D2E7 antibody or its fragments were disclosed.

EP-A-0 260 610 discloses the series of murine anti-hTNFalpha monoclonal antibodies, i.e., the neutralizing antibody AM-195, also designated MAK195, as produced by a hybridoma cell line, deposited as ECACC 87050801 with the European Collection of Animal Cell Cultures (ECACC), Health Protection Agency Cultures Collection, Porton Down, Salisbury, United Kingdom on May 8, 1987. An F(ab')$_2$ fragment of MAK195 (e.g., MAK195F) is also known under the name Afelimomab™. Crystals of MAK195 and of MAK195F are not disclosed. Batch crystallization of these antibodies so far has not been successful.

At present, there is no technical teaching available that provides for the production of anti-hTNFalpha antibody fragment crystals. Moreover, no teaching is available that would provide the size-controlled crystallization of antibody molecules, including antibody fragments, for example, fragments of anti-hTNFalpha antibodies.

A need therefore exists for suitable crystallization conditions, in particular batch crystallization conditions, for antibody and antibody fragments, such as anti-hTNFalpha antibody and antibody fragments, and to establish crystallization process conditions for producing crystal volumes suitable for industrial production. A need also exists for a crystallization process that does not make use of toxic agents, which might negatively affect the pharmaceutical applicability of such antibodies. Still another need exists for a crystallization method for antibodies or antibody fragments, such as Fab or F(ab')$_2$ fragments, that allows for the selection and control of crystal size.

SUMMARY OF THE INVENTION

The above-mentioned problems are, surprisingly, solved by the invention, which provides crystallization methods and crystals produced thereby, and their use.

In one aspect, the invention provides a method for the size controlled preparation of antibody or antibody fragment crystals of a desired average uniform size range, by providing an aqueous crystallization mixture comprising an antibody or antibody fragment and at least one crystallization agent under conditions that enable the formation of antibody or antibody fragment crystals and agitating the crystallization mixture under controlled conditions, whereby antibody or antibody fragment crystals in a desired average size range, preferably being substantially uniform, are formed.

The controlled conditions have several embodiments that may be used singly or together in any combination or order. In one embodiment, the controlled conditions comprise agitating or correspond to an agitation of the crystallization mixture in a roller container at a speed in a range of from about 1 to about 200 rpm. In another embodiment, the controlled conditions comprise agitating or correspond to an agitation of the crystallization mixture in a roller container having a diameter in a range of about 2 to about 100 cm. In another embodiment, the controlled conditions correspond to an agitation of, or comprise agitating, the crystallization mixture in a roller container wherein about 1 to about 100% of the total internal volume of the roller container is filled with the crystallization mixture. In yet another embodiment, the controlled conditions correspond to an agitation of, or comprise agitating, the crystallization mixture in a roller container for about 30 minutes to about 20 days. In still another embodiment, the controlled conditions correspond to an agitation of, or comprise agitating, the crystallization mixture in a roller container at a temperature in a range of about −15 to about +50° C. The agitating step of the methods of the invention may comprise rolling, stirring, shaking and/or tumbling the crystallization mixture under conditions corresponding to rolling. Any number of the above conditions may be combined, in any order.

In another aspect, the methods of the invention provide the small and large scale production of antibody or antibody fragment crystals comprising a uniform crystal particle diameter and/or length within a range of about 1 to about 1000 μm. In another embodiment, the crystals comprise a controlled mean crystal particle length in a range of about 1 to about 200 μm. According to a further embodiment, the above crystallization methods of the present invention may also be performed such that the crystallization mixture obtained in step a) may be supplemented with a suitable amount of pre-existing antibody or antibody fragment crystals as seed crystals in order to initiate or boost the crystallization.

In an embodiment, the antibody that is crystallized is a whole antibody of any type or class, or an antibody fragment thereof. In an embodiment, the antibody fragment is a fragment of an IgG antibody, such as an IgG1, IgG2, IgG3, or IgG4 antibody. The antibody fragment may be a polyclonal antibody fragment or a monoclonal antibody fragment of, for example, a chimeric or non-chimeric antibody, humanized antibody, dual specific antibody, dual variable domain immunoglobulin (DVD-Ig™), non-glycosylated antibody, human antibody, and non-human, for example, mouse antibody. In a particular embodiment, the antibody to be crystallized is a non-chimeric, human antibody optionally further processed for improving the antigen-binding, or a fragment thereof.

In an embodiment, the antibody fragment is an anti-hTNFalpha antibody binding fragment. In a particular embodiment, the antibody fragment is an Fab or F(ab')$_2$ fragment, such as, for example, MAK195F, an F(ab')$_2$ fragment of antibody MAK195, produced by a hybridoma cell line having the deposit number ECACC 87050801 (MAK195; an anti-TNFα antibody), deposited with the European Collection of Animal Cell Cultures (ECACC), Health Protection Agency Cultures Collection, Porton Down, Salisbury SP4 OJG, united Kingdom on May 8, 1987.

In another aspect, the invention provides a batch crystallization method for crystallizing an anti-hTNFalpha antibody or antibody binding fragment by providing an aqueous crystallization mixture comprising an antibody or antibody fragment (e.g., in dissolved form) and at least one polyalkylene polyol, such as a polyalkylene glycol, as a crystallization agent and incubating the aqueous crystallization mixture until crystals of the antibody or antibody fragment are formed, wherein the polyalkylene glycol is provided either (a) in one step or (b) in more than one step, wherein the antibody crystals formed in a step are not removed prior to the next step.

In another embodiment, the pH of the aqueous crystallization mixture is in the range of about pH 4 to about 6.5, in particular about 4.5 to about 6.0, or about 4.8 to about 5.6, or about 5.0 to about 5.4, for example about 5.1, about 5.2 or about 5.3. The crystallization mixtures as outlined above are usually obtained by adding a crystallization agent in solution or as solid to the protein solution. Both solutions may be, but do not have to be, buffered. Crystallization agent concentration and buffer molarity in the original crystallization solution is usually higher than in the crystallization mixture as it is diluted when the protein solution is added. In an embodiment, the aqueous crystallization mixture may contain at least one buffer. The buffer may comprise, for example, an acetate and or a citrate component, or an alkali metal salt thereof, for example a sodium or a potassium salt, such as sodium acetate and/or sodium citrate. The salt is adjusted by the addition of an acid, such as acetic acid or citric acid, to the required pH.

In an embodiment of the crystallization method, the buffer concentration (total acetate or total citrate) in the aqueous crystallization mixture is about 0 to about 0.5 M, or about 0.02 to about 0.5 M, for example about 0.05 to about 0.3 M, about 0.07 to about 0.2 M, or about 0.09 to about 0.16 M.

In an embodiment, the polyalkylene glycol has an average molecular weight in the range of about 400 to about 10,000 g/mol. For example, the polyalkylene glycol is polyethylene glycol (PEG) and is present in the crystallization mixture at a final concentration in the range of about 5 to about 30% (w/v) of the total volume.

In another embodiment, at least one of the following additional crystallization conditions are met: (1) incubation is performed for about 1 hour to about 250 days, or about 1 day to about 250 days or about 13 days to about 250 days, for example about 1 day to about 30 days, or about 2 days to about 10 days; (2) incubation is performed at a temperature between about −15° C. and about +50° C., for example about 4° C. and about 37° C. or about 15° C. and about 25° C.; and (3) the crystallization mixture comprises an antibody or antibody fragment at a concentration in the range of about 0.5 to about 280 mg/ml, or about 1 to 200 mg/ml or about 1 to about 100 mg/ml, for example about 1.5 to about 20 mg/ml, in particular in the range of about 2 to about 15 mg/ml, or about 2 to about 7 mg/ml. The protein concentration may be determined according to standard procedures for protein determination such as, for example, by measurement of the optical density at a suitable wavelength, as for example 280 nm.

In another embodiment, the methods of the invention comprise the step of drying the crystals that are produced. Suitable drying methods include evaporative drying, spray drying, lyophilization, vacuum drying, fluid bed drying, spray freeze drying, near critical drying, supercritical drying, and nitrogen gas drying.

In a further embodiment, the crystallization methods of the invention further comprise the step of exchanging the crystallization mother liquor with a different liquid or buffer, e.g., a liquid or buffer containing at least one polyalkylene polyol different from that used for crystallization and with a molar mass in the range of about 300 to about 8,000 Daltons, or mixtures thereof, or other (polymeric) carriers, lipid carriers or oily carriers as listed herein, for example by centrifugation, diafiltration, ultrafiltration or other commonly used buffer exchange technique(s). The different liquid or buffer may be designated an "artificial mother liquor" which differs from the "natural" crystallization mother liquor of the crystals and prevents a dissolution of the crystals formed. Certain excipients in a mAb crystal formulation have the main function of hindering crystal dissolution. In that way, polyethylene glycol may be substituted in the final composition.

In a preferred embodiment, the batch crystallization method, as for example with PEG as the crystallization agent, is performed such that the incubation is performed for between about 3 to about 60 days at a temperature of about 20° C. and at an antibody concentration of about 3 to about 10 mg/ml.

In a particular embodiment of the invention, the polyalkylene glycol is added stepwise in two or more steps, for example in 2, 3, 4, 5, 6, 7, 8, 9 or 10 steps. Surprisingly, by such a stepwise addition the overall yield of antibody or antibody fragment crystals can be further increased substantially without concurrent formation of undesired amorphous protein aggregates or precipitates.

According to another embodiment, batch crystallization is performed under the following conditions of the crystallization mixture: (1) Polyalkylene glycol: PEG 4000, about 8 to about 12% (w/v) (2) buffer: sodium acetate or citrate, about 0 to about 0.3 M, (total acetate or citrate); (3) pH (final): about 5.0 to about 5.4; (4) anti-hTNFalpha fragment concentration: about 3 to about 10 mg/ml; (5) Temperature: about 18 to about 24° C.; (6) Batch volume: about 1 to about 100 l; (7) Agitation: None; or about 1 to about 100 rpm; (8) Duration: about 1 to about 60 days.

In an embodiment, the invention provides a batch crystallization method for crystallizing an anti-hTNFalpha antibody or antibody binding fragment by providing an aqueous crystallization mixture comprising an antibody or antibody fragment and at least one polyalkylene glycol as a crystallization agent; and incubating the aqueous crystallization mixture until crystals of the antibody or antibody fragment are formed; wherein the at least one polyalkylene glycol is provided either (a) in one step or (b) in more than one step, wherein the antibody crystals formed in a step are not removed before or during subsequent steps, and wherein the crystallization is performed under crystal size controlled conditions.

The controlled conditions can comprise one or more controlled conditions, in any combination. In an embodiment, the controlled conditions correspond to or comprise agitating the crystallization mixture in a roller container at a speed in a range of from about 1 to about 200 rpm. In another embodiment, the controlled conditions correspond to or comprise agitating the crystallization mixture in a roller container having a diameter in a range of about 2 to about 100 cm. In yet another embodiment, the controlled conditions correspond to or comprise agitating the crystallization mixture in a roller container wherein about 1 to, about 100% of the total internal volume of the roller container is filled with the crystallization mixture. In still another embodiment, the controlled conditions correspond to or comprise agitating the crystallization mixture in a roller container wherein about 1 to about 100% of the total internal volume of the roller container is filled with the crystallization mixture. In still another embodiment, the controlled conditions correspond to or comprise agitating the crystallization mixture in a roller container for about 30 minutes to about 20 days and/or in a roller container at a temperature in a range of about −15 to about +50° C. The agitating step may correspond to or comprise rolling, stirring, shaking and/or tumbling the crystallization mixture.

In another aspect, the invention provides crystals of an anti-hTNFalpha antibody or antibody fragment, for example, as made by any of the methods defined herein.

In an embodiment, the crystals have the shape of needles. For example, the crystals of the invention may be characterized by a needle-like morphology with a maximum length (l) of about 2 to about 500 μm or about 100 to about 300 μm and a length/diameter (l/d) ratio of about 1 to about 100. The height of such needle-like crystals is roughly in the dimension of the diameter.

In another aspect, the invention provides pharmaceutical compositions comprising: (a) crystals of an antibody or antibody fragment prepared according to the methods defined herein; and (b) at least one pharmaceutical excipient stably maintaining the antibody crystals; wherein the composition is provided as a solid, a semisolid, or a liquid formulation. In another embodiment, the invention provides a pharmaceutical composition comprising: (a) crystals of an antibody prepared according to the methods of the invention, and (b) at least one pharmaceutical excipient, wherein the excipient embeds or encapsulates the crystals.

In another embodiment, the antibody is present in a concentration greater than about 1 mg/ml. In a particular embodiment, the antibody is present in a concentration greater than about 200 mg/ml, for example about 200 to about 600 mg/ml, or about 300 to about 500 mg/ml. In another embodiment, the pharmaceutical composition is a solid comprising about 0.1 to about 9.9% (w/w) of antibody crystals.

In an embodiment, the excipient comprises at least one polymeric biodegradable or nonbiodegradable carrier and/or at least one oil or lipid carrier, including combinations or blends thereof and copolymers thereof.

Exemplary polymeric carriers comprise at least one polymer selected from the group consisting of poly (acrylic acid), poly (cyanoacrylates), poly (amino acids), poly (anhydrides), poly (depsipeptide), poly (esters), poly (lactic acid), poly (lactic-co-glycolic acid) or PLGA, poly (β-hydroxybutryate), poly (caprolactone), poly (dioxanone), poly (ethylene glycol), poly (propylene glycol), poly (hydroxypropyl)methacrylamide, poly (organo) phosphazene, poly (ortho esters), poly (vinyl alcohol), poly (vinylpyrrolidone), maleic anhydride alkyl vinyl ether copolymers, pluronic polyols, albumin, alginate, cellulose and cellulose derivatives, collagen, fibrin, gelatin, hyaluronic acid, oligo- and polysaccharides, hydroxyethylstarch, glycaminoglycans, sulfated polysaccharides, blends and copolymers thereof, and SAIB.

Lipid carriers include fatty acids and salts of fatty acids, fatty alcohols, fatty amines, mono-, di-, and triglycerides of fatty acids, phospholipids, glycolipids, sterols and waxes and related similar substances. Waxes are further classified in natural and synthetic products. Natural materials include waxes obtained from vegetable, animal or minerals sources such as beeswax, carnauba or montanwax. Chlorinated naphthalenes and ethylenic polymers are examples of synthetic wax products.

Oil (or oily liquid) carriers include an oil (or oily liquid) such as oleaginous almond oil, corn oil, cottonseed oil, ethyl oleate, isopropyl myristate, isopropyl palmitate, mineral oil, light mineral oil, octyldodecanol, olive oil, peanut oil, persic oil, sesame oil, soybean oil, squalane, liquid triglycerides, polyethoxylated castor oils, liquid waxes, and higher alcohols. Excipients still mainly connected to carriers (encapsulation/embedding):

Lipid carriers include fatty acids and salts of fatty acids, fatty alcohols, fatty amines, mono-, di-, and triglycerides of fatty acids, phospholipids, glycolipids, sterols and waxes and related similar substances. Waxes are further classified in natural and synthetic products. Natural materials include waxes obtained from vegetable, animal or minerals sources such as beeswax, carnauba or montanwax. Chlorinated naphthalenes and ethylenic polymers are examples of synthetic wax products.

Oil (or oily liquid) carriers include an oil (or oily liquid) such as oleaginous almond oil, corn oil, cottonseed oil, ethyl oleate, isopropyl myristate, isopropyl palmitate, mineral oil, light mineral oil, octyldodecanol, olive oil, peanut oil, persic oil, sesame oil, soybean oil, squalane, liquid triglycerides, liquid waxes, and higher alcohols.

In another aspect, the invention provides an injectable liquid composition comprising the antibody or antibody fragment crystals obtainable by the methods of the invention, wherein the antibody or antibody fragment is present at a concentration in a range of about 10 to about 400 mg/ml, or about 50 to about 300 mg/ml, for example about 200 mg/ml.

In another aspect, the invention provides a crystal slurry composition comprising the antibody or antibody fragment crystals obtainable by the method of the invention, wherein the antibody or antibody fragment is present in a concentration greater than about 100 mg/ml, for example about 150 to about 600 mg/ml, or about 200 to about 400 mg/ml.

In another aspect, the invention provides methods for treating a mammal comprising the step of administering to the mammal an effective amount of the antibody crystals or compositions obtainable by the methods of the invention. The methods for administration of crystals and compositions thereof, may comprise, but are not restricted to, administration by the parenteral route, by the oral route, by inhalation, by injection or combinations thereof.

In a particular embodiment, the invention provides a method of treating a hTNFalpha-related disorder in a subject comprising administering a therapeutically effective amount of the antibody crystals to the subject.

In another aspect, the invention provides uses of the anti-hTNFα antibody crystals of the invention for preparing a pharmaceutical composition for treating a hTNFalpha related disease.

The present invention also provides hTNFalpha antibody fragment crystals as defined above for use in medicine.

BRIEF DESCRIPTION OF THE DRAWINGS

The foregoing and other objects, features and advantages of the present invention, as well as the invention itself, will be more fully understood from the following description of preferred embodiments when read together with the accompanying drawings, in which.

DETAILED DESCRIPTION OF THE INVENTION

A. Definitions

Figure 1:
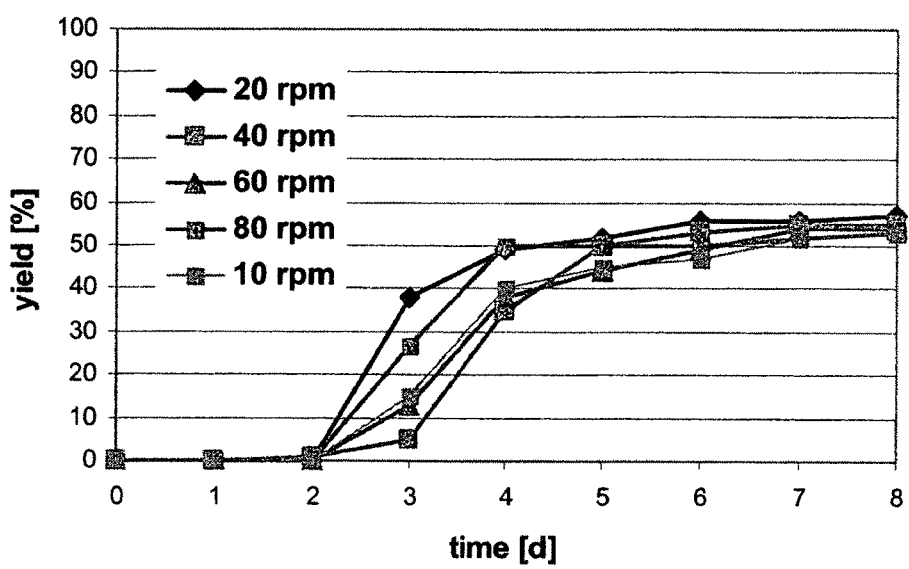
FIG. 1 shows the yields of MAK195F crystals at different roller speeds as a function of time.

"Conditions enabling the formation of antibody crystals" means any conditions of the solution that result in crystal formation under non-agitating conditions. This means that a solution is provided containing antibody molecules and at least one crystallization agent in concentrations sufficient to initiate crystal formation under the given conditions, such as pH and temperature of the mixture, over time.

"Correspond to" in the sense of the present invention means the following:

A specific crystallization technique, which includes applying agitation to the crystallization mixture in a roller container of specific geometry at a specific speed and/or a specific filling volume, constitutes a "reference system" for size-controlling crystallization. A skilled reader will be able, under the guidance of the description of said reference system, to perform size-controlled antibody crystallization under different conditions. "Different conditions" comprise, for example, up- or down-scaling of crystallization processes in a roller container, or comprise applying different agitation conditions, for example agitation by shaking, stirring or tumbling, or comprise variation of agitation speed, or combinations thereof. A "batch method of crystallization" means a crystallization method comprising the step of adding to a crystallization mixture that contains an antibody to be crystallized at least one crystallization agent, preferably in dissolved form.

A "micro scale crystallization method" means any crystallization method where the volume of the crystallization mixture is between 0.1 µL and 10 µL, especially any method enabling vapor diffusion coming into effect during crystallization. For example, a method based upon vapor diffusion comprises the steps of adding a small volume of antibody solution in the microliter range with a reservoir buffer containing a crystallization agent, placing a droplet of the mixture in a sealed container adjacent to an aliquot of the reservoir buffer; allowing exchange of solvent between the droplet and the reservoir by vapor diffusion, during which the solvent content in the droplet changes and crystallization may be observed if suitable crystallization conditions are reached.

A "crystallization agent" is an agent that favours, enhances or promotes crystal formation of an antibody to be crystallized.

A "crystallization solution" contains a crystallization agent in dissolved form. Preferably said solution is an aqueous system, i.e. the liquid constituents thereof predominantly consist of water. For example, 80 to 100 wt.-%, or 95 to 100 wt.-%, or 98 to 100 wt.-% may be water. The term "reservoir solution" also refers to a "crystallization solution" as used for microscale crystallization by vapor diffusion techniques.

A "crystallization mixture" contains the aqueous solution of an antibody or fragment thereof and the crystallization solution.

A "crystal" is one form of the solid state of matter, e.g., of a protein, which is distinct from a second solid form, i.e., the amorphous state, which exists essentially as an unorganized, heterogeneous solid. Crystals have a regular three-dimensional structure, typically referred to as a lattice. An antibody crystal comprises a regular three-dimensional array of antibody molecules. (See Giege, R. et al., Crystallization of Nucleic Acids and Proteins, a Practical Approach, 2nd ed., pp. 1-16, Oxford University Press, New York (1999)).

A "whole" or "intact" antibody is a functional antibody that is able to recognize and bind to its antigen, as for example hTNFalpha, in vitro and/or in vivo. The antibody may initiate subsequent immune system reactions of a patient associated with antibody-binding to its antigen, in particular direct cytotoxicity, complement-dependent cytotoxicity (CDC), and antibody-dependent cytotoxicity (ADCC). The antibody molecule typically has a structure composed of two identical heavy chains (MW each about 50 kDa) covalently bound to each other, and two identical light chains (MW each about 25 kDa), each covalently bound to one of the heavy chains. The four chains are arranged in a classic "Y" motif. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is generally composed of three CDRs and four FRs, arranged from amino-terminus to carboxy-terminus in the following order: FR1, CDR1, FR2, CDR2, FR3, CDR3, FR4. The complete antibody molecule has two antigen binding sites, i.e., is "bivalent". The two antigen binding sites are specific for one hTNFalpha antigen, i.e., the antibody is "mono-specific". The above structure may vary among different species.

"Monoclonal antibodies" are antibodies that are derived from a single clone of B lymphocytes (B cells), and recognize the same antigenic determinant. Whole monoclonal antibodies are those that have the above-mentioned classic molecular structure that includes two complete heavy chains and two complete light chains. Monoclonal antibodies are routinely produced by fusing the antibody-producing B cell with an immortal myeloma cell to generate B cell hybridomas, which continually produce monoclonal antibodies in cell culture. Other production methods are available, as for example expression of monoclonal antibodies in bacterial, yeast, insect, eukaryotic, or mammalian cell culture using phage-display technology, yeast display technology, or RNA display technology, for example; or in vivo production in genetically modified animals, such as cows, goats, pigs, rabbits, chickens, or in transgenic mice that have been modified to contain and express the entire human B cell genome; or production in genetically modified plants, such as tobacco and corn. Antibodies or fragments from all such sources may be crystallized according to this invention.

The monoclonal antibodies to be crystallized according to the invention include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass. An example of a mouse/human chimera containing variable antigen-binding portions of a murine antibody and constant portions derived from a human antibody.

"Humanized" forms of non-human (e.g., murine) antibodies are also encompassed by the invention. These are chimeric antibodies that contain minimal sequence derived from a non-human immunoglobulin. For the most part, humanized antibodies are human immunoglobulins in which residues from a complementarity determining region (CDR) or hypervariable loop (HVL) of the human immunoglobulin are replaced by residues from a CDR or HVL of a non-human species, such as mouse, rat, rabbit or nonhuman primate, having the desired functionality. Framework region (FR) residues of the human immunoglobulin may be replaced by corresponding non-human residues to improve antigen binding affinity. Furthermore, humanized antibodies may comprise residues that are found neither in the corresponding human or non-human antibody portions. These modifications may be necessary to further improve antibody efficacy.

A "human antibody" or "fully human antibody" is one that has an amino acid sequence that corresponds to that of an antibody produced by a human or that is recombinantly produced. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D., et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "neutralizing antibody", as used herein (or an "antibody that neutralized hTNFalpha activity"), is intended to refer to an antibody whose binding to hTNFalpha results in inhibition of the biological activity of hTNFalpha.

An "affinity matured" antibody is an antibody with one or more alterations in one or more hypervariable regions, which result in an improvement in the affinity of the antibody for antigen, compared to a parent antibody. Affinity matured antibodies have nanomolar or even picomolar affinity values for the target antigen. Affinity matured antibodies are produced by procedures known in the art. Marks et al. (1992) Bio/Technology 10:779-783 describes affinity maturation by VH and VL domain shuffling. Random mutagenesis of CDR and/or framework residues is described in Barbas et al. (1994) Proc. Nat. Acad. Sci. USA 91:3809-3813; Scier et al. (1995) Gene 169:147-155; Yelton et al. (1995) J. Immunol. 155:1994-2004; Jackson et al. (1995) J. Immunol. 154(7):3310-9; and Hawkins et al. (1992) J. Mol. Biol. 226:889-896.

An "isolated antibody", as used herein, is intended to refer to an antibody that is substantially free of other antibodies having different antigenic specificities (e.g., an isolated antibody that specifically binds hTNFalpha is substantially free of antibodies that specifically bind antigens other than hTNFalpha). An isolated antibody that specifically binds hTNFalpha may, however, have cross-reactivity to other antigens, such as hTNFalpha molecules from other species. Moreover, an isolated antibody may be substantially free of other cellular material and/or chemicals.

A "functional equivalent" of a specific "parent" antibody as crystallized according to the invention is one that shows the same antigen-specificity, but differs with respect to the molecular composition of the "parent" antibody on the amino acid level or glycosylation level. The differences, however, may be merely such that the crystallization conditions do not deviate from the parameter ranges as disclosed herein.

"Encapsulation" of antibody crystals refers to a formulation where the crystals are individually coated by at least one layer of a coating material. In a preferred embodiment, such coated crystals may have a sustained dissolution rate.

"Embedding" of antibody crystals refers to a formulation where the crystals, which may be encapsulated or not, are incorporated into a solid, liquid or semi-solid carrier in a disperse manner. Such embedded crystallized antibody molecules may be released or dissolved in a controlled, sustained manner from the carrier.

A "crystallization agent of the polyalkylene polyol type" is defined in more detail below.

A "polyalkylene polyol" as used according to the invention is a straight or branched chain, in particular straight chain, poly-$C_2$-$C_6$-alkylene polyol. The polyether is formed from at least one type of a polyfunctional aliphatic alcohol carrying 2 to 6, 2 to 4 and in particular 2 or 3, preferably vicinal, hydroxyl groups and having 2 to 6, in particular 2, 3 or 4 carbon atoms, preferably forming a linear carbon backbone. Non-limiting examples are ethylene-1,2-diol (glycol), propylene-1,2-diol, propylene-1,3-diol, and n-butylene-1,3-diol and n-butylene-1,4-diol. A particularly preferred diol is glycol.

The term "polyalkylene polyol" also comprises derivatives of the same. Non-limiting examples are alkyl esters and ethers, in particular monoalkyl ethers and dialkyl ethers. "Alkyl" is in particular defined as straight or branched-chain $C_1$-$C_6$-alkyl residue, in particular, methyl, ethyl, n- or i-propyl, n-, i-, sec.-oder tert.-butyl, n- or i-pentyl; and n-hexyl.

The polyalkylene polyols, in particular the polyalkylene glycols, as used according to the invention are further characterized by a wide range of molecular weights. The molecular weight range, stated as number or weight average molecular weight, typically is in the range of about 400 to about 10,000 g/mol, as for example about 1,000 to about 8,000 g/mol, or about 2,000 to about 6,000 g/mol, about 3,000 to about 6,000 g/mol or about 3,200 to about 6,000 g/mol, as for example about 3,350 to about 6,000 g/mol, about 3,350 to about 5000 g/mol, or about 3,800 to about 4,200 g/mol, in particular about 4,000 g/mol.

Particularly preferred polyalkylene polyols are polyethylene glycols (PEGs) and polypropylene glycols (PPGs) and corresponding random or block copolymers. Specific examples of suitable polyols are PEG 2,000; PEG 3,000; PEG 3,350; PEG 4,000; PEG 5,000; and PEG 6,000.

The polyalkylene polyol concentration, in particular the PEG concentration, in the crystallization mixture is in the range of about 5 to about 30% (w/v), as for example about 7 to about 15% (w/v) or about 9 to about 16% (w/v) or about 9 to about 14% (w/v) or about 9 to about 12% (w/v). Preferably, PEG with an average molecular weight of about 4,000 is used in a concentration in the crystallization mixture of about 9 to about 12% (w/v) in a one-step process or about 10 to about 16% (w/v) in a multi-step process.

The polyalkylene polyols of the invention may be composed of one single type of polyol or mixtures of at least two different polyols, which may be polymerized at random or may be present as block copolymers.

In a preferred embodiment of the invention, antibody protein solution and crystallization solution are combined in a ratio of about 1:1. Thus, molarities of the buffering agents/crystallization agents in the original crystallization solution are about double that in the crystallization mixture.

In a particular embodiment, the crystallization mixture comprises a batch volume in the range of about 1 ml to about 20,000 liters, or about 1 ml to about 15,000 liters, or about 1 ml to about 12,000 liters, or about 1 ml to about 10,000 liters, or about 1 ml to about 6,000 µliters, or about 1 ml to about 3,000 liters, or about 1 ml to about 1,000 liters, or about 1 ml to about 100 liters, as for example about 50 ml to about 8 liters, or about 100 ml to about 5 µliters, or about 1 liter to about 3 liters; or about 1 liter to about 1,000 liters; or about 10 liters to about 500 liters. In an embodiment, the crystallization is performed under crystal size controlled conditions as described herein.

B. Methods of Crystallization

The crystallization methods of the invention, unless otherwise indicated, are applicable to any antibody or antibody fragment. The antibody may be a polyclonal antibody or, preferably, a monoclonal antibody. The antibody may be a chimeric antibody, humanized antibody, human antibody, non-human antibody, as for example a mouse antibody, each in glycosylated or non-glycosylated form. The antibody may be a dual specific antibody (dsAb) or dual variable domain antibody (DVDAb), for example.

Unless otherwise stated the crystallization methods of the invention make use of technical equipment, chemicals and methodologies well known in the art. However, as explained above, the present invention is based on the surprising finding that the selection of specific crystallization conditions, in particular, the selection of specific crystallization agents, optionally further combined with specific pH conditions and/or concentration ranges of the corresponding agents (buffer, antibody, crystallization agent), allows for the first time to prepare reproducibly and under size control conditions and/or in a large scale, stable crystals of antibodies or antibody fragments, which can be further processed to form an active ingredient of a superior, highly advantageous pharmaceutical composition.

The starting material for performing the crystallization method normally comprises a concentrated solution of the antibody to be crystallized. The protein concentration may, for example, be in the range of about 5 to about 75 mg/ml. The solution may contain additives stabilizing the dissolved antibody. In an embodiment, it is advisable to remove the additives in advance. This can be achieved by performing a buffer exchange step described herein.

Preferably, the starting material for performing the crystallization methods of the invention contains the antibody in an aqueous solution, having a pH adjusted in the range of about 3.2 to about 8.2, or about 4.0 to about 8.0, in particular about 4.5 to about 5, preferably about 5.0 to about 5.5. The pH may be adjusted by means of a suitable buffer present in a final concentration of about 1 to about 500 mM, in particular about 1 to about 100 mM or about 1 to about 10 mM. The solution may contain additives, as for example in a proportion of about 0.01 to about 15, or about 0.1 to about 5, or about 0.1 to about 2 wt.-% based on the total weight of the solution, such as, for example, salts, sugars, sugar alcohols, and surfactants, in order to further stabilize the solution. The excipients should preferably be selected from physiologically acceptable compounds, routinely applied in pharmaceutical preparations. As non-limiting examples there may be mentioned salts, such as NaCl; surfactants, such as polysorbate 80 (Tween 80) and polysorbate 20 (Tween 20); sugars, such as sucrose and trehalose; sugar alcohols, such as mannitol and sorbitol; and buffer agents, such as phosphate-based buffer systems, such as sodium and potassium hydrogen phosphate buffers as defined above, acetate buffer, phosphate buffer, citrate buffer, TRIS buffer, maleate buffer or succinate buffer, and histidine buffer; and amino acids, such as histidine, arginine, and glycine, for example.

The buffer exchange may be performed by means of routine methods, for example, by dialysis, diafiltration or ultrafiltration.

The initial protein concentration of the aqueous solution used as starting material should be in the range of about 0.5 to about 280 mg/ml or about 1 to about 50 mg/ml.

Depending on the intended final batch size (which may be in the range of about 1 ml to about 20,000 liters) an initial volume of the aqueous antibody solution is placed in an appropriate container (as for example a vessel, bottle or tank) made of inert material, such as, for example glass, polymer or metal. The initial volume of the aqueous solution may correspond to about 30 to about 80%, normally about 50% of the final batch size.

If necessary the solution, after having been filled into the container, will be brought to standardized conditions. In particular, the temperature will be adjusted to be in the range of about 4° C. and about 37° C. If desired or advantageous, the temperature need not be kept constant, for example the temperature may be changed, and a temperature profile that provides crystals of desired shape may be applied during the crystallization process.

A crystallization solution, containing a crystallization agent in an appropriate concentration, optionally pre-conditioned in the same way as the antibody solution, is then added to the antibody solution to form a crystallization mixture.

In a first step, the bulk of crystallization agent is added to the antibody solution to a first final concentration of about 9 to 11 wt.-%, which is sufficient to initiate crystallization substantially without forming aggregates/precipitates in the initial crystallization mixture normally having a relatively high initial antibody protein concentration. After incubation for a sufficient period of time to reach a first maximum of crystal formation, a further aliquot of crystallization agent is added, optionally after having removed antibody crystals formed so far. The concentration of the crystallization agent is thereby further increased to a second final concentration by an increment of about 0.5 to about 3 wt.-%. During subsequent incubation for a sufficient period of time, as for example about 1 hour to about 5 days, additional antibody crystals are formed substantially without forming aggregates/precipitates and may be separated from the supernatant or "mother liquor". Supplementation of crystallization agent may be repeated one or more times in the same manner as long as additional antibody crystal formation is induced substantially without forming aggregates/precipitates. The end concentration of the crystallization agent may thus reach values of about 12 to about 20 wt.-%.

According to a further embodiment, the crystallization methods of the present invention may also be performed such that the crystallization mixture obtained in step a) may be supplemented with a suitable amount of pre-existing antibody crystals, as for example anti-hTNFalpha antibody binding fragment crystals, as seed crystals in order to initiate or boost the crystallization.

The addition of the crystallization solution is performed continuously or discontinuously optionally under gentle agitation in order to facilitate mixing of the two liquids. Preferably, the addition is performed under conditions where the protein solution is provided under agitation and the crystallization solution (or agent in its solid form) is added in a controlled manner.

In a preferred embodiment of the invention, crystallization is performed under controlled conditions, which correspond to an agitation of the crystallization mixture in a roller container under conditions that upon selection of at least one key parameter, for example, the roller speed, allow the control of the mean particle size of the antibody crystals formed during the course of the crystallization process. For example, the process continues until a plateau of crystal formation or maximum of crystal yield is reached, or during a predetermined period of time during the crystallization process, as for example during the main phase of crystal formation, which, for example, may be characterized by an increase of the crystallization rate of more than 5 or more than 10 or more than 15% per time interval (for example, per day).

"Correspond to" when used herein means that the specific crystallization technique applying an agitation in a roller container of specific geometry at a specific speed has to be understood as a "reference system" for size-controlling crystallization. A skilled artisan will be able, under the guidance of the description of such a reference system, to perform size-controlled antibody crystallization under different conditions, for example, up- or down-scaling of crystallization processes in a roller container, or applying different agitation conditions, for example agitation by shaking, stirring, or tumbling, or combinations thereof.

By performing a limited number of routine experiments, a skilled artisan will be able to transfer the general teachings provided herein to the reference roller container system of the present invention to a down- or up-scaled roller container crystallization method, or to a size-controlled crystallization method based on the shaking, stirring or tumbling of a crystallization mixture under suitable conditions, for example, by selecting a suitable speed of shaking, stirring or tumbling in a suitable container or vessel, selecting suitable protein and crystallization agent concentrations, temperature, duration, charging level of the container with liquid crystallization mixture and/or pH of the mixture.

According to the reference system of the present invention, a key parameter of the agitation is represented by the roller speed. In particular, the roller speed is set to a value the range of from about 1 to about 200 rpm. The roller speed may be varied within the range or an interval within the range, as for example about ±1 to about ±5, or about ±2 to about ±4 rpm, of the range. Preferably, however, the speed is set to one specific value, which is kept constant during the course of the crystallization process. For example, the roller speed may be set to a value in the range of about 2 to about 150 rpm, or about 5 to about 120 rpm or about 8 to about 100 rpm, as for example 10, 20, 30, 40, 50, 60, 70, 80 or 90 rpm. Corresponding suitable speed values may be chosen by a skilled artisan for up- or down-scaling the crystallization in a roller container or for the size-controlled crystallization by shaking, stirring or tumbling.

According to another embodiment of the reference system, the crystallization is performed under controlled conditions, which correspond to an agitation of the crystallization mixture in a roller container having a diameter in the range of about 2 to about 100 cm, as for example about 5 to about 80 or about 10 to about 50 cm. It will be understood, that the experimental setting obtained for the size-controlled crystallization in the reference roller container system may be transferred by down- or preferably up-scaling to vessels (roller containers) of smaller or preferably bigger size or internal volume. They may also be transferred to other types of vessels with smaller or preferably bigger volume, adapted for agitation by stirring, shaking or tumbling. Suitable vessel geometries are well known to a skilled artisan.

According to another embodiment of the reference system the size-controlled crystallization is performed under controlled conditions, which correspond to an agitation of the crystallization mixture in a roller container wherein about 1 to about 100 vol.-%, as for example about 4 to about 99, about 10 to about 80, about 20 to about 70, about 30 to about 60 or about 40 to about 50 vol.-% of the total internal volume of the roller container is filled with the crystallization mixture. These parameter ranges can, of course, be transferred to containers of different size and containers used for agitation by stirring, shaking or tumbling.

According to another embodiment of the reference system, the size-controlled crystallization is performed under controlled conditions, which correspond to an agitation of the crystallization mixture in a roller container for a period of time of about 30 minutes to about 60 days, for example about 1 to about 40, about 2 to about 20 or about 3 to about 10 days. These parameter ranges can, of course, be transferred to size-controlled crystallization through agitation by stirring, shaking or tumbling.

According to another embodiment of the reference system the size-controlled crystallization is performed under controlled conditions, which correspond to an agitation of the crystallization mixture in a roller container at a temperature in the range of about −15 to about +50° C., as for example about 0 to about 40, about 5 to about 30, about 10 to about 25 or about 15 to about 20° C. These parameter ranges can, of course, be transferred to size-controlled crystallization through agitation by stirring, shaking or tumbling.

A preferred reference system for the size-controlled crystallization in a roller container applies one or more of the following key-parameters, in particular a combination thereof:

| | |
|---|---|
| Roller container volume: | about 450 to about 550 ml, preferably about 500 ml |
| Roller container diameter: | about 6 to about 10 cm, preferably about 8 cm |
| Roller speed: | set to a value between about 1 to about 100 rpm |
| Filling: | about 5 to about 15, preferably about 10 vol.-% |
| Temperature: | about 15 to about 25, preferably about 20° C. |
| Duration: | about 2 to about 20, preferably about 5 to about 10 days |

By following the teaching of the present invention it is possible to adjust the mean crystal particle size (i.e., mean diameter or mean length) within a range of about 1 to about 1000 μm, for example about 5 to about 400, about 10 to about 00, about 15 to about 150, about 15 to about 100, about 15 to about 50 or about 18 to about 40 μm. In an embodiment, the antibody fragment is an anti-hTNFα antibody binding fragment. In a particular embodiment, the antibody fragment is an Fab or F(ab')$_2$ fragment, such as, for example, MAK 195F, an F(ab')$_2$ fragment of antibody MAK195, produced by a hybridoma cell line having the deposit number ECACC 87050801.

In a particular embodiment, the MAK 195F is present in an initial protein concentration in a range of about 0.5 to about 280 mg/ml and is agitated in a roller container at a speed in a range of about 5 to about 100 rpm for about 1 to about 60 days at a temperature in a range of about 15 to about 25° C.

In a preferred embodiment of the size-controlled preparation of MAK195F crystals, a MAK195F containing crystallization mixture having an initial MAK195F protein concentration in the range of about 0.5 to about 280 mg/ml, in particular about 1 to about 15 mg/ml, preferably about 5 mg/ml, is agitated in a roller container with an internal volume of about 100 ml to about 1000 liters and a diameter in the range of about 5 to about 50 cm, filled with about 5 to about 80 vol. % of crystallization mixture with a speed in the range of from about 1 to about 100 rpm for a period of about 1 to about 60 days at a temperature in the range of about 15 to about 25° C.

In an embodiment of medium scale crystallization, the MAK195F protein concentration is about 1 to about 15 mg/ml, preferably about 5 mg/ml; the roller container has a volume of about 100 to about 1000 ml and a diameter in the range of about 5 to about 10 cm, filled with about 5 to about 20 vol. % of crystallization mixture; at a roller speed in the range of from about 1 to about 100 rpm; for a duration of about 1 to about 10 days; at a temperature of about 15 to about 25° C.

In an embodiment of a large scale crystallization, the MAK195F protein concentration is about 1 to about 15 mg/ml, preferably about 5 mg/ml, in a roller container with a volume of about 10 to about 20,000 liters and a diameter in the range of about 10 cm to about 100 cm, filled with about 20 to about 90 vol. % of crystallization mixture, agitated at a roller speed in the range of from about 1 to about 10 rpm for a duration of about 1 to about 10 days, at a temperature of about 15 to about 25° C.

The formation of the antibody crystals is initiated by applying a polyalkylene polyol as defined above, in particular a polyalkylene glycol, and preferably a polyethylene glycol (PEG), or a mixture of at least two different polyalkylene polyols as defined above as the crystallization agent. The crystallization mixture contains the agent in a concentration that is sufficient to afford a final concentration of the polyalkylene polyol in the crystallization mixture in the range of about 5 to about 30% (w/v). A concentration gradient of the polyalkylene polyol as already described above may be applied as well.

Preferably, the crystallization solution additionally contains an acidic buffer, i.e., different from that of the antibody solution, in a concentration suitable to allow the adjustment of the pH of the crystallization mixture in the range of about 4 to about 6.

After having finished the addition of the crystallization agent to the crystallization solution, the mixture may be further incubated for about 1 hour to about 250 days in order to obtain a maximum yield of antibody crystals. If appropriate, the mixture may, for example, be agitated, gently stirred, rolled or moved in a manner known in the art. If it is desired to additionally control the crystal size, a size-controlled crystallization method based on agitation under controlled conditions (as already explained above) may be implemented into the batch crystallization method of the invention.

The crystals obtained may be separated by known methods, for example filtration or centrifugation, as for example by centrifugation at about 200 to about 20,000 rpm, preferably about 500 to about 2,000 rpm, at room temperature of about 4° C. The remaining mother liquor may be discarded or further processed, e.g., by adding additional crystallization agent.

If necessary, the isolated crystals may be washed and subsequently dried, or the mother liquor can be substituted with a different solvent system suitable for storage and for final use of the antibodies suspended therein.

Antibody crystals formed according to the present invention may vary in their shape, as already described above. For therapeutic administration, the size of the crystals will vary depending on the route of administration, for example, for subcutaneous administration the size of the crystals may be larger than for intravenous administration. The shape of the crystals may be altered by adding specific additional additives to the crystallization mixture, as has been previously described for both protein crystals and crystals of low molecular weight organic and inorganic molecules.

If necessary, it may be verified that the crystals are in fact crystals of the antibody. Crystals of an antibody can be analyzed microscopically for birefringence. In general, crystals, unless of cubic internal symmetry, will rotate the plane of polarization of polarized light. In yet another method, crystals can be isolated, washed, resolubilized and analyzed by SDS-PAGE and, optionally, stained with a detection antibody. Optionally, the resolubilized antibody can also be tested for binding to its antigen utilizing standard assays.

Crystals obtained according to the invention may also be crosslinked to one another. Such crosslinking may enhance stability of the crystals. Methods for crosslinking crystals is described, for example, in U.S. Pat. No. 5,849,296, which is incorporated by reference herein. Crystals can be crosslinked using a bifunctional reagent such as glutaraldehyde. Once crosslinked, crystals can be lyophilized and stored for use, for example, in diagnostic or therapeutic applications.

In some cases, it may be desirable to dry the crystals. Crystals may be dried by means of inert gases, like nitrogen gas, vacuum oven drying, lyophilization, evaporation, tray drying, fluid bed drying, spray drying, vacuum drying or roller drying. Suitable methods are well known in the art.

Crystals formed according to the invention can be maintained in the original crystallization mixture, or they can be washed and combined with other substances, such as inert carriers or ingredients to form compositions or formulations comprising crystals of the invention. Such compositions or formulations can be used, for example, in therapeutic and diagnostic applications.

In a preferred embodiment, a suitable carrier or ingredient is combined with the crystals of the invention such that the crystals of the formulation are embedded or encapsulated by an excipient. Suitable carriers or crystallization agents may be taken from the non limiting group of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (β-hydroxybutryate), poly (caprolactone), dimethylsiloxane/methylvinylsiloxane copolymers, ethylene vinylacetate copolymers, poly[bis(p-carboxyphenoxy)propane anhydride]sebacic acid, polyglactin, polysiloxane, poly (dioxanone); poly (ethylene glycol), poly (hydroxypropyl)methacrylamide, poly (organo) phosphazene, poly (ortho esters), poly (vinyl alcohol), poly (vinylpyrrolidone), maleic anhydride alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, hydroxyethyl-starch, blends and copolymers thereof, SAIB, fatty acids and salts of fatty acids, fatty alcohols, fatty amines, mono-, di-, and triglycerides of fatty acids, phospholipids, glycolipids, sterols and waxes and related similar substances. Waxes are further classified in natural and synthetic products. Natural materials include waxes obtained from vegetable, animal or minerals sources such as beeswax, carnauba or montanwax. Chlorinated naphthalenes and ethylenic polymers are examples for synthetic wax products.

C. Compositions

In another aspect, the invention provides compositions and formulations comprising antibody crystals in combination with at least one carrier and/or excipient. The formulations may be solid, semisolid or liquid.

Formulations of the invention are prepared, in a form suitable for storage and/or for use, by mixing the antibody having the necessary degree of purity with a physiologically acceptable additive, such as a carrier, excipient, and/or stabilizer (see, for example, Remington's Pharmaceutical Sciences, 16th Edn., Osol, A. Ed. (1980)), in the form of suspensions, or are lyophilized or dried in another manner. Optionally, further active ingredients, such as different antibodies, biomolecules, or chemically or enzymatically synthesized low-molecular weight molecules may be incorporated as well.

Acceptable additives are non-toxic to recipients at the dosages and concentrations employed. Non-limiting examples thereof include:

Acidifying agents, such as acetic acid, citric acid, fumaric acid, hydrochloric acid, malic acid, nitric acid, phosphoric acid, diluted phosphoric acid, sulfuric acid, and tartaric acid;

Aerosol propellants, such as butane, dichlorodifluoromethane, dichlorotetrafluoroethane, isobutane, propane, and trichloromonofluoromethane;

Air displacements, such as carbon dioxide and nitrogen;

Alcohol denaturants, such as methyl isobutyl ketone and sucrose octacetate;

Alkalizing agents, such as ammonia solution, ammonium carbonate, diethanolamine, diisopropanolamine, potassium hydroxide, sodium bicarbonate, sodium borate, sodium carbonate, sodium hydroxide, and trolamine;

Antifoaming agents, such as dimethicone and simethicone;

Antimicrobial preservatives, such as benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, and thymol;

Antioxidants, such as ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, and tocopherols excipient;

Buffering agents, such as acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, histidine;

Chelating agents, such as edetate disodium, ethylenediaminetetraacetic acid and salts, and edetic acid;

Coating agents, such as sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein, poly amino acids, other polymers such as PLGA, etc., and SAIB;

Coloring agents, such as ferric oxide;

Complexing agents, such as ethylenediaminetetraacetic acid and salts (EDTA), edetic acid, gentisic acid ethanolamide, and oxyquinoline sulphate;

Desiccants, such as calcium chloride, calcium sulfate, and silicon dioxide;

Emulsifying and/or solubilizing agents, such as acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, and emulsifying wax;

Filtering aids, such as powdered cellulose and purified siliceous earth;

Flavors and perfumes, such as anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, and vanillin;

Glidant and/or anticaking agents, such as calcium silicate, magnesium silicate, colloidal silicon dioxide, and talc;

Humectants, such as glycerin, hexylene glycol, propylene glycol, and sorbitol;

Ointment bases, such as lanolin, anhydrous lanolin, hydrophilic ointment, white ointment, yellow ointment, polyethylene glycol ointment, petrolatum, hydrophilic petrolatum, white petrolatum, rose water ointment, and squalane;

Plasticizers, such as castor oil, lanolin, mineral oil, petrolatum, benzyl benzyl formate, chlorobutanol, diethyl pthalate, sorbitol, diacetylated monoglycerides, diethyl phthalate, glycerin, glycerol, mono- and di-acetylated monoglycerides, polyethylene glycol, propylene glycol, triacetin, triethyl citrate, and ethanol;

Polypeptides, such as low molecular weight (less than about 10 residues);

Proteins, such as serum albumin, gelatin, and immunoglobulins;

Polymer membranes, such as cellulose acetate membranes;

Solvents, such as acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water, liquid triglycerides, liquid waxes, and higher alcohols;

Sorbents, such as powdered cellulose, charcoal, purified siliceous earth, carbon dioxide sorbents, barium hydroxide lime, and soda lime;

Stiffening agents, such as hydrogenated castor oil, cetostearyl alcohol, cetyl alcohol, cetyl esters wax, hard fat, paraffin, polyethylene excipient, stearyl alcohol, emulsifying wax, white wax, and yellow wax;

Suppository bases, such as cocoa butter, hard fat, and polyethylene glycol;

Suspending and/or viscosity-increasing agents, such as acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, and tragacanth, xanthan gum;

Sweetening agents, such as aspartame, dextrates, dextrose, excipient dextrose, fructose, mannitol, saccharin, calcium saccharin, sodium saccharin, sorbitol, solution sorbitol, sucrose, compressible sugar, confectioner's sugar, and syrup;

Tablet binders, such as acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, and syrup;

Tablet and/or capsule diluents, such as calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, and confectioner's sugar;

Tablet disintegrants, such as alginic acid, microcrystalline cellulose, croscarmellose sodium, corspovidone, polacrilin potassium, sodium starch glycolate, starch, and pregelatinized starch.

Tablet and/or capsule lubricants, such as calcium stearate, glyceryl behenate, magnesium stearate, light mineral oil, polyethylene glycol, sodium stearyl fumarate, stearic acid, purified stearic acid, talc, hydrogenated vegetable oil, and zinc stearate;

Tonicity agents, such as dextrose, glycerin, mannitol, potassium chloride, sodium chloride;

Vehicle, such as flavored and/or sweetened aromatic elixir, compound benzaldehyde elixir, iso-alcoholic elixir, peppermint water, sorbitol solution, syrup, and tolu balsam syrup;

Vehicles, such as oleaginous almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane; solid carrier sugar spheres; sterile bacteriostatic water for injection, bacteriostatic sodium chloride injection, liquid triglycerides, liquid waxes, and higher alcohols;

Water repelling agents, such as cyclomethicone, dimethicone and simethicone; and Wetting and/or solubilizing agents, such as benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, and tyloxapol.

The crystals may be combined with a polymeric carrier to provide for stability and/or sustained release. Such polymers include biocompatible and biodegradable polymers. A polymeric carrier may be a single polymer type or it may be composed of a mixture of polymer types. Nonlimiting examples of polymeric carriers have already been provided above.

Examples of preferred ingredients or excipients include:
  salts of amino acids such as glycine, arginine, aspartic acid, glutamic acid, lysine, asparagine, glutamine, proline, and histidine;
  monosaccharides, such as glucose, fructose, galactose, mannose, arabinose, xylose, and ribose;
  disaccharides, such as lactose, trehalose, maltose, and sucrose;
  polysaccharides, such as maltodextrins, dextrans, starch, and glycogen;
  alditols, such as mannitol, xylitol, lactitol, and sorbitol;
  glucuronic acid and galacturonic acid;
  cyclodextrins, such as methyl cyclodextrin, hydroxypropyl-(3-cyclodextrin);
  inorganic salts, such as sodium chloride, potassium chloride, magnesium chloride, phosphates of sodium and potassium, boric acid ammonium carbonate and ammonium phosphate;
  organic salts, such as acetates, citrate, ascorbate, and lactate;
  emulsifying or solubilizing agents such as acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; and
  viscosity increasing reagents such as, agar, alginic acid and its salts, guar gum, pectin, polyvinyl alcohol, polyethylene oxide, cellulose and its derivatives propylene carbonate, polyethylene glycol, hexylene glycol and tyloxapol.

Formulations described herein also comprise an effective amount of crystalline antibody. In particular, the formulations of the invention may include a "therapeutically effective amount" or a "prophylactically effective amount" of antibody crystals of the invention. A "therapeutically effective amount" refers to an amount effective, at dosages and for periods of time necessary, to achieve the desired therapeutic result. A "therapeutically effective amount" of the antibody crystals may vary according to factors such as the disease state, age, sex, and weight of the individual, and the ability of the antibody to elicit a desired response in the individual. A therapeutically effective amount is also one in which any toxic or detrimental effects of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Suitable dosages can readily be determined using standard methodology. The antibody is suitably administered to the patient at one time or over a series of treatments. Depending on the above mentioned factors, about 1 μg/kg to about 50 mg/kg, as for example about 0.1 to about 20 mg/kg of antibody is an initial candidate dosage for administration to the patient, whether, for example, by one or more separate administrations, or by continuous infusion. A typical daily or weekly dosage might range from about 1 μg/kg to about 20 mg/kg or more, depending on the condition, the treatment is repeated until a desired suppression of disease symptoms occurs. However, other dosage regimens may be useful. In some cases, formulations comprise a concentration of antibody of at least about 1 g/L or greater when resolubilized. In other embodiments, the antibody concentration is at least about 1 g/L to about 100 g/L when resolubilized.

Crystals of an antibody, or formulations comprising such crystals, may be administered alone or as part of a pharmaceutical preparation. Crystals of the invention may be administered by oral, parenteral, pulmonary, nasal, aural, anal, dermal, ocular, intravenous, intramuscular, intraarterial, intraperitoneal, mucosal, sublingual, subcutaneous, transdermal, topical or intracranial routes, or into the buccal cavity, for example. Specific examples of administration techniques comprise pulmonary inhalation, intralesional application, needle injection, dry powder inhalation, skin electroporation, aerosol delivery, and needle-free injection technologies, including needle-free subcutaneous administration.

The hTNFalpha-related disorder may be selected from the following list of diseases:

Acquired Immunodeficiency Disease Syndrome
Acquired Immunodeficiency Related Diseases
Acquired pernicious anaemia
Acute coronary syndromes
Acute and chronic pain (different forms of pain)
Acute Idiopathic Polyneuritis
Acute immune disease associated with organ transplantation
Acute or chronic immune disease associated with organ transplantation
Acute Inflammatory Demyelinating Polyradiculoneuropathy
Acute ischemia
Acute liver disease
Acute rheumatic fever
Acute transverse myelitis
Addison's disease
Adult (acute) respiratory distress syndrome
Adult Still's Disease
Alcoholic cirrhosis
Alcohol-induced liver injury
Allergic diseases
Allergy
Alopecia
Alopecia areata
Alzheimer's disease
Anaphylaxis
Ankylosing spondylitis
Ankylosing spondylitis associated lung disease
Anti-Phospholipid Antibody Syndrome
Aplastic anemia
Arteriosclerosis
Arthropathy
Asthma
Atheromatous disease/arteriosclerosis
Atherosclerosis
Atopic allergy
Atopic eczema
Atopic dermatitis
Atrophic autoimmune hypothyroidism
Autoimmune bullous disease
Autoimmune dermatitis
Autoimmune diabetes
Autoimmune disorder associated with Streptococcus infection
Autoimmune Enteropathy
Autoimmune haemolytic anaemia
Autoimmune hepatitis
Autoimmune hearingloss
Autoimmune Lymphoproliferative Syndrome (ALPS)
Autoimmune mediated hypoglycaemia
Autoimmune myocarditis
Autoimmune neutropenia
Autoimmune premature ovarian failure
Autoimmune thrombocytopenia (AITP)
Autoimmune thyroid disease
Autoimmune uveitis
Bronchiolitis obliterans
Behcet's disease
Blepharitis
Bronchiectasis -continued Bullous pemphigoid
Cachexia
Cardiovascular Disease
Catastrophic Antiphospholipid Syndrome
Celiac Disease
Cervical Spondylosis
Chlamydia
Choleosatatis
Chronic active hepatitis
Chronic eosinophilic pneumonia
Chronic fatigue syndrome
Chronic immune disease associated with organ transplantation
Chronic ischemia
Chronic liver diseases
Chronic mucocutaneous candidiasis
Cicatricial pemphigoid
Clinically isolated Syndrome (CIS) with Risk for Multiple Sclerosis
Common varied immunodeficiency (common variable hypogammaglobulinaemia)
Connective tissue disease associated interstitial lung disease
Conjunctivitis
Coombs positive haemolytic anaemia
Childhood Onset Psychiatric Disorder
Chronic obstructive pulmonary disease (COPD)
Crohn's disease
Cryptogenic autoimmune hepatitis
Cryptogenic fibrosing alveolitis
Dacryocystitis
Depression
Dermatitis scleroderma
Dermatomyositis
Dermatomyositis/polymyositis associated lung disease
Diabetic retinopathy
Diabetes mellitus
Dilated cardiomyopathy
Discoid lupus erythematosus
Disk herniation
Disk prolaps
Disseminated intravascular coagulation
Drug-Induced hepatitis
Drug-induced interstitial lung disease
Drug induced immune hemolytic anemia
Endocarditis
Endometriosis
Endophthalmitis
Enteropathic synovitis
Episcleritis
Erythema multiforme
Erythema multiforme major
Female infertility
Fibrosis
Fibrotic lung disease
Gestational pemphigoid
Giant cell arteritis (GCA)
Glomerulonephritides
Goitrous autoimmune hypothyroidism (Hashimoto's disease)
Goodpasture's syndrome
Gouty arthritis
Graft versus host disease (GVHD)
Grave's disease
Group B streptococci (GBS) infection
Guillain-Barre Syndrome (GBS)
haemosiderosis associated lung disease
Hay Fever
Heart failure
Hemolytic anemia
Henoch-Schoenlein purpurea
Hepatitis B
Hepatitis C
Hughes Syndrome
Huntington's chorea
Hyperthyroidism
Hypoparathyroidism
Idiopathic leucopaenia
Idiopathic thrombocytopaenia
Idiopathic Parkinson's Disease
Idiopathic interstitial pneumonia
Idiosyncratic liver disease
IgE-mediated Allergy
Immune hemolytic anemia Inclusion Body Myositis
Infectious diseases
Infectious ocular inflammatory disease
Inflammatory bowel disease
Inflammatory demyelinating disease
Inflammatory heart disease
Inflammatory kidney disease
Insulin dependent diabetes mellitus
Interstitial pneumonitis
IPF/UIP
Iritis
Juvenile chronic arthritis
Juvenile pernicious anaemia
Juvenile rheumatoid arthritis
Kawasaki's disease
Keratitis
Keratojuntivitis sicca
Kussmaul disease or Kussmaul-Meier Disease
Landry's Paralysis
Langerhan's Cell Histiocytosis
Linear IgA disease
Livedo reticularis
Lyme arthritis
Lymphocytic infiltrative lung disease
Macular Degeneration
Male infertility idiopathic or NOS
Malignancies
Microscopic vasculitis of the kidneys
Microscopic Polyangiitis
Mixed connective tissue disease associated lung disease
Morbus Bechterev
Motor Neuron Disorders
Mucous membrane pemphigoid
Multiple sclerosis (all subtypes: primary progressive, secondary progressive, relapsing remitting etc.)
Multiple Organ failure
Myalgic encephalitis/Royal Free Disease
Myasthenia Gravis
Myelodysplastic Syndrome
Myocardial infarction
Myocarditis
Nephrotic syndrome
Nerve Root Disorders
Neuropathy
Non-alcoholic Steatohepatitis
Non-A Non-B Hepatitis
Optic Neuritis
Organ transplant rejection
Osteoarthritis
Osteolysis
Ovarian cancer
Ovarian failure
Pancreatitis
Parasitic diseases
Parkinson's disease
Pauciarticular JRA
Pemphigoid
Pemphigus foliaceus
Pemphigus vulgaris
Peripheral artery occlusive disease (PAOD)
Peripheral vascular disease (PVD)
Peripheral artery disease (PAD)
Phacogenic uveitis
Phlebitis
Polyarteritis nodosa (or periarteritis nodosa)
Polychondritis
Polymyalgia Rheumatica
Poliosis
Polyarticular JRA
Polyendocrine Deficiency Syndrome
Polymyositis
Polyglandular deficiency type I and polyglandular deficiency type II
polymyalgia rheumatica (PMR)
Postinfectious interstitial lung disease
Post-inflammatory interstitial lung disease
Post-Pump Syndrome
Premature ovarian failure
Primary biliary cirrhosis
Primary myxoedema
Primary parkinsonism
Primary sclerosing cholangitis
Primary sclerosing hepatitis
Primary vasculitis
Prostate and rectal cancer and hematopoietic malignancies (leukemia and lymphoma)
Prostatitis
Psoriasis
Psoriasis type 1
Psoriasis type 2
Psoriatic arthritis
Psoriatic arthropathy
Pulmonary hypertension secondary to connective tissue disease
Pulmonary manifestation of polyarteritis nodosa
Pure red cell aplasia
Primary Adrenal Insufficiency
Radiation fibrosis
Reactive arthritis
Reiter's disease
Recurrent Neuromyelitis Optica
Renal disease NOS
Restenosis
Rheumatoid arthritis
Rheumatoid arthritis associated interstitial lung disease
Rheumatic heart disease
SAPHO (synovitis, acne, pustulosis, hyperostosis, and osteitis)
Sarcoidosis
Schizophrenia
Schmidt's syndrome
Scleroderma
Secondary Amyloidosis
Shock lung
Scleritis
Sciatica
Secondary Adrenal Insufficiency
Sepsis syndrome
Septic arthritis
Septic shock
Seronegative arthopathy
Silicone associated connective tissue disease
Sjögren's disease associated lung disease
Sjörgren's syndrome
Sneddon-Wilkinson Dermatosis
Sperm autoimmunity
Spondyloarthropathy
Spondilitis ankylosans
Stevens-Johnson Syndrome (SJS)
Still's disease
Stroke
Sympathetic ophthalmia
Systemic inflammatory response syndrome
Systemic lupus erythematosus
Systemic lupus erythematosus associated lung disease
Systemic sclerosis
Systemic sclerosis associated interstitial lung disease
Takayasu's disease/arteritis
Temporal arteritis
Th2 Type and Th1 Type mediated diseases
Thyroiditis
Toxic shock syndrome
Toxoplasmic retinitis
toxic epidermal necrolysis
Transverse myelitis
TRAPS (Tumor Necrosis Factor Receptor
Type B insulin resistance with acanthosis nigricans
Type 1 allergic reaction
Type-1 autoimmune hepatitis (classical autoimmune or lupoid hepatitis)
Type-2 autoimmune hepatitis (anti-LKM antibody hepatitis)
Type II Diabetes
Ulcerative colitic arthropathy
Ulcerative colitis
Urticaria
Usual interstitial pneumonia (UIP)
Uveitis
Vasculitic diffuse lung disease
Vasculitis
Vernal conjunctivitis
Viral retinitis
Vitiligo Vogt-Koyanagi-Harada syndrome (VKH syndrome)
Wegener's granulomatosis
Wet macular degeneration
Wound healing
Yersinia and salmonella associated arthropathy The hTNFalpha-related disorder may also be selected from the following list of diseases: rheumatoid spondylitis, pulmonary disorder, intestinal disorder, cardiac disorder, inflammatory bone disorders, bone resorption disease, viral hepatitis, fulminant hepatitis, coagulation disturbances, burns, reperfusion injury, keloid formation, scar tissue formation, pyrexia, periodontal disease, obesity and radiation toxicity; a spondyloarthropathy, a metabolic disorder, anemia, pain, a hepatic disorder, a skin disorder, a nail disorder, idiopathic pulmonary fibrosis (IPF), anemia, pain, a Crohn's disease-related disorder, chronic plaque psoriasis, age-related cachexia, brain edema, inflammatory brain injury, drug reactions, edema in and/or around the spinal cord, familial periodic fevers, Felty's syndrome, post-streptococcal glomerulonephritis or IgA nephropathy, loosening of prostheses, multiple myeloma, cancer, multiple organ disorder, orchitism osteolysis, including acute, chronic, and pancreatic abscess, periodontal disease, progressive renal failure, pseudogout, pyoderma gangrenosum, relapsing polychondritis, sclerosing cholangitis, stroke, thoracoabdominal aortic aneurysm repair (TAAA), symptoms related to Yellow Fever vaccination, inflammatory diseases associated with the ear, such as chronic ear inflammation or pediatric ear inflammation, and choroidal neovascularization or lupus.

mate molecular weight of 100 kDa. The F(ab')$_2$-fragment is produced by peptic digest of the IgG$_3$-monoclonal antibody and is composed of two heterodimers. The heterodimers are composed of a light chain polypeptide and Fd' parts of the heavy chain polypeptide of the IgG$_3$ antibody. The four chains of the antibody molecule are linked together and internally by disulfide bonds. All the cysteine residues of the light chains and of the Fd' parts of the heavy chains are involved in disulfide linkages. The following pairs of cysteine residues are expected to be connected by disulfide linkages: linkages within the light chains: L23-L88 and L134-L194, linkages within the Fd' fragments: H22-H95 and H144-H198, linkage between light chains and Fd' fragments: L214-H132, linkage between the Fd' fragments: H229-H229. The expected disulfide pattern is based on comparing the amino acid sequences of the Afelimomab™ polypeptides with the highly homologous amino acid sequences of IgG antibodies with known disulfide structure. The formation of the disulfide linkages is incomplete for all disulfide linkages to a certain degree with approximately 0.3 cysteine residues per F(ab')$_2$ molecule being found to be present as free cysteine.

The light chains comprise 214 amino acids each. The amino acid sequence of the light chains is illustrated below. Apart from deamidation of a single asparagine residue ($Asn_{L157}$), no variations of the covalent structure of the light chains were detected. The amino acid sequence of the heavy chains of the complete IgG$_3$ antibody comprise 447 amino acids each. The amino acid sequence is shown below. The N-terminus of the heavy chains as derived from the cDNA sequence starts with the amino acid glutamine. This amino acid is completely converted into pyroglutamic acid.

```
Amino Acid Sequence of the Light Chains of the Afelimomab ™ Molecule
                                                              (SEQ ID NO:1)
DIVMTQSHKF MSTTVGDRVS ITCKASQAVS SAVAWYQQKP GQSPKLLIYW          50

ASTRHTGVPD RFTGSGSVTD FTLTIHNLQA EDLALYYCQQ HYSTPFTFGS         100

GTKLEIKRAD AAPTVSIFPP SSEQLTSGGA SVVCFLNNFY PKDINVKWKI         150

DGSERQNGVL NSWTDQDSKD STYSMSSTLT LTKDEYERHN SYTCEATHKT         200

STSPIVKSFN RNEC                                               214

Amino Acid Sequence of the Heavy Chains of the Afelimomab ™ Molecule
                                                              (SEQ ID NO:2)
QVQLKESGPG LVAPSQSLSI TCTVSGFSLT DYGVNWVRQP PGKGLEWLGM          50

IWGDGSTDYD STLKSRLSIS KDNSKSQIFL KNNSLQTDDT ARYYCAREWH         100

HGPVAYWGQG TLVTVSAATT TAPSVYPLVP GCSDTSGSSV TLGCLVKGYF         150

PEPVTVKWNY GALSSGVRTV SSVLQSGFYS LSSLVTVPSS TWPSQTVICN         200

VAHPASKTEL IKRIEPRIPK PSTPPGSSCP PGNILGGPSVFIFPPKPKDA          250

Hinge region

LMISLTPKVT CVVVDVSEDD PDVHVSWFVD NKEVHTAWTQ PREAQYNSTF         300

RVVSALPIQH QDWMRGKEFK CKVNNKALPA PIERTISKPK GRAQTPQVYT         350

IPPPREQMSK KKVSLTCLVT NFFSEAISVE WERNGELEQD YKNTPPILDS         400

DGTYFLYSKL TVDTDSWLQG EIFTCSVVHE ALHNHHTQKN LSRSPGK           447
```

D. MAK195F

MAK195F, also known as Afelimomab™, is an F(ab')$_2$-fragment of a murine IgG$_3$ monoclonal antibody specific for Tumor Necrosis Factor alpha (TNFalpha) with an approxi- The proteolytic cleavage responsible for the formation of the N-terminal Fd' fragments takes place in the hinge region and leads to cleavage at the C-terminal side of the amino acids at positions H233 (resulting C-terminus of the Fd' fragment . . . PPGN (SEQ ID NO:3)), H235 ( . . . PPGNIL (SEQ ID NO:4)), H236 ( . . . PPGNILG (SEQ ID NO:5)), H239 ( . . . NILGGPS (SEQ ID NO:6)), H240 ( . . . NILGGPSV (SEQ ID NO:7)) and H241 ( . . . NILGGPSVF (SEQ ID NO:8)). Except for cleavage at position H236, the cleavage positions are specific for pepsin, the proteloytic agent used for the production of the Afelimomab™ API. The cleavage at position H236 was shown to be due to cathepsin D. Cathepsin D is present in the cell free supernatant and is an acidic protease such as pepsin. The content of this endogeneous protease may be reduced by a chromatographic step. Due to the limited specificity of pepsin the C-termini of the heavy chain polypeptides of the F(ab')$_2$ molecule exhibit a certain degree of heterogeneity.

Partial O-glycosylation at $Ser_{H222}$ constitutes another source of heterogeneity of the Afelimomab™ molecule. Approximately 70% of the Fd' fragments are non-glycosylated. Among the glycosylated fragments the predominant oligosaccharide structure bound to $Ser_{H222}$ was identified as GalNAc-Gal-NGNA (GalNAc: N-acetylgalactoseamine, Gal: galactose, NGNA: N-glycolylneuraminic acid). In addition, to a smaller extent oligosaccharides without or with two NGNA moieties were found (see below).

GmbH, Sulzbach. Furthermore, commercial crystallization screens and reagents (Hampton Research, Emerald BioStructures, Jena Bioscience) were used for certain microscale experiments. All other chemicals were from Sigma-Aldrich, Steinheim, or Merck, Darmstadt.

B. General Methods a) Thawing of Afelimomab™ (MAK195F) Drug Substance
MAK195F was thawed at 25° C. in agitated water baths.
b1) Buffer Exchange—Method A
An aliquot of the MAK195F solution was displaced into a SLIDE-A-LYZER dialysis cassette (Pierce Biotechnology Inc.). The dialysis cassette was placed into a beaker containing the buffer of choice, and the buffer exchange was performed at 4° C. overnight under stirring. After adjustment of protein concentration, the solution was sterile filtered through a 0.2 μm syringe driven filter unit.
b2) Buffer Exchange—Method B
An aliquot of the MAK195F solution was pipetted into a 30 KDa MWCO Vivaspin 4 concentrator (Vivascience). The protein sample was diluted with the new buffer in a ratio of 1:4,

TABLE 1

Variations of the Covalent Structure of the Fd'-Part of the Afelimomab ™ Molecule

| Source of Variation | Resulting Fd'-Fragment of the Afelimomab ™ Molecule |
|---|---|
| Formation of pyroglutamic acid at the N-Terminus | Starting with $PyrE_1VQL$ . . . and ending with the C-Terminus |
| Proteolytic processing of the C-Terminus | C-Terminus ending with . . . PPGN (SEQ ID NO:3) |
| | C-Terminus ending with . . . PPGNIL (SEQ ID NO:4) |
| | C-Terminus ending with . . . NILG (SEQ ID NO:9) |
| | C-Terminus ending with . . . NILGGPS (SEQ ID NO:6) |
| | C-Terminus ending with . . . NILGGPSV (SEQ ID NO:7) |
| | C-Terminus ending with . . . NILGGPSVF (SEQ ID NO:8) |
| O-linked glycosylation at $Ser_{H222}$ | Gal-GalNAc-$Ser_{H222}$ (relative abundance appr. 10%) |
| | $NGNA_1$-Gal-GalNAc-$Ser_{H222}$ (relative abundance appr. 70%) |
| | $NGNA_2$-Gal-GalNAc-$Ser_{H222}$ (relative abundance appr. 20%) |

Practice of the invention will be still more fully understood from the following examples, which are presented herein for illustration only and should not be construed as limiting the invention in any way. Guided by the general part of the description and on the basis of his general knowledge a skilled artisan will be enabled to provide further embodiments to the invention without undue experimentation.

EXEMPLIFICATION

A. Materials a) Protein
All experiments were performed using MAK195F lot G008.01E/PZ0105P025, where the original mAb concentration was 12.39 mg/mL.
b) Fine Chemicals
Sodium acetate was obtained from Grüssing GmbH, Filsum. Polyethylene glycol 4,000 was obtained from Clariant and by centrifugation at 10,000×g at 4° C. (Sigma 4 K 15 lab centrifuge) the sample volume was brought back to the original sample volume. The dilution/centrifugation steps were repeated twice, resulting in a dilution of 1:64 of the original sample buffer. After adjustment of protein concentration, the solution was sterile filtered through a 0.2 μm syringe driven filter unit.
b3) Buffer Exchange—Method C
An aliquot of the MAK195F solution was pipetted into a 30 KDa MWCO Vivaspin 20 concentrator (Vivascience). The protein sample was diluted with the new buffer in a ratio of 1:10, and by centrifugation at 5,000×g at 4° C. (Sigma 4 K 15 lab centrifuge) the sample volume was brought back to the original sample volume. The dilution/centrifugation steps were repeated once, resulting in a dilution of 1:100 of the original sample buffer. After adjustment of protein concentration, the solution was sterile filtered through a 0.2 μm syringe driven filter unit.

b4) Buffer Exchange—Method D

An aliquot of the MAK195F solution was pipetted into a 30 KDa MWCO Vivaspin 20 concentrator (Vivascience). The protein sample was concentrated to 1:10 of the original volume by centrifugation at 5,000×g at 4° C. (Sigma 4 K 15 lab centrifuge). Subsequently, the concentrated sample was diluted with the new buffer to the original sample volume. The centrifugation/dilution steps were repeated once, resulting in a dilution of 1:100 of the original sample buffer. After adjustment of protein concentration, the solution was sterile filtered through a 0.2 µm syringe driven filter unit.

b5) Buffer Exchange—Method E

An aliquot of the MAK195F solution was added to a beaker. A 30 KDa MWCO Vivaspin 50 concentrator (Vivascience) was rinsed with ultrapure water, and using a Masterflex EasyLoad II pump, the original sample volume was brought to 1:4. The protein sample was subsequently diluted to the original volume. Concentration/dilution steps were repeated three times, resulting in an overall dilution of the original buffer of 1:256. After adjustment of the protein concentration, the solution was sterile filtered through a 0.2 µm syringe driven filter unit.

c) $OD_{280}$—Protein Concentration Measurements

A ThermoSpectronics UV1 device was used to assess the protein concentration at a wavelength of 280 nm, applying an extinction coefficient of 1.37 $cm^2\ mg^{-1}$. For this purpose, aliquots of crystallization slurries were centrifuged at 14,000 rpm, and the residual protein concentration in the supernatant was determined.

d) pH Measurements pH measurements were conducted using a Mettler Toledo MP220 pH meter. Inlab 413 electrodes and Inlab 423 microelectrodes were utilized.

e1) Microscale Crystallization—Sitting Drop Vapor Diffusion Hydra II

Initial crystallization screens were performed using a Hydra II crystallization roboter and Greiner 96 well plates (three drop wells, Hampton Research). After setting up the plates, the wells were sealed with Clearseal film (Hampton Research).

e2) Microscale Crystallization—Hanging Drop Vapor Diffusion

Hanging drop vapor diffusion experiments were conducted using VDX plates (with sealant, Hampton Research) and OptiClear plastic cover slides (squares, Hampton Research) or siliconized glass cover slides (circular, Hampton Research), respectively. After preparation of reservoir solutions, one drop of reservoir solution was mixed with one drop of the protein solution on a cover slide, and the well was sealed with the inverted cover slide in that way that the drop was hanging above the reservoir.

f1) Batch Crystallization—Method A (96/24 Well Plate)

Batch crystallization was performed by mixing the protein solution with an equal amount of crystallization solution in a well. The well was subsequently sealed with adhesive tape to prevent water evaporation.

f2) Batch Crystallization—Method B (Eppendorff Reaction Tube)

Batch crystallization was performed by mixing the protein solution with an equal amount of crystallization solution in a 1.5 mL or a 2 mL Eppendorff reaction tube.

f3) Batch Crystallization—Method C (Falcon Tubes, No Agitation)

Batch crystallization was performed by mixing the protein solution with an equal amount of crystallization solution in a 50 mL Falcon tube.

f4) Batch Crystallization—Method D (Falcon Tubes, Agitation)

Batch crystallization was performed by mixing the protein solution with an equal amount of crystallization solution in a 50 mL Falcon tube. Right after closing, the tube was put on a laboratory shaker (GFL 3013 or GFL 3015) or was alternatively agitated by rolling. By the applied methods, introduction of stirrers into the sample was avoided.

f5) Batch Crystallization—Method E (1 Liter Polypropylene Container, Agitation or No Agitation)

Batch crystallization was performed by mixing the protein solution with an equal amount of crystallization solution in a sterilized 1 liter polypropylene bottle. Right after closing, the container was agitated by rolling or was not agitated. By the applied method, introduction of stirrers into the sample was avoided.

g) SDS-PAGE

Samples were prepared by adjusting the protein concentration to 8 µg/20 µL. The samples were diluted with an SDS/Tris/Glycerine buffer containing bromophenol blue.

Qualitative SDS PAGE analysis was performed using Invitrogen NuPage 10% Bis-Tris Gels, NuPage MES SDS Running Buffer and Mark12 Wide Range Protein Standards. 20 µL of sample was pipetted into a gel pocket. After running the gel and fixation with acetic acid/methanol reagent, staining was performed using the Novex Colloidal Blue Stain Kit. Gels were dried using Invitrogen Gel-Dry drying solution.

h) Light Microscopy

Crystals were observed using a Zeiss Axiovert 25 or a Nikon Labophot microscope. The latter was equipped with a polarization filter set and a JVC TK C1380 color video camera.

i) Assessment of Approximate Crystal Sizes

Using a Nikon Labophot microscope and the JVC Digital Screen Measurement Comet software version 3.52a, approximate crystal sizes were determined.

k) SE-HPLC

Aggregation levels of MAK195F samples were assessed by SE-HPLC. Dionex P680 pump, ASI-100 autosampler and UVD170U detector devices were used. Aggregated species were separated from the monomer by two serial Amersham Bioscience Agarose 12 10/300 GL gel filtration columns, applying a validated Abbott standard protocol (Afelimomab™—Drug Substance).

Unless otherwise indicated the above identified general procedures may be replaced by any other equivalent procedure within the level of skill in the art.

C. Vapor Diffusion Crystallization Experiments

Concentration values given in the following examples are initial values referring to the antibody solution and the reservoir solution before mixing of the two solutions.

All pH values, if not described otherwise, refer to the pH of a buffer stock (acetate or citrate buffer) before it was combined with other substances, such as the crystallization agent.

All buffer molarities, if not described otherwise, refer to sodium acetate/sodium citrate concentrations in a stock solution before pH adjustment, typically performed using acetic acid glacial or citric acid.

Example 1

Initial Screening of Conditions in Vapor Diffusion Mode

MAK195F was buffered into a 20 mM HEPES/150 mM sodium chloride buffer at pH 7.4. The protein concentration was adjusted to 10 mg/mL. Using the Hydra II crystallization robot, 96 well Greiner plates were set up at ambient temperature, using several commercially available crystallization screens. The protein solution and the crystallization agent were mixed in a ratio of 1:1. Following screens were used: Hampton Crystal Screen 1 & 2 (Hampton Research), Wizard Screen I & II (Emerald BioStructures), Hampton Index Screen (Hampton Research), Jena Screens 1-8 (Jena Bioscience). After addition of protein to a crystallization agent well known in the art (one drop per condition), the plates were sealed with Clearseal film and stored at ambient temperature. Microscopy of the drops was performed multiple times during the following seven days. The conditions were classified into clear drops, drops containing random precipitation, drops containing crystals and drops containing mixtures of precipitated species and crystals.

Results:

From the 480 conditions tested, crystals were observed in 11. The conditions comprised the following crystallization agents as declared by the manufacturers:

0.1 M sodium Cacodylate pH 6.5, 0.2 M calcium acetate, 18% w/v PEG 8,000
(Hampton Crystal Screen, D10)
0.1 M MES pH 6.5, 12% w/v PEG 20,000
(Hampton Crystal Screen, F10)
0.1 M citrate, pH 5.5, 20% w/v PEG 3,000
(Wizard Screen I & II, A6)
0.1 M acetate, pH 4.5, 20% w/v PEG 3,000
(Wizard Screen I & II, D9)
0.1 M Bis-Tris pH 6.5, 45% v/v Polypropylene Glycol P 400
(Hampton Index, E10)
0.1 M HEPES pH 7.5, 0.02 M magnesium chloride, 22% w/v Polyacrylic acid 5,100 sodium salt
(Hampton Index, E11)
0.1 M Tris pH 8.5, 0.2 M Trimethylamine N-oxide dihydrate, 20% w/v PEG MME 2000 (Hampton Index, F2)
0.2 M sodium citrate dihydrate, 20% w/v PEG 3,350
(Hampton Index, H10)
10% PEG 4,000, 0.1 M sodium HEPES pH 7.5, 20% isopropanol
(JENA 1-4, E5)
15% PEG 4,000, 0.1 M sodium citrate pH 5.6, 0.2 M ammonium sulfate
(JENA 1-4, F2)
20% PEG 4,000, 0.1 M sodium citrate pH 5.6, 0.2 M ammonium sulfate
(JENA 1-4, G6)

The crystals showed needle like morphologies with lengths of around 10 to 150 µm.

Example 2

Hanging Drop Vapor Diffusion Using Hampton PEG/Ion Screen

MAK195F was buffered into a 20 mM HEPES/150 mM sodium chloride buffer at pH 7.4. The protein concentration was adjusted to 10 mg/mL. Greased VDX plates and circular siliconized glass cover slides were used. 1 mL of each of the 48 buffer formulations was pipetted into a well. Around 1 µL of protein sample was pipetted onto a cover slide and subsequently mixed with around 1 µL of reservoir solution of a particular well. The well was sealed with the inverted cover slide, generating a hanging drop experiment. The plates were stored at ambient temperature. Microscopy of the drops was performed multiple times during the following seven days. The conditions were classified into clear drops, drops containing random precipitation, drops containing crystals and drops containing mixtures of precipitated species and crystals.

Results:

From the 48 conditions tested, crystals were observed in one. The condition comprised following crystallization agent as declared by the manufacturer:

0.2 M tri-Potassium citrate monohydrate, 20% w/v PEG 3,350 pH 8.3

The crystals showed needle cluster like morphology with dimensions of around 10 to 50 µm.

Example 3

Hanging Drop Vapor Diffusion Using Hampton Low Ionic Strength Screen

MAK195F was buffered into a 20 mM HEPES/150 mM sodium chloride buffer at pH 7.4. The protein concentration was adjusted to 10 mg/mL. Greased VDX plates and circular siliconized glass cover slides were used. 1 mL of 24% w/v PEG 3,350 dehydrant solution was pipetted into 108 wells. Around 2 µL of protein sample were pipetted onto a cover slide and subsequently mixed with around 1 µL of one of the 18 particular buffer reagents. Thereafter, around 2.5 µL of PEG 3,350 precipitant of one of six different concentrations was added to the drop. The wells were sealed with the inverted cover slides, generating 108 different hanging drop experiments. The plates were stored at ambient temperature. Microscopy of the drops was performed multiple times during the following seven days. The conditions were classified into clear drops, drops containing random precipitation, drops containing crystals and drops containing mixtures of precipitated species and crystals.

Results:

Crystals were not observed in any of the 108 conditions tested.

Example 4

PEG 4,000/Sodium Citrate Grid Screen in Hanging Drop Vapor Diffusion Mode

MAK195F was buffered into a 20 mM HEPES/150 mM sodium chloride buffer at pH 7.4. The protein concentration was adjusted to 10 mg/mL. A greased VDX plate and circular siliconized glass cover slides were used. 1 mL of a particular reservoir solution was prepared by mixing citrate buffer, 50% w/v PEG 4,000 solution and Milli Q water (fully desalted and optionally pre-distilled) in each well. In this example, citrate buffer molarity was kept constant at around 0.1 M, and the PEG 4,000 concentration was kept constant at around 20% w/v. The pH was varied from around 4.2 to around 6.5 in 0.1 steps, generating 24 different conditions. Around 1 µL of protein solution was mixed with around 1 µL of a particular reservoir solution on a circular siliconized glass cover slide, and the well was sealed with the inverted slide, generating a hanging drop experiment. The plates were stored at ambient temperature. Microscopy of the drops was performed after storage overnight. The conditions were classified into clear drops, drops containing random precipitation, drops containing crystals and drops containing mixtures of precipitated species and crystals.

Results:

Crystals were not observed in any of the 24 conditions tested after storage overnight.

Example 5

PEG 4,000/Sodium Citrate Grid Screen in Hanging Drop Vapor Diffusion Mode, Different Set Up MAK195F was buffered into a 20 mM HEPES/150 mM sodium chloride buffer at pH 7.4. The protein concentration was adjusted to 10 mg/mL. A greased VDX plate and circular siliconized glass cover slides were used. 1 mL of a particular reservoir solution was prepared by mixing citrate buffer, 50% w/v PEG 4,000 solution and Milli Q water in each well. In this example, the citrate buffer molarity was kept constant at around 0.1 M, and PEG 4,000 was applied at concentrations of around 10% w/v, 15% w/v, 20% w/v and 25% w/v. The pH was varied from around 5.0 to around 6.5 in 0.3 steps, generating 24 different conditions. Around 1 µL of protein solution was mixed with around 1 µL of a particular reservoir solution on a circular siliconized glass cover slide, and the well was sealed with the inverted slide, generating a hanging drop experiment. The plates were stored at ambient temperature. Microscopy of the drops was performed after storage overnight. The conditions were classified into clear drops, drops containing random precipitation, drops containing crystals and drops containing mixtures of precipitated species and crystals.

Results:

Crystals were not observed in any of the 24 conditions tested after storage overnight.

Example 6

PEG 4,000/Sodium Acetate Grid Screen in Hanging Drop Vapor Diffusion Mode

MAK195F was buffered into a 20 mM HEPES/150 mM sodium chloride buffer at pH 7.4. The protein concentration was adjusted to 10 mg/mL. A greased VDX plate and circular siliconized glass cover slides were used. 1 mL of a particular reservoir solution was prepared by mixing acetate buffer, 50% w/v PEG 4,000 solution and Milli Q water in each well. In this example, the acetate buffer molarity was kept constant at around 0.1 M, and PEG 4,000 concentration was kept constant at around 20% w/v. The pH was varied from around 3.6 to around 5.6 in 0.1 steps, generating 21 different conditions. Around 1 µL of protein solution was mixed with around 1 µL of a particular reservoir solution on a circular siliconized glass cover slide, and the well was sealed with the inverted slide, generating a hanging drop experiment. The plates were stored at ambient temperature. Microscopy of the drops was performed multiple times during the following seven days. The conditions were classified into clear drops, drops containing random precipitation, drops containing crystals and drops containing mixtures of precipitated species and crystals.

Results:

From the 21 conditions tested, crystals were observed at pH around 4.9, 5.0, 5.3 and 5.6, respectively. The crystals showed needle or needle cluster like morphology with dimensions of around 30 to 300 µm.

Example 7

PEG 4,000/Sodium Acetate Grid Screen in Hanging Drop Vapor Diffusion Mode, Different Set Up MAK195F was buffered into a 20 mM HEPES/150 mM sodium chloride buffer at pH 7.4. The protein concentration was adjusted to 10 mg/mL. A greased VDX plate and circular siliconized glass cover slides were used. 1 mL of a particular reservoir solution was prepared by mixing acetate buffer, 50% w/v PEG 4,000 solution and Milli Q water in each well. In this example, the acetate buffer molarity was kept constant at around 0.1 M, and PEG 4,000 was applied at concentrations of around 10% w/v, 15% w/v, 25% w/v, 30% w/v, 35% w/v and 40% w/v. The pH was around 3.9, 4.2, 4.8 and 5.1, generating 24 different conditions. Around 1 µL of protein solution was mixed with around 1 µL of a particular reservoir solution on a circular siliconized glass cover slide, and the well was sealed with the inverted slide, generating a hanging drop experiment. The plates were stored at ambient temperature. Microscopy of the drops was performed multiple times during the following seven days. The conditions were classified into clear drops, drops containing random precipitation, drops containing crystals and drops containing mixtures of precipitated species and crystals.

Results:

From the 24 conditions tested, crystals were observed at pH around 5.1 and a PEG 4,000 concentration of around 15% w/v. The crystals showed needle like morphology with lengths of around 50 to 150 µm.

Example 8

PEG 4,000/Sodium Acetate Grid Screen in Hanging Drop Vapor Diffusion Mode, Different Set Up MAK195F was buffered into a 20 mM HEPES/150 mM sodium chloride buffer at pH 7.4. The protein concentration was adjusted to 10 mg/mL. A greased VDX plate and square OptiClear plastic cover slides were used. 500 µL of a particular reservoir solution was pre-pared by mixing acetate buffer, 50% w/v PEG 4,000 solution and Milli Q water in each well. In this example, the acetate buffer molarity was kept constant at around 0.1 M, and the PEG 4,000 concentration was kept constant at around 20% w/v. The pH was varied from around 4.2 to around 6.5 in 0.1 steps, generating 24 different conditions. Around 1 µL of protein solution was mixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following twenty-one days. The conditions were classified into clear drops, drops containing random precipitation, drops containing crystals and drops containing mixtures of precipitated species and crystals.

Results:

From the 24 conditions tested, crystals were observed at pH around 4.6, 4.8, 4.9, 5.1, 5.2, 5.5 and 5.7. The crystals showed needle or needle cluster like morphology.

Example 9

PEG 4,000/Sodium Acetate Grid Screen in Hanging Drop Vapor Diffusion Mode, Different Set Up MAK195F was buffered into a 20 mM HEPES/150 mM sodium chloride buffer at pH 7.4. The protein concentration was adjusted to 10 mg/mL. A greased VDX plate and square OptiClear plastic cover slides were used. 500 µL of a particular reservoir solution was prepared by mixing acetate buffer, 50% w/v PEG 4,000 solution and Milli Q water in each well. In this example, the acetate buffer molarity was kept constant at around 0.1 M, and the PEG 4,000 was applied at concentrations of around 16% w/v, 18% w/v, 22% w/v and 24% w/v. The pH was around 4.2, 4.7, 5.2, 5.7, 6.2 and 6.5, generating 24 different conditions. Around 1 µL of protein solution was mixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following twenty-one days. The conditions were classified into clear drops, drops containing random precipitation, drops containing crystals and drops containing mixtures of precipitated species and crystals.

Results:

From the 24 conditions tested, crystals were observed at pH around 6.2 and PEG 4,000 concentrations of around 18%, 22% and 24% w/v. The crystals showed needle or needle cluster like morphology.

Example 10

PEG 4,000/Sodium Acetate Grid Screen in Hanging Drop Vapor Diffusion Mode, Different Set Up MAK195F was buffered into a 20 mM HEPES/150 mM sodium chloride buffer at pH 7.4. The protein concentration was adjusted to 10 mg/mL. A greased VDX plate and square OptiClear plastic cover slides were used. 500 µL of a particular reservoir solution was pre-pared by mixing acetate buffer, 50% w/v PEG 4,000 solution and Milli Q water in each well. In this example, the acetate buffer molarity was kept constant at around 0.1 M, and the buffer pH was kept constant at around 5.7. PEG 4,000 was applied at concentrations of around 10% w/v, 12% w/v, 14% w/v, 16% w/v, 18% w/v and 20% w/v. Hereby, six different conditions were assessed in quadruplicate. Around 1 µL of protein solution was mixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following twenty-one days. The conditions were classified into clear drops, drops containing random precipitation, drops containing crystals and drops containing mixtures of precipitated species and crystals.

Results:

From the 6 conditions tested, crystals were observed at all PEG 4,000 concentrations. Crystals were observed in one to four wells of a quadruplicated experiment.

The crystals showed needle or needle cluster like morphology.

Example 11

PEG 4,000/Sodium Acetate Grid Screen in Hanging Drop Vapor Diffusion Mode, Different Set Up MAK195F was buffered into a 20 mM HEPES/150 mM sodium chloride buffer at pH 7.4. The protein concentration was adjusted to 10 mg/mL. A greased VDX plate and square OptiClear plastic cover slides were used. 500 µL of a particular reservoir solution was pre-pared by mixing acetate buffer, 50% w/v PEG 4,000 solution and Milli Q water in each well. In this example, the acetate buffer molarity was kept constant at around 0.1 M, and the PEG 4,000 was applied at concentrations of around 8% w/v, 10% w/v, 12% w/v and 14% w/v. The pH was around 4.2, 4.7, 5.2, 5.7, 6.2 and 6.5, generating 24 different conditions. Around 1 µL of protein solution was mixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following twenty-one days. The conditions were classified into clear drops, drops containing random precipitation, drops containing crystals and drops containing mixtures of precipitated species and crystals.

Results:

From the 24 conditions tested, crystals were observed at pH around 4.7 and PEG 4,000 concentrations of around 8% w/v, 10% w/v and 12 w/v. Furthermore, crystals were observed at pH around 5.2 and PEG 4,000 concentrations of around 12% w/v and 14% w/v. Furthermore, crystals were observed at pH around 5.7 and PEG 4,000 concentrations of around 10% w/v, 12% w/v and 14% w/v. Furthermore, crystals were observed at pH around 6.2 and PEG 4,000 concentrations of around 10% w/v and 14% w/v. Furthermore, crystals were observed at pH around 6.5 and PEG 4,000 concentrations of around 8% w/v and 12% w/v. The crystals showed needle or needle cluster like morphology.

Example 12

PEG 4,000/Sodium Citrate Grid Screen in Hanging Drop Vapor Diffusion Mode, Different Set Up MAK195F was buffered into a 20 mM HEPES/150 mM sodium chloride buffer at pH 7.4. The protein concentration was adjusted to 10 mg/mL. A greased VDX plate and square OptiClear plastic cover slides were used. 500 µL of a particular reservoir solution was pre-pared by mixing citrate buffer, 50% w/v PEG 4,000 solution and Milli Q water in each well. In this example, the citrate buffer molarity was kept constant at around 0.1 M, and the PEG 4,000 concentration was kept constant at around 20% w/v. The pH was varied from around 4.2 to around 6.5 in 0.1 pH unit steps, generating 24 different conditions. Around 1 µL of protein solution was mixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following nine days. The conditions were classified into clear drops, drops containing random precipitation, drops containing crystals and drops containing mixtures of precipitated species and crystals.

Results:

From the 24 conditions tested, crystals were observed at pH around 5.1 through 6.5. The crystals showed needle or needle cluster like morphology.

Example 13

PEG 4,000/Sodium Citrate Grid Screen in Hanging Drop Vapor Diffusion Mode, Different Set Up MAK195F was buffered into a 20 mM HEPES/150 mM sodium chloride buffer at pH 7.4. The protein concentration was adjusted to 10 mg/mL. A greased VDX plate and square OptiClear plastic cover slides were used. 500 μL of a particular reservoir solution was pre-pared by mixing citrate buffer, 50% w/v PEG 4,000 solution and Milli Q water in each well. In this example, the citrate buffer molarity was kept constant at around 0.1 M, and the PEG 4,000 was applied at concentrations of around 16% w/v, 18% w/v, 22% w/v and 24% w/v. The pH was varied from around 4.2 to around 6.5 in 0.5 pH unit steps, generating 24 different conditions. Around 1 μL of protein solution was mixed with around 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following nine days. The conditions were classified into clear drops, drops containing random precipitation, drops containing crystals and drops containing mixtures of precipitated species and crystals.

Results:

From the 24 conditions tested, crystals were observed at pH around 4.7 and a PEG 4,000 concentration of around 16% w/v. Furthermore, crystals were observed at pH around 5.2 and PEG 4,000 concentrations of around 16% w/v and 18% w/v. Furthermore, crystals were observed at pH around 5.7 and PEG 4,000 concentrations of around 16% w/v, 18% w/v, 22% w/v and 24% w/v. Furthermore, crystals were observed at pH around 6.2 and PEG 4,000 concentrations of around 10% w/v and 14% w/v. Furthermore, crystals were observed at pH around 6.5 and a PEG 4,000 concentration of around 16% w/v. The crystals showed needle or needle cluster like morphology.

Example 14

PEG 4,000/Sodium Citrate Grid Screen in Hanging Drop Vapor Diffusion Mode, Different Protein Buffer MAK195F used in its standard drug substance buffer (12.39 mg/mL MAK195F in 10 mM sodium phosphate, 150 mM sodium chloride, 0.01% Pluronic F 68, pH 7.2). Buffer composition as declared from Abbott was 12.4 mg/mL MAK195F in 10 mM sodium phosphate, 150 mM sodium chloride, 0.01% Pluronic F 68, pH 7.2. A greased VDX plate and square OptiClear plastic cover slides were used. 500 μL of a particular reservoir solution was pre-pared by mixing citrate buffer, 50% w/v PEG 4,000 solution and Milli Q water in each well. In this example, the citrate buffer molarity was kept constant at around 0.1 M, and PEG 4,000 was kept constant at a concentration of around 20% w/v. The pH was varied from around 4.2 to around 6.5 in 0.1 pH unit steps, generating 24 different conditions. Around 1 μL of protein solution was mixed with around 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following six days. The conditions were classified into clear drops, drops containing random precipitation, drops containing crystals and drops containing mixtures of precipitated species and crystals.

Results:

From the 24 conditions tested, crystals were observed at a pH range of around 5.3 to around 5.9. The crystals showed needle or needle cluster like morphology.

Example 15

PEG 4,000/Sodium Citrate Grid Screen in Hanging Drop Vapor Diffusion Mode, Different Protein Buffer MAK195F used in its standard drug substance buffer (12.39 mg/mL MAK195F in 10 mM sodium phosphate, 150 mM sodium chloride, 0.01% Pluronic F 68, pH 7.2). A greased VDX plate and square OptiClear plastic cover slides were used. 500 μL of a particular reservoir solution was prepared by mixing citrate buffer, 50% w/v PEG 4,000 solution and Milli Q water in each well. In this example, the citrate buffer molarity was kept constant at around 0.1 M, and PEG 4,000 was applied at concentrations of around 16% w/v, 18% w/v, 22% w/v and 24% w/v. The pH was varied from around 4.2 to around 6.5 in 0.5 pH unit steps, generating 24 different conditions. Around 1 μL of protein solution was mixed with around 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following six days. The conditions were classified into clear drops, drops containing random precipitation, drops containing crystals and drops containing mixtures of precipitated species and crystals.

Results:

From the 24 conditions tested, crystals were observed at a pH of around 5.7 and PEG 4,000 concentrations of around 16% w/v and 18% w/v. Furthermore, crystals were observed at a PEG 4,000 concentration of around 16% w/v and pH of around 6.2 and 6.5, respectively. The crystals showed needle or needle cluster like morphology.

Example 16

Zinc Acetate/Sodium Citrate Grid Screen in Hanging Drop Vapor Diffusion Mode

MAK195F was buffered into a 20 mM HEPES/150 mM sodium chloride buffer at pH 7.4. The protein concentration was adjusted to 10 mg/mL. A greased VDX plate and square OptiClear plastic cover slides were used. 500 μL of a particular reservoir solution was pre-pared by mixing citrate buffer, zinc acetate and Milli Q water in each well. In this example, the citrate buffer molarity was kept constant at around 0.1 M, and zinc acetate was used at concentrations of around 0.05 M, 0.1 M, 0.5 M and 0.9 M. The pH was varied from around 4.2 to around 6.5 in 0.5 pH unit steps, generating 24 different conditions. Around 1 μL of protein solution was mixed with around 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following twenty-one days. The conditions were classified into clear drops, drops containing random precipitation, drops containing crystals and drops containing mixtures of precipitated species and crystals.

Results:

Crystals were not observed in any of the 24 conditions tested.

Example 17

Mannitol/Sodium Citrate Grid Screen in Hanging Drop Vapor Diffusion Mode

MAK195F was buffered into a 20 mM HEPES/150 mM sodium chloride buffer at pH 7.4. The protein concentration was adjusted to 10 mg/mL. A greased VDX plate and square OptiClear plastic cover slides were used. 500 µL of a particular reservoir solution was pre-pared by mixing citrate buffer, mannitol and Milli Q water in each well. In this example, the citrate buffer molarity was kept constant at around 0.1 M, and mannitol was used at concentrations of around 0.05 M, 0.1 M, 0.5 M and 0.9 M. The pH was varied from around 4.2 to around 6.5 in 0.5 pH unit steps, generating 24 different conditions. Around 1 µL of protein solution was mixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following six days. The conditions were classified into clear drops, drops containing random precipitation, drops containing crystals and drops containing mixtures of precipitated species and crystals.

Results:

Crystals were not observed in any of the 24 conditions tested.

Example 18

PEG 4,000/Sodium Acetate Grid Screen in Hanging Drop Vapor Diffusion Mode, Different Temperature MAK195F was buffered into a 20 mM HEPES/150 mM sodium chloride buffer at pH 7.4. The protein concentration was adjusted to 10 mg/mL. A greased VDX plate and square OptiClear plastic cover slides were used. 500 µL of a particular reservoir solution was pre-pared by mixing acetate buffer, 50% w/v PEG 4,000 solution and Milli Q water in each well. In this example, the acetate buffer molarity was kept constant at around 0.1 M, and PEG 4,000 was applied at concentrations of around 10% w/v, 12% w/v, 18% w/v and 20% w/v. The pH was around 5.6 throughout. Around 1 µL of protein solution was mixed with around 1 µL of a particular reservoir solution on a square OptiClear plastic cover slide, and the well was sealed with the inverted slide, generating a hanging drop experiment. The plate was stored at 4° C. Microscopy of the drops was performed after storage overnight. The conditions were classified into clear drops, drops containing random precipitation, drops containing crystals and drops containing mixtures of precipitated species and crystals. As positive control, a second plate was set up with equal conditions and stored at ambient temperature.

Results:

Crystals were not observed in any of the 24 conditions tested after storage at 4° C. overnight. The positive control contained crystals at PEG 4,000 concentrations of 10% w/v, 12% w/v and 18% w/v.

Example 19

PEG 4,000/Sodium Acetate Grid Screen in Hanging Drop Vapor Diffusion Mode, Different Protein Buffer MAK195F was exchanged into a buffer containing around 0.1M sodium acetate at a pH of around 5.5. The protein concentration was adjusted to 10 mg/mL. A greased VDX plate and square OptiClear plastic cover slides were used. 500 µL of a particular reservoir solution was prepared by mixing acetate buffer, 50% w/v PEG 4,000 solution and Milli Q water in each well. In this example, the acetate buffer molarity was kept constant at around 0.1 M, and the PEG 4,000 concentration was varied from around 12% w/v to around 26% w/v in 2% steps. The pH was around 5.5 throughout. Each condition was assessed in triplicate. Around 1 µL of protein solution was mixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following fourteen days. The conditions were classified into clear drops, drops containing random precipitation, drops containing crystals and drops containing mixtures of precipitated species and crystals.

Results:

From the 24 wells assessed, crystals were observed at all PEG 4,000 concentrations tested. The crystals showed needle or needle cluster like morphology.

D1. Batch Experiments with a Volume Up to 1 mL

Concentration values given in the following examples are initial values referring to the antibody solution and the crystallization solution before mixing of the two solutions.

All pH values, if not described otherwise, refer to the pH of a buffer stock (acetate or citrate buffer) before it was combined with other substances, like the crystallization agent.

All buffer molarities, if not described otherwise, refer to sodium acetate or sodium citrate concentrations in a stock solution before pH adjustment, typically performed using acetic acid glacial or citric acid.

Example 20

PEG 4,000/Sodium Acetate Grid Screen in 50 µL Volume Batch Mode

MAK195F was buffered into a 20 mM HEPES/150 mM sodium chloride buffer at pH 7.4. The protein concentration was adjusted to 10 mg/mL. Batch crystallization was performed by admixing around 25 µL of protein solution with an equal amount of crystallization solution in a well. The well plate was subsequently sealed with adhesive tape to prevent water evaporation. 25 µL of a particular crystallization solution were prepared by admixing acetate buffer, 50% w/v PEG 4,000 solution and Milli Q water in each well. In this example, the acetate buffer molarity was kept constant at around 0.05 M, and acetate buffer pH was around 5.7 throughout. The PEG 4,000 concentration was varied from around 12% w/v to around 4% w/v in 1% steps. Each condition was assessed in duplicate. The plate was stored at ambient temperature. Microscopy of the wells was performed after three days. The conditions were classified into clear drops, drops containing random precipitation, drops containing crystals and drops containing mixtures of precipitated species and crystals.

Results:
Crystals were not observed in any of the 18 conditions tested after 3 days.

Example 21

PEG 4,000/Sodium Acetate Grid Screen in 50 μL Volume Batch Mode, Different Set Up MAK195F was buffered into a 20 mM HEPES/150 mM sodium chloride buffer at pH 7.4. The protein concentration was adjusted to 10 mg/mL. Batch crystallization was performed by admixing around 25 μL of protein solution with an equal amount of crystallization solution in a well. The well plate was subsequently sealed with adhesive tape to prevent water evaporation. 25 μL of a particular crystallization solution were prepared by admixing acetate buffer, 50% w/v PEG 4,000 solution and Milli Q water in each well. In this example, the acetate buffer molarity was kept constant at around 0.1 M, and acetate buffer pH was around 5.7 throughout. The PEG 4,000 concentration was varied from around 14% w/v to around 36% w/v in 2% steps. Each condition was assessed in duplicate. The plate was stored at ambient temperature. Microscopy of the wells was performed multiple times during the following seven days. The conditions were classified into clear drops, drops containing random precipitation, drops containing crystals and drops containing mixtures of precipitated species and crystals.
Results:
From the 18 wells observed, crystals were observed in the conditions, which were set up with between 22% w/v and 16% w/v PEG 4,000.

Example 22

PEG 4,000/Sodium Acetate Grid Screen in 300 μL Volume Batch Mode

MAK195F was buffered into a 20 mM HEPES/150 mM sodium chloride buffer at pH 7.4. The protein concentration was adjusted to 10 mg/mL. Batch crystallization was performed by admixing around 150 μL of protein solution with an equal amount of crystallization solution in a well. The well plate was subsequently sealed with adhesive tape to prevent water evaporation. 150 μL of a particular crystallization solution were prepared by admixing acetate buffer, 50% w/v PEG 4,000 solution and Milli Q water in each well. In this example, the acetate buffer molarity was kept constant at around 0.1 M, and acetate buffer pH was around 5.7 throughout. The PEG 4,000 concentration was varied from around 18% w/v to around 24% w/v in 2% steps. Each condition was assessed in duplicate. The plate was stored at ambient temperature. Microscopy of the drops was performed multiple times during the following fourteen days. The conditions were classified into clear drops, drops containing random precipitation, drops containing crystals and drops containing mixtures of precipitated species and crystals.
Results:
From the 8 wells observed, crystals were observed in all conditions tested. In the 20% w/v PEG 4,000 batches, no precipitation besides crystallized species could be observed Example 23

PEG 4,000/Sodium Acetate Grid Screen in 300 μL Volume Batch Mode, Different Protein Buffer MAK195F used in its standard drug substance buffer (12.39 mg/mL MAK195F in 10 mM sodium phosphate, 150 mM sodium chloride, 0.01% Pluronic F 68, pH 7.2). Batch crystallization was performed by admixing around 150 μL of protein solution with an equal amount of crystallization solution in a well. The well plate was subsequently sealed with adhesive tape to prevent water evaporation. 150 μL of a particular crystallization solution were prepared by admixing acetate buffer, 50% w/v PEG 4,000 solution and Milli Q water in each well. In this example, the acetate buffer molarity was kept constant at around 0.1 M, and the acetate buffer pH was around 5.7 throughout. The PEG 4,000 concentration was varied from around 18% w/v to around 24% w/v in 2% steps. Each condition was assessed once. The plate was stored at ambient temperature. Microscopy of the drops was performed multiple times during the following fourteen days. The conditions were classified into clear drops, drops containing random precipitation, drops containing crystals and drops containing mixtures of precipitated species and crystals.
Results:
From the 4 wells observed, crystals were observed in all conditions tested.

Example 24

PEG 4,000/Sodium Acetate and Sodium Citrate Grid Screen in 150 μL Volume Batch Mode, Finding of Lead Conditions for Scaling Up Beyond 1 mL MAK195F was buffered into a 20 mM HEPES/150 mM sodium chloride buffer at pH 7.4. The protein concentration was adjusted to 10 mg/mL. Batch crystallization was performed by admixing around 75 μL of protein solution with an equal amount of crystallization solution in a well. The well plate was subsequently sealed with adhesive tape to prevent water evaporation. 75 μL of a particular crystallization solution were prepared by admixing acetate or citrate buffer, 50% w/v PEG 4,000 solution and Milli Q water in each well. In this example, the buffer molarity was kept constant at around 0.1 M, and the buffer pH was around 4.2, 4.7, 5.2, 5.7 and 6.2. The PEG 4,000 concentration was varied from around 6% w/v to around 28% w/v in 2% steps. Each condition was assessed in triplicate. The plates were stored at ambient temperature. Microscopy of the drops was performed after 1, 2, 3 and 7 days, respectively. The conditions were classified into clear drops, drops containing random precipitation, drops containing crystals and drops containing mixtures of precipitated species and crystals. Also, the yield of particulate matter was determined from two of the three wells of one condition by OD280. 100 μL aliquots were centrifuged at 14,000×g, and the protein concentration in the supernatant was assessed.
Results:
By varying PEG 4,000 concentration from around 6% w/v to around 28% w/v, the appearance of the crystal mixture varied from clear (low PEG concentrations) through needle or needle cluster like crystals (medium PEG concentrations) to precipitation (high PEG concentration levels). The appearance of crystallization windows was also dependent on the buffer composition (pH, ionic strength, salt). No crystals were observed with an acetate buffer and a pH of 6.2, nor with a citrate buffer at pH 4.2 and 6.2. All other buffer systems showed crystallization windows at a characteristic PEG 4,000 concentration. These results indicated that possible crystallization conditions are spread through the matrix created by using the applied chemicals, and that it is possible to choose a buffer composition that yields crystals without concomitant precipitation.

Example 25

PEG 4,000/Sodium Acetate Grid Screen in 1 mL Volume Batch Mode

MAK195F was buffered into a 20 mM HEPES/150 mM sodium chloride buffer at pH 7.4. The protein concentration was adjusted to 10 mg/mL. Batch crystallization was performed by admixing around 500 µL of protein solution with an equal amount of crystallization solution in a 1.5 mL Eppendorf reaction tube. 500 µL of a particular crystallization solution were prepared by admixing acetate buffer, 50% w/v PEG 4,000 solution and Milli Q water in the tube. In this example, the acetate buffer molarity was kept constant at around 0.1 M, and the acetate buffer pH was around 4.7 or 5.2. PEG 4,000 was applied at two concentrations, 16% w/v and 18% w/v. Each condition was assessed in duplicate. The tubes were stored at ambient temperature. Microscopy of a 1 µL aliquot of each tube was performed multiple times during the following month. The conditions were classified into clear drops, drops containing random precipitation, drops containing crystals and drops containing mixtures of precipitated species and crystals.

Results:

After 14 days, needles were observed in all conditions tested.

Example 26

PEG 4,000/Sodium Acetate Grid Screen in 150 µL Volume Batch Mode, Different Protein Buffer MAK195F was exchanged into a buffer containing around 0.1 M sodium acetate at a pH of around 5.5. The protein concentration was adjusted to 10 mg/mL. Batch crystallization was performed by admixing around 75 µL of protein solution with an equal amount of crystallization solution in a well. The well plate was subsequently sealed with adhesive tape to pre-vent water evaporation. 75 µL of a particular crystallization solution were prepared by admixing acetate buffer, 50% w/v PEG 4,000 solution and Milli Q water in each well. In this example, the acetate buffer molarity was kept constant at around 0.1 M, and the acetate buffer pH was around 5.5 throughout. PEG 4,000 was used at a concentration of 18% w/v and 20% w/v. Each condition was assessed in duplicate. The plate was stored at ambient temperature. Microscopy of the wells was performed multiple times during the following twelve days. The conditions were classified into clear drops, drops containing random precipitation, drops containing crystals and drops containing mixtures of precipitated species and crystals.

Results:

Crystals in needle or needle cluster like morphology were observed for both conditions.

Example 27

PEG 4,000/Sodium Acetate Grid Screen in 1 mL Volume Batch Mode, Different Protein Buffer MAK195F was exchanged into a buffer containing around 0.1 M sodium acetate at a pH of around 5.0 or 5.5. The protein concentration was adjusted to 10 mg/mL. Batch crystallization was performed by admixing around 500 µL of protein solution with an equal amount of crystallization solution in a well. The well plate was subsequently sealed with adhesive tape to prevent water evaporation. 500 µL of a particular crystallization solution were prepared by admixing acetate buffer, 50% w/v PEG 4,000 solution and Milli Q water in each well. In this example, the acetate buffer molarity was kept constant at around 0.1 M, and the acetate buffer pH was around 5.0 or 5.5 throughout. The protein buffered to pH 5.5 was admixed with a crystallization solution at pH 5.5, and the same was done with the protein buffered at pH 5.0. PEG 4,000 was used at concentrations of around 16% w/v to 24% w/v, varied in 2% steps. Each condition was assessed in triplicate. The plate was stored at ambient temperature. Microscopy of the wells was performed multiple times during the following month. The conditions were classified into clear drops, drops containing random precipitation, drops containing crystals and drops containing mixtures of precipitated species and crystals.

Results:

Crystals in the shape of needles or needle like clusters were observed in all conditions tested.

Example 28

PEG 4,000/Sodium Acetate Grid Screen in 1 mL Volume Batch Mode, Different Set Up MAK195F was exchanged into a buffer containing around 0.1 M sodium acetate at a pH of around 5.0 or 5.5. The protein concentration was adjusted to 10 mg/mL. Batch crystallization was performed by admixing around 500 µL of protein solution with an equal amount of crystallization solution in a well. The well plate was subsequently sealed with adhesive tape to prevent water evaporation. 500 µL of a particular crystallization solution were pre-pared by admixing distilled water and 50% w/v PEG 4,000 solution in each well. In this example, the acetate buffer molarity was 0 M, i.e., the only acetate buffer in the experiment was that in the original MAK195F solution. PEG 4,000 was used at concentrations of around 22% w/v to 26% w/v, varied in steps of 2%. The plate was stored at ambient temperature. Microscopy of the wells was performed multiple times during the following month. The conditions were classified into clear drops, drops containing random precipitation, drops containing crystals and drops containing mixtures of precipitated species and crystals.

Results:

Crystals in the form of needles or needle like clusters were observed in the well containing 22% w/v PEG 4,000 and the protein in the pH 5.5 buffer.

Example 29

PEG 4,000/Sodium Acetate Crystallization Condition at 1 mL Batch Volume, Influence of Polysorbate 80 Addition MAK195F was exchanged into a buffer containing around 0.1 M sodium acetate at a pH of around 5.5. The protein concentration was adjusted to 10 mg/mL. Polysorbate 80 was added to the protein solution in concentrations of around 1%, 0.1%, 0.01%, and 0.001%. A polysorbate 80 free solution was set up as control. The solutions were incubated overnight before setting up crystallization experiments. Batch crystallization was performed by admixing around 500 µL of protein solution with an equal amount of crystallization solution in a 1.5 mL Eppendorf reaction tube. 500 µL of the crystallization solution were prepared by admixing acetate buffer, 50% w/v PEG 4,000 solution and Milli Q water in the tube. In this example, the acetate buffer molarity was around 0.1 M, and the acetate buffer pH was around 5.5. PEG 4,000 was used at a concentration of 20% w/v. Each polysorbate 80 concentration was assessed in duplicate. The tubes were stored at ambient temperature. Microscopy of 1 µL aliquots of the solutions was performed multiple times during the following month.

Results:

Needle like crystals appeared after five days in all containers. No difference could be observed in the crystal morphology, nor the crystal yield.

Example 30

PEG 4,000/Sodium Acetate Crystallization Condition at 100 µL Batch Volume, Influence of Different Minerals as Crystallization Nucleants MAK195F was exchanged into a buffer containing around 0.1 M sodium acetate at a pH of around 5.2. The protein concentration was adjusted to 10 mg/mL. A set of 49 different minerals (property of the "Mineralogische Staatssammlung München") was assessed as crystallization nucleants. The idea behind this experiment was to investigate the feasibility of using such minerals as surfaces for growth of polymorphic crystal forms different from the standard needle or needle cluster like morphology. Each mineral was freshly split, and a grain in the dimension of 50 to 250 µm was put into a well. Each mineral was investigated in duplicate, and a number of mineral-free wells was set up as control. Batch crystallization was performed by admixing around 50 µL of protein solution with an equal amount of crystallization solution in the well. 50 µL of the crystallization solution were prepared by admixing acetate buffer, 50% w/v PEG 4,000 solution and Milli Q water in the well. In this example, the acetate buffer molarity was around 0.1 M, and acetate buffer pH was around 5.2. PEG 4,000 was used at a concentration of around 16% w/v. Microscopy of the well plate was performed during the following two weeks.

Results:

It was found that malachite generated an oily looking precipitate of the protein.

D2. Batch Experiments with a Volume above 1 ML

Concentration values given in the following examples are initial values referring to the antibody solution and the crystallization solution before mixing of the two solutions.

All pH values, if not described otherwise, refer to the pH of a buffer stock (acetate or citrate buffer) before it was combined with other substances, like the crystallization agent.

All buffer molarities, if not described otherwise, refer to sodium acetate or sodium citrate concentrations in a stock solution before pH adjustment, typically performed using acetic acid glacial or citric acid.

Example 31

PEG 4,000/Sodium Acetate Crystallization Condition at 10 mL Batch Volume

MAK195F was buffered into a 20 mM HEPES/150 mM sodium chloride buffer at pH 7.4. The protein concentration was adjusted to 10 mg/mL. Batch crystallization was performed by admixing around 5 mL of protein solution with an equal amount of crystallization solution in a 50 mL Falcon tube. 5 mL of the crystallization solution were prepared by admixing acetate buffer, 50% w/v PEG 4,000 solution and Milli Q water in the tube. In this example, the acetate buffer molarity was around 0.1 M, and the acetate buffer pH was around 5.2. PEG 4,000 was used at a concentration of 18% w/v. The tube was stored at ambient temperature. Microscopy of a 1 µL aliquot of the solution was performed multiple times during the following months. Furthermore, the crystal yield was determined by OD280. An aliquot of the suspension was centrifuged at 14,000 rpm, and the protein concentration in the supernatant was assessed.

Results:

Needle like crystals in the length of around 100 to 300 µm appeared after storage overnight. No precipitated species were observed during the following month of storage. The crystal yield, as determined by OD280 from residual protein concentration in the supernatant, was between 60 and 80% after ten days.

Example 32

PEG 4,000/Sodium Acetate Crystallization Condition at 10 mL Batch Volume, Introduction of Agitation MAK195F was buffered into a 20 mM HEPES/150 mM sodium chloride buffer at pH 7.4. The protein concentration was adjusted to 10 mg/mL. Batch crystallization was performed by admixing around 5 mL of protein solution with an equal amount of crystallization solution in a 50 mL Falcon tube. 5 mL of the crystallization solution were prepared by admixing acetate buffer, 50% w/v PEG 4,000 solution and Milli Q water in the tube. In this example, the acetate buffer molarity was around 0.1 M, and acetate buffer pH was around 5.2. PEG 4,000 was used at a concentration of 18% w/v. The tube was stored at ambient temperature, agitating the batch on a laboratory shaker. Microscopy of a 1 µL aliquot of the solution was performed multiple times during the following months. Furthermore, the crystal yield was determined by OD280. An aliquot of the suspension was centrifuged at 14,000 rpm, and the protein concentration in the supernatant was assessed.

Results:

Tiny needle-like crystals around 10 to 30 µm in length appeared after one day. No precipitated species were observed during the experiment. The crystal yield, as determined by OD280 from residual protein concentration in the supernatant, was between 60 and 80% after ten days.

Example 33

PEG 4,000/Sodium Acetate Crystallization Condition at 10 mL Batch Volume, Different Protein Buffer MAK195F was exchanged into a buffer containing around 0.1 M sodium acetate at a pH of around 5.5. The protein concentration was adjusted 10 mg/mL. Batch crystallization was performed by admixing around 5 mL of protein solution with an equal amount of crystallization solution in a 50 mL Falcon tube. 5 mL of the crystallization solution were prepared by admixing acetate buffer, 50% w/v PEG 4,000 solution and Milli Q water in the tube. In this example, the acetate buffer molarity was around 0.1 M, and the acetate buffer pH was around 5.5. PEG 4,000 was used at a concentration of 20% w/v and 22% w/v. The tubes were stored at ambient temperature. Microscopy of a 1 µL aliquot of the solution was performed multiple times during the following month. Furthermore, the crystal yield was determined by OD280. An aliquot of the suspension was centrifuged at 14,000 rpm, and the protein concentration in the supernatant was assessed.

Results:

Needle-like crystals with a length of 100 to 300 µm appeared after two days at both PEG concentration levels. No precipitated species were observed during the following month of storage. The crystal yield, as determined by OD280 from residual protein concentration in the supernatant, was between 60 and 80% after ten days.

Example 34

PEG 4,000/Sodium Acetate Crystallization Condition at 10 mL Batch Volume, Different Protein Buffer and Comparison of Non Agitated and Agitated Batches MAK195F was exchanged into a buffer containing around 0.1 M sodium acetate at a pH of around 5.2. The protein concentration was adjusted to 10 mg/mL. Batch crystallization was performed by admixing around 5 mL of protein solution with an equal amount of crystallization solution in a 50 mL Falcon tube. 5 mL of the crystallization solution were prepared by admixing acetate buffer, 50% w/v PEG 4,000 solution and Milli Q water in the tube. In this example, the acetate buffer molarity was around 0.1 M, and the acetate buffer pH was around 5.2. PEG 4,000 was used at a concentration of 20% w/v. The tubes were stored at ambient temperature, one without agitation and one on a laboratory shaker. Microscopy of a 1 µL aliquot of the solutions was performed multiple times during the following twenty-one days. Furthermore, the crystal yield was determined by OD280. An aliquot of the suspension was centrifuged at 14,000 rpm, and the protein concentration in the supernatant was assessed.

Results:

Needle-like crystals appeared after seven days in both containers. Needles from the agitated batch were about one-tenth the length of the needles from the non-agitated batch. For the non-agitated batch, needle length was around 100 to 300 µm, whereas in the agitated batch the needles were around 10 to 30 µm long. The crystal yield, as determined by OD280 from residual protein concentration in the supernatant, was between 50 and 80% after ten days, in both containers.

Example 35

PEG 4,000/Sodium Acetate Crystallization Condition at 10 mL Batch Volume, Different Protein Buffer and Comparison of Non-Agitated and Agitated Batches MAK195F was exchanged into a buffer containing around 0.1 M sodium acetate at a pH of around 5.5. The protein concentration was adjusted to 10 mg/mL. Batch crystallization was performed by admixing around 5 mL of protein solution with an equal amount of crystallization solution in a 50 mL Falcon tube. 5 mL of the crystallization solution were prepared by admixing acetate buffer, 50% w/v PEG 4,000 solution and Milli Q water in the tube. In this example, the acetate buffer molarity was around 0.1 M, and the acetate buffer pH was around 5.5. PEG 4,000 was used at a concentration of 20% w/v. The tubes were stored at ambient temperature, one without agitation and one on a laboratory shaker. Microscopy of a 1 µL aliquot of the solutions was performed multiple times during the following twenty-one days. Furthermore, the crystal yield was determined by OD280. An aliquot of the suspension was centrifuged at 14,000 rpm, and the protein concentration in the supernatant was assessed.

Results:

Needle-like crystals appeared after seven days in both containers. Needles from the agitated batch were about one-tenth the length of the needles from the non-agitated batch. For the non-agitated batch, needle length was around 100 to 300 µm, whereas in the agitated batch the needles were around 10 to 30 µm long. The crystal yield, as determined by OD280 from residual protein concentration in the supernatant, was between 50 and 80% after ten days, in both containers.

Example 36

PEG 4,000/Sodium Acetate Crystallization Condition at 250 mL Batch Volume

MAK195F was exchanged into a buffer containing around 0.1 M sodium acetate at a pH of around 5.2. The protein concentration was adjusted to 10 mg/mL. Batch crystallization was performed by admixing around 125 mL of protein solution with an equal amount of crystallization solution in a 1 L polypropylene container. 125 mL of the crystallization solution were prepared by admixing acetate buffer, 50% w/v PEG 4,000 solution and Milli Q water in the tube. In this example, the acetate buffer molarity was around 0.1 M, and the acetate buffer pH was around 5.2. PEG 4,000 was used at a concentration of 20% w/v. The container was stored at ambient temperature. Agitation was performed by rolling the container at around 60 rpm. Microscopy of a 1 µL aliquot of the solution was performed multiple times during the following months. Furthermore, the crystal yield was determined by OD280. An aliquot of the suspension was centrifuged at 14,000 rpm, and the protein concentration in the supernatant was assessed.

Results:

Needle-like crystals with a length of around 10 to 30 µm appeared after three days. No precipitated species were observed during the following month of storage. The crystal yield, as determined by OD280 from residual protein concentration in the supernatant, was between 60 and 70% after seven days.

Example 37

PEG 4,000/Sodium Acetate Crystallization Condition at 10 mL Batch Volume, Different Container Material MAK195F was exchanged into a buffer containing around 0.1 M sodium acetate at a pH of around 5.2. The protein concentration was adjusted to 10 mg/mL. Batch crystallization was performed by admixing around 5 mL of protein solution with an equal amount of crystallization solution in a 50 mL glass (Class I) vial. 5 mL of the crystallization solution were pre-pared by admixing acetate buffer, 50% w/v PEG 4,000 solution and Milli Q water in the tube. In this example, the acetate buffer molarity was around 0.1 M, and the acetate buffer pH was around 5.2. PEG 4,000 was used at a concentration of 20% w/v. The vial was sealed with a teflonized stopper and stored at ambient temperature, being agitated on a laboratory shaker. Microscopy of a 1 µL aliquot of the solution was performed multiple times during the following twenty-one days.

Results: Needle like crystals appeared after three days.

Example 38

PEG 4,000/Sodium Acetate Crystallization Condition at 10 mL Batch Volume, Different Temperature MAK195F was exchanged into a buffer containing around 0.1 M sodium acetate at a pH of around 5.2. The protein concentration was adjusted to 10 mg/mL. Batch crystallization was performed by admixing around 5 mL of protein solution with an equal amount of crystallization solution in a 50 mL Falcon tube. 5 mL of the crystallization solution were prepared by admixing acetate buffer, 50% w/v PEG 4,000 solution and Milli Q water in the tube. In this example, the acetate buffer molarity was around 0.1 M, and the acetate buffer pH was around 5.2. PEG 4,000 was used at a concentration of 20% w/v. The tube was stored at 4° C., being agitated on a laboratory shaker. Microscopy of a 1 µL aliquot of the solution was performed multiple times during the following ten days. After ten days storage at 4° C., the batch was transferred to ambient temperature.
Results:
No crystals appeared during storage at 4° C. When the batch was transferred to ambient temperature, crystals appeared overnight.

Example 39

PEG 4,000/Sodium Acetate Crystallization Condition at 1 L Batch Volume

MAK195F was exchanged into a buffer containing around 0.1 M sodium acetate at a pH of around 5.2. The protein concentration was adjusted to 10 mg/mL. Batch crystallization was performed by admixing around 500 mL of protein solution with an equal amount of crystallization solution in a 1 L polypropylene container. 500 mL of the crystallization solution were prepared by admixing acetate buffer, 50% w/v PEG 4,000 solution and Milli Q water in the tube. In this example, the acetate buffer molarity was around 0.1 M, and the acetate buffer pH was around 5.2. PEG 4,000 was used at a concentration of 20% w/v. The container was stored at ambient temperature. Agitation was performed by rolling the container at around 60 rpm. Microscopy of a 1 µL aliquot of the solution was performed multiple times during the following weeks. Furthermore, the crystal yield was determined by OD280. An aliquot of the suspension was centrifuged at 14,000 rpm, and the protein concentration in the supernatant was assessed.
Results:
Needle-like crystals appeared after two days. No precipitated species were observed during the following month of storage. The crystal yield, as determined by OD280 from residual protein concentration in the supernatant, was between 60 and 70% after seven days.

Example 40

PEG 4,000/Sodium Acetate Crystallization Condition at 400 mL Batch Volume without Agitation MAK195F was exchanged into a buffer containing around 0.1 M sodium acetate at a pH of around 5.2. The protein concentration was adjusted to 10 mg/mL. Batch crystallization was performed by admixing around 200 mL of protein solution with an equal amount of crystallization solution in a 1 L polypropylene container. 200 mL of the crystallization solution were prepared by admixing acetate buffer, 50% w/v PEG 4,000 solution and Milli Q water in the tube. In this example, the acetate buffer molarity was around 0.1 M, and the acetate buffer pH was around 5.2. PEG 4,000 was used at a concentration of 20% w/v. The container was stored at ambient temperature. Microscopy of a 1 µL aliquot of the solution was performed multiple times during the following weeks. Furthermore, the crystal yield was determined by OD280. An aliquot of the suspension was centrifuged at 14,000 rpm, and the protein concentration in the supernatant was assessed.
Results:
Needle-like crystals were observed after 14 days. The crystals had a length of around 100-300 µm. The crystal yield, as determined by OD280 from residual protein concentration in the supernatant, was between 40 and 50% after 31 days.

E. Methods for Crystal Processing and Analysis

Example 41

Washing of Crystals

After formation of crystals, a washing step without redissolving the crystals is favorable. Therefore, after a crystallization process as described in Example 36 was finished, the crystal slurry was transferred into centrifugation tubes and centrifuged at 500 to 1000×g for twenty minutes. The centrifugation was performed at 4° C. or at ambient temperature. After centrifugation, the supernatants were discarded, and the crystal pellets were easily resuspended in a buffer containing around 20% w/v PEG 4,000 in around 0.1 M sodium acetate at a pH around 5.2. No measurable solubility of MAK195F crystals in the washing buffer occurred, as analyzed by OD280. The centrifugation/resuspension steps were subsequently repeated for one to three times, and after this washing procedure, the pellets were resuspended and stored.

Example 42

Yield Extension of the Crystallization Process

The endpoint of a crystallization process can be defined as the time point when OD280 measurements of aliquots of the supernatant of the crystallization slurry are constant, e.g., for three subsequent days. A yield extension was found to be possible by adding a certain amount of additional PEG 4,000 (50% w/v solution in around 0.1 M sodium acetate buffer at a pH of around 5.2) to the supernatant of the crystallization slurry. Crystals of the same shape as the first crop formed during the following days. Applying this procedure, the overall yield was easily driven beyond 90%, without introduction of precipitation.

For example, the PEG 4,000 concentration was raised from around 10% w/v to around 20% w/v, 18% w/v, 16% w/v, 14% w/v and 12% w/v, in aliquots of the supernatant of Example 39. After storage overnight at ambient temperature, precipitated species were observed at around 20% w/v, 18% w/v and 16% w/v PEG 4,000. Crystals without concomitant precipitation were found at around 14% w/v and 12% w/v PEG 4,000. By adding PEG 4,000 to an overall concentration of around 14% w/v to the residual supernatant of the crystallization slurry, the overall crystal yield was driven from around 60 to 70% to over 90% in two days.

Example 43

Analysis of Crystals by SDS PAGE

To confirm the protein character of the crystals, crystals from Example 36 were washed following the protocol of Example 41. After several washing steps, it was determined by OD280 that no measurable amounts of dissolved protein were present in the washing buffer supernatant. The supernatant was discarded, and the crystals were subsequently dissolved in distilled water. OD280 measurement of this solution revealed that dissolved protein was now present, as UV absorbance was significant. SDS-PAGE analysis of this solution, when compared to a MAK195F standard, showed the same pattern.

Example 44

Analysis of Crystals by SE-HPLC

To assess the content of aggregated species of MAK195F crystals, an aliquot of washed crystals from Example 36 was centrifuged and redissolved in the SE-HPLC running buffer according to standard methods. Upon completion of the crystallization process, in this example seven days at ambient temperature, the aggregate content increased slightly from about 0.9% to about 1.3-1.4%. It is not yet clear whether such aggregates are an intrinsic feature of MAK195F crystals, or if, for example, non crystallized soluble MAK195F monomers aggregate on the crystal surface.

The experimental conditions of the above batch experiments which rendered MAK195F crystals are summarized in Table 2.

TABLE 2

Selected Batch Experiments rendering crystals of MAK195F

| Ex. | Batch Volume ml | Crystallization solution | Agit. | Protein buffer No: | Yield Crystal % | pH Buffer | Protein Conc. Final mg/ml | Temp. | Day of visual control |
|---|---|---|---|---|---|---|---|---|---|
| 20 | 0.05 | 4-12% PEG 4000, 0.05M NaAc | – | 1 | not determined (n.d.) | 5.7 | 5 | amb | 3 d |
| 21 | 0.05 | 16-22% PEG 4000, 0.1M NaAc | – | 1 | n.d. | 5.7 | 5 | amb | 7 d |
| 22 | 0.3 | 18-24% PEG 4000, 0.1M NaAc | – | 1 | n.d. | 5.7 | 5 | amb | 14 d |
| 23 | 0.3 | 18-24% PEG 4000, 0.1M NaAc | – | 2 | n.d. | 5.7 | 6.2 | amb | 14 d |
| 24 | 0.15 | 16-28% PEG 4000, 0.1M NaAc | – | 1 | various | 4.2, 4.7, 5.2, 5.7 | 5 | amb | 7 d |
|  |  | 14-28% PEG 4000, 0.1M Citrate | – | 1 | various | 4.7, 5.2, 5.7 | 5 |  |  |
| 25 | 1 | 16%, 18% PEG 4000, 0.1M NaAc | – | 1 | n.d. | 4.7, 5.2 | 5 | amb | 1 month |
| 26 | 0.15 | 18%, 20% PEG 4000, 0.1M NaAc | – | 3 | n.d. | 5.5 | 5 | amb | 12 d |
| 27 | 1 | 16-24% PEG 4000, 0.1M NaAc | – | 3, 4 |  | 5.0, 5.5 | 5 | amb | 1 month |
| 28 | 1 | 22% PEG 4000, no buffer | – | 3, 4 | n.d. | 5.0, 5.5 | 5 | amb | 1 month |
| 29 | 1 | 20% PEG 4000, 0.1M NaAc | – | 5, various amounts of polysorbate 80 | n.d. | 5.5 | 5 | amb | 1 month |
| 30 | 0.1 | 16% PEG 4000, 0.1M NaAc | – | 6 | n.d. | 5.2 | 5 | amb | 14 d |
| 31 | 10 | 18% PEG 4000, 0.1M NaAc | – | 1 | 60-80 after 10 days | 5.2 | 5 | amb | months |
| 32 | 10 | 18% PEG 4000, 0.1M NaAc | + | 1 | 60-80 after 10 days | 5.2 | 5 | amb | months |
| 33 | 10 | 20-22% PEG 4000, 0.1 M NaAc | – | 3 | 60-80 after 10 days | 5.5 | 5 | amb | 1 month |

TABLE 2-continued

Selected Batch Experiments rendering crystals of MAK195F

| Ex. | Batch Volume ml | Crystallization solution | Agit. | Protein buffer No: | Yield Crystal % | pH Buffer | Protein Conc. Final mg/ml | Temp. | Day of visual control |
|---|---|---|---|---|---|---|---|---|---|
| 34 | 10 | 20% PEG 4000, 0.1 M NaAc | + or − | 6 | 50-80 after 10 days | 5.2 | 5 | amb | 21 d |
| 35 | 10 | 20% PEG 4000, 0.1 M NaAc | + or − | 3 | 50-80 after 10 days | 5.5 | 5 | amb | 21 d |
| 36 | 250 | 20% PEG 4000, 0.1 M NaAc | + | 6 | 60-70 after 7 days | 5.2 | 5 | amb | months |
| 37 | 10 | 20% PEG 4000, 0.1 M NaAc | + | 6 | n.d. | 5.2 | 5 | amb | 3 d |
| 38 | 10 | 20% PEG 4000, 0.1M NaAc | + | 6 | NO CRYSTALS n.d. | 5.2 | 5 | 4° C. amb | 10 d 1 d |
| 39 | 1000 | 20% PEG 4000, 0.1M NaAc | + | 6 | 60-70 after 7 days | 5.2 | 5 | amb | weeks |
| 41 | | supernatant of #39 and added PEG 4000, overall PEG concentration 12% overall, PEG concentration 14% | | | >90% (overall, 14% PEG) | 5.2 | 5 | amb | 2 d |

Crystallization solution:
1:1 diluted with protein sample
Protein buffer
1: 20 mM HEPES/150 NaCl/pH 7.4
2: 10 mM NaPhos, 150 mM NaCl, 0.01% Pluronic F68, pH 7.2
3: 0.1M NaAc, pH 5.5
4: 0.1M NaAc, pH 5.0
5: 0.1M NaAc, pH 5.5, 0, 0.001, 0.01, 0.1, 1% Polysorbate 80
6: 0.1M NaAc, pH 5.2

F. Experiments Investigating Influence of Agitation of Crystallization Results The purpose of these experiments was to investigate the influence of agitation speed on a readily implemented batch crystallization method for an antibody, for example, MAK195F. By keeping all other crystallization parameters constant, the degree of agitation was varied in five successive batches (10, 20 40, 60 and 80 rpm). The influence on crystallization kinetics, total yield and particle shape and size distribution was explored.

Example 45

Crystallization of MAK195F Under Controlled Conditions

Materials
MAK195F, lot G008.01E/PZ0105P025 (Abbott Laboratories)
Sodium acetate anhydrous (Gruessing)
Acetic acid glacial (Merck)
Polyethylene glycol 4,000 (Clariant)
Polypropylene bottles, diameter 8 cm, height 10 cm
Methods
Frozen MAK195F (stored at −80° C. in 500 mL polypropylene bottles) was thawed at ambient temperature within 2 hours. Upon thaw, the drug substance solution was clear, and no contaminant particles were observed by eye. Protein buffer was prepared as follows: 500 mL acetate buffer was prepared by dissolving 41.02 g sodium acetate in purified water. The volume was adjusted to 500.0 mL and the pH was adjusted to 5.2 with glacial acetic acid. 400 mL of this buffer were diluted to an overall volume of 4.0 L with purified water. This buffer was freshly prepared prior to each of the five batch crystallizations.

For each batch crystallization, 25 mL MAK195F were exchanged into the protein buffer by using Slide-A-Lyzer dialysis cassettes (12-30 mL filling volume, 10 kDa MWCO). The protein concentration was then adjusted to 10 mg/mL with protein buffer, and the solution was sterile filtered using a 0.22 µm filter disc (PVDF).

The crystallization solution was prepared as follows: 500 mL acetate buffer were pre-pared by dissolving 41.02 g sodium acetate in purified water. The volume was adjusted to 500.0 mL, and the pH was adjusted to 5.2 with glacial acetic acid. 200 g PEG 4,000 were dissolved in 100 mL of the acetate buffer and purified water, and subsequently was volume was adjusted to 1,000 mL. This crystallization solution was used for all batch crystallizations and stored at 2-8° C.

Crystallization was initialized by admixing 25 mL protein solution with 25 mL crystallization solution in a polypropylene bottle. The bottle was subsequently agitated by rolling at 20° C. for 9 days. 5 crystallization batches were set up and agitated at 10 rpm, 20 rpm, 40 rpm, 60 rpm and 80 rpm (rounds per minute), respectively. Each day, an aliquot of 200 µL was withdrawn from any sample, and crystal yields were determined by OD280 protein concentration determination of the supernatants after centrifugation of the crystals:

Crystal yield [%]=$C_{protein, total}-C_{protein, supernatant}/C_{protein, total}\times 100\%$ Light microscopy pictures of the crystals were taken as follows: After 8 days of agitation, a 10 µL aliquot was pipetted onto an object holder and was subsequently covered with a glass cover slide. The preparation was assessed using a Zeiss Axiovert 25 inverted light microscope equipped with E-PI 10× oculars and a 40× objective. Pictures were taken using a digital camera (Sony Cybershot DSC S75).

Particle Size Measurements of the Crystals were Performed as Follows:

I) Manual Assessment

After 8 days of agitation, a 10 µL aliquot was pipetted onto an object holder and was subsequently covered with a glass cover slide. A Nikon Labophot microscope, equipped with CFW 10× oculars and a 20× objective was used. Crystal sizes (maximum length) were assessed by transferring the microphotograph onto a computer screen via a JVC TK C1380 color video camera, and by measuring the length of 100 crystals via the JVC Digital Screen Measurement Comet software version 3.52a. From these 100 measurements, particle size distributions and the mean value of maximum length were specified.

II) Automated Assessment

To get an insight into particle size distributions of the samples on a more statistically significant base, the suspensions were also analyzed with a PS Prozesstechnik XPT-C Optical Particle Analysis System (PS Prozesstechnik GmbH, Basel, Switzerland). Feret$_{max}$ (maximum distance over all particle directions) values were recorded. Particle numbers per sample were above 5,000, respectively.

SE-HPLC data was assessed as follows: Two 300 µL aliquots of any crystallization batch were withdrawn after 12 days. The aliquots were centrifuged, and subsequently the supernatant was discarded. The crystal pellet was redissolved with MAK195F drug sub-stance buffer so that protein concentration was 1 mg/mL. The aliquots were stored at −80° C. until SE-HPLC analysis. SE-HPLC analysis was performed according to standard methods.

The effect of agitation speed (Polypropylene bottles, diameter 8 cm, height 10 cm, rounds per minute=rpm) on crystallization kinetics and total yield is depicted in FIG. 1.

The results indicated that by applying different rotation speeds, neither crystallization kinetics (shape of the curve) nor total yield ($y_{max}$) are influenced. While total yield was always around 55% after 8 days of crystallization, the shapes of the crystallization curves show that all experiments can be divided into three analogous parts:

lag phase (days 1 and 2), no yield;
main crystallization phase (days 3-5), crystallization rates>10% (compared to yield is reached.
minor crystallization phase and plateau (days 6-8), crystallization rates<10%, maximum MAK195F purity by SE-HPLC analysis SE-HPLC analysis was performed for each crystallization batch to check whether the rotation speed influences formation of degradation products and/or aggregates. The results depicted in Table 3 demonstrate that MAK195F purity is not affected.

TABLE 3

Influence of agitation speed on MAK195F purity

| Sample | Aggregates (%) | Monomer (%) | Fragments (%) |
|---|---|---|---|
| Bulk material before crystallization | 0.8 | 98.4 | 0.8 |
| 10 rpm | 2.2 | 97.6 | 0.2 |
| 20 rpm | 2.1 | 97.7 | 0.2 |
| 40 rpm | 1.9 | 97.9 | 0.2 |
| 60 rpm | 2.4 | 97.3 | 0.3 |
| 80 rpm | 2.1 | 97.7 | 0.2 |

Particle Shape and Size Distribution

Figure 2:
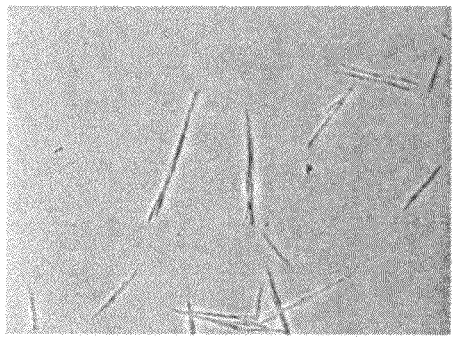
FIG. 2 shows microscopic images of MAK195F crystals obtained at different roller speeds.
Figure 2:
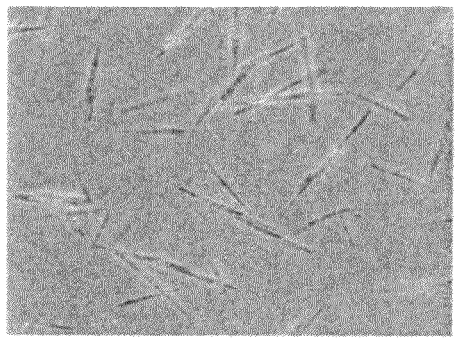
Figure 2:
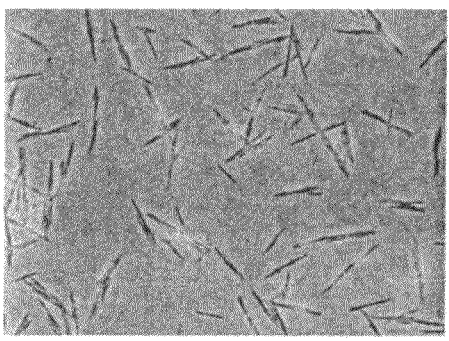
Figure 2:
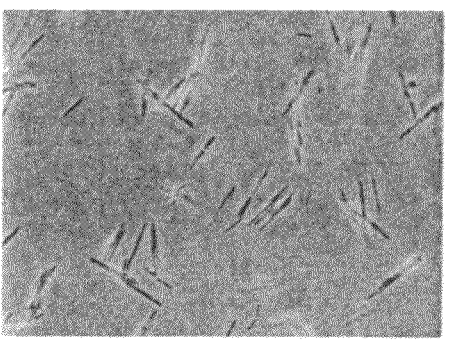
Figure 2:
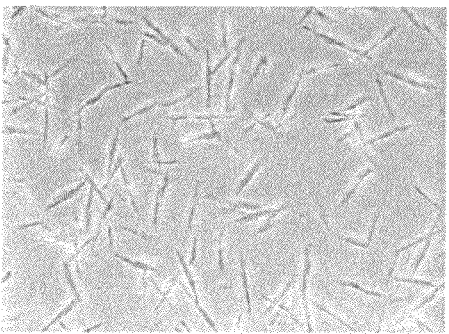

The effect of the agitation speed on particle shape is shown in FIG. 2. All batch crystallizations rendered crystalline matter in the shape of needles.

Figure 3:
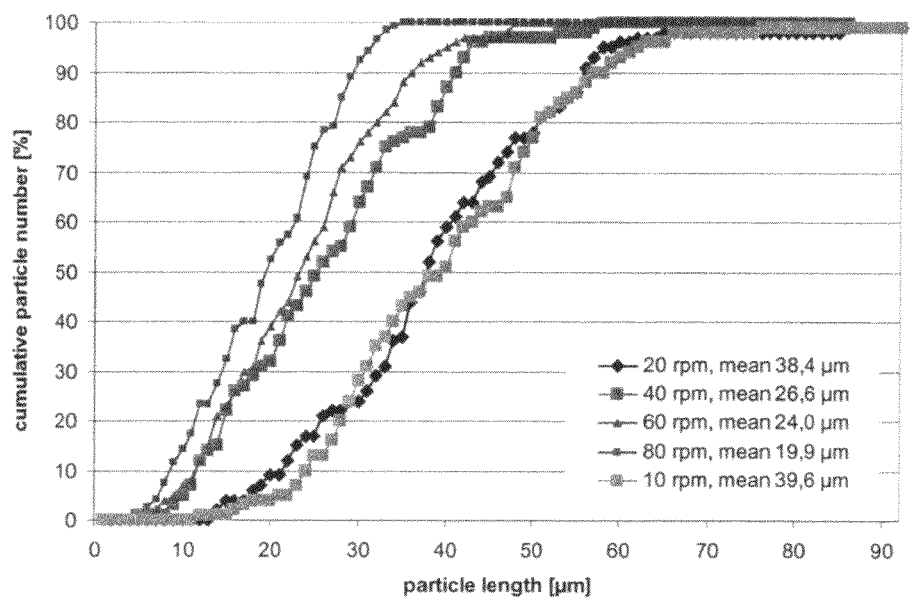
FIG. 3 shows the influence of roller speed on the crystal length of MAK195F crystals. The mean particle lengths for different roller speeds are stated for each of the five different speeds.

Picture A: MAK195F crystals, 10 rpm
Picture B: MAK195F crystals, 20 rpm
Picture C: MAK195F crystals, 40 rpm
Picture D: MAK195F crystals, 60 rpm
Picture F: MAK195F crystals, 80 rpm The effect of the agitation speed on particle size distribution is depicted in FIG. 3 (manual assessment). Mean particle sizes differed from 39.6 µm for the 10 rpm batch and 19.9 µm for the 80 rpm batch.

By the automated method applying the XPT-C Optical Particle Analysis System, following values were obtained: 10 rpm, x(1,2) 26.4 µm; 20 rpm, x(1,2) 25.9 µm; 40 rpm, x(1,2) 20.4 µm; 60 rpm, x(1,2) 23.6 µm; 80 rpm, x(1,2) 18.7 µm.

This data demonstrated on a statistically significant base that higher agitation levels result in smaller needle lengths. Deviations between absolute values obtained from automated and manual measurements may be explained by the fact that the particles might not always be perfectly aligned (i.e., full Feret$_{max}$ visible) in the measurement cell equipped with a CCD camera.

This study was initiated to study whether a relationship exists between batch rotation speed and several batch parameters. While factors like mAb purity, crystallization kinetics, yield and basic crystal morphology are not affected, the data presented demonstrate that crystal size is decreased by an increase in the degree of agitation.

G. Miscellaneous Examples

Example 46

Solid Crystallization Agent

MAK195F is exchanged into a buffer containing about 0.1 M sodium acetate at a pH of about 5.2. The protein concentration was adjusted to 10 mg/mL.

Batch crystallization is performed by admixing about 500 µL of the protein solution with about 400 µL acetate buffer (0.1 M, pH 5.2) in a 2 mL Eppendorf reaction tube. Subsequently, solid polyethylene glycol is added to a final concentration of 10% m/v (100 mg/mL). The tube is subsequently closed and agitated until complete dissolution of the crystallization agent is obtained. The tube is stored at ambient temperature without agitation. Microscopy of aliquots of the crystallization mixture is performed multiple times during the following weeks as crystallization progresses.

Example 47

Different Buffer Preparation Protocol and Preparation of Crystals

In this example, the acetate buffers are prepared as described as follows: 60 g of glacial acetic acid is diluted with about 840 mL of purified water. The pH is adjusted with sodium hydroxide solution and the volume is adjusted to 1,000 mL. In this case, total acetate is fixed at 1 M (100 mM in the protein solution, the crystallization solution and the crystallization mixture).

Crystallization is performed according to Example 36.

Example 48

Preparation of Encapsulated Crystals

Crystals as obtained in Example 36 are positively charged as determined via zeta potential measurement using a Malvern Instruments Zetasizer nano.

The crystals are washed and suspended in a buffer containing excipients that conserve crystallinity, and which has a pH that keeps the crystals charged. Subsequently, an appropriate encapsulating agent is added to the crystal suspension. In this context, an appropriate encapsulating agent is a (polymeric) substance with low toxicity, biodegradability and counter ionic character. Due to this counter ionic character, the substance is attracted to the crystals and allows coating. By this technique, the dissolution of crystals in media, which do not contain any other excipient maintaining crystallinity is preferably sustained.

Example 49

Preparation of Encapsulated/Embedded Crystals

Crystals are obtained as described in Example 36.
The crystals are washed and suspended in a buffer containing excipients that conserve crystallinity.
Using art known methods the crystals can then be
embedded by drying the crystals and combining these dried crystals with a carrier, e.g., by compression, melt dispersion, etc.
encapsulated/embedded by combining a crystal suspension with a carrier solution which is not miscible with water. The carrier precipitates after removal of the solvent of the carrier. Subsequently, the material is dried.
encapsulated/embedded by combining a crystal suspension with a water miscible carrier solution. The carrier precipitates as its solubility limit is exceeded in the mixture.
embedded by combining dried crystals or a crystal suspension with a water miscible carrier solution.
embedded by combining dried crystals with a carrier solution which is not water miscible.

H. Crystal Characterization

H1. Bioactivity Test

Example 50

Retention of Bioactivity of Crystalline MAK195F a) General Method

The neutralizing effect of Afelimomab™ solution against the cytotoxic effect of rHuTNF is determined by incubating mouse L-929 cells as indicators in a 96-well microtiter plate in the presence of various Afelimomab™ concentrations for 48 hours with a defined amount of rHuTNF at 37° C. The surviving cells are stained with crystal violet. The intensity of color is measured by spectrophotometry in the individual wells of the microtiter plate and evaluated. The $IC_{50}$ is measured, i.e., the concentration of Afelimomab™ that reduces the cytotoxic effect of rHuTNF on L-929-cells such that 50% of the cells survive.

In a separate dilution box, starting from the 1 µg protein/mL dilutions, the 9 titer curve measuring points (curve dilutions) were prepared individually in the dilution tubes for sample and reference standard.

The L-929 cell suspension was diluted with medium to provide a concentration of 60,000 cells/mL. Subsequently, 100 µL per well of the respective cell concentration were pipetted into columns 1-11 of the test plate. The wells in columned 12 contain only 100 µL of medium each. Incubation was applied at 37° C. and 5% (v/v) $CO_2$ for 24 hours in the test plate.

After a 24 hour incubation, 50 µL of each of the 9 titer curve dilutions was transferred from the dilution box to the test plate for the reference standard or sample, i.e., for the reference standard to wells in rows A-D in columns 1-9 and for the sample to the wells in rows E-H in columns 1 to 9.

50 µL of medium were pipetted into column 10; and 100 µL each were pipetted into columns 11 and 12. 50 µL of TNF reference standard (12.5 ng protein/mL medium) was pipetted into the wells in column 1 to 10, row A to H, whereby column 10 corresponded to the 100% lysis value (TNF control). Column 11 was a 100% growth control, and column 12 contained no cell material and thus acted as a blank. The final volume per well was 200 µL. Incubation of the test plates was performed for 48 hours at 37° C. and with 5% $CO_2$.

Following incubation for 2 days, the liquids from the test plate wells were discarded by turning quickly and giving a single, vigorous downward shake. Then 50 µL of crystal violet solution were pipetted into each well. The solution was left in the wells for 15 minutes and then discarded as described above. The plates were washed and dried at room temperature for about 30 minutes. Subsequently, 100 µL of reagent solution were pipetted into each well. Agitation of the plates (at about 300 rpm for 15 min) produced an evenly colored solution in each of the wells. The absorbance of the dye in the test plate wells was measured in a plate photometer at 620 nm. Individual values were plotted on a graph, with the absorbance (y axis) being plotted against the respective dilution or concentration ng/mL (x axis) of antibody.

Four parameters were used for bioactivity determination: 1) minimum plateau of the curve describing dose vs. inhibitory effect; 2) maximum plateau of the curve describing dose vs. inhibitory effect; 3) $IC_{50}$ value; and 4) the slope of the curve inflection point. From the 4-parameter plot, the concentration was read off at which half the cells survive and half die ($IC_{50}$ value). This concentration was calculated by parameter 3 of the 4-parameter function of the curve data. The mean values of the reference standard concentrations were calculated. The relative biological activity of the sample was calculated by dividing the mean $IC_{50}$ value of the reference standard by the individual $IC_{50}$ values of the sample and multiplication by 100%. The relative activities were then averaged.

b) Results

The test was performed as a comparison of the biological activity of the sample (washed crystals; washing protocol as described in Example 41, crystals derived from the batch as described in Example 39) to that of a reference standard. The absorption values, plotted versus the concentration of Afelimomab™ and assessed by a 4-parameter nonlinear regression, revealed the $IC_{50}$ values for the inhibition of the TNF effect by the antibody. Since both samples were run in four repeats on one microplate this results in four $IC_{50}$ values for Afelimomab™ reference standard and sample respectively. Subsequently, the mean of the $IC_{50}$ values of the reference standard was calculated and the relative activity of each repeat of the sample was assessed by dividing the mean $IC_{50}$ value of the reference standard by the relevant $IC_{50}$ value of the sample and multiplication by 100%.

The test of the sample (crystal suspension 1.87 mg/mL) revealed a relative biological activity of 102%, and therefore fully biologically active.

H2. Microscopic Characterization

Example 51

Microscopic Characterization of Crystals of MAK195F a) Optical Analysis of mAb Crystal Batch Samples After homogenization, aliquots of 1 to 10 μL sample volume were pipetted onto an object holder plate and were covered with a glass cover slide. The crystal preparations were assessed using a Zeiss Axiovert 25 inverted light microscope equipped with E-PI 10× oculars and 10×, 20× and 40× objectives, respectively. Pictures were taken using a digital camera (Sony Cybershot DSC S75).

H3. Birefringence

For the detection of birefringent behavior, a Nikon Labophot microscope, equipped with CFW 10× oculars and 4×, 10×, 20× and 40× objectives was used. Furthermore, the microscope was equipped with a filter set (analyzation and polarization unit).

Crystals as generated from all batch experiments exhibited birefringence.

H4. Syringeability

A MAK195F crystal suspension of 150 mg/mL protein incorporated in crystals and formulated in a washing buffer from Example 41 was syringeable through a 27G needle.

Figure 8:
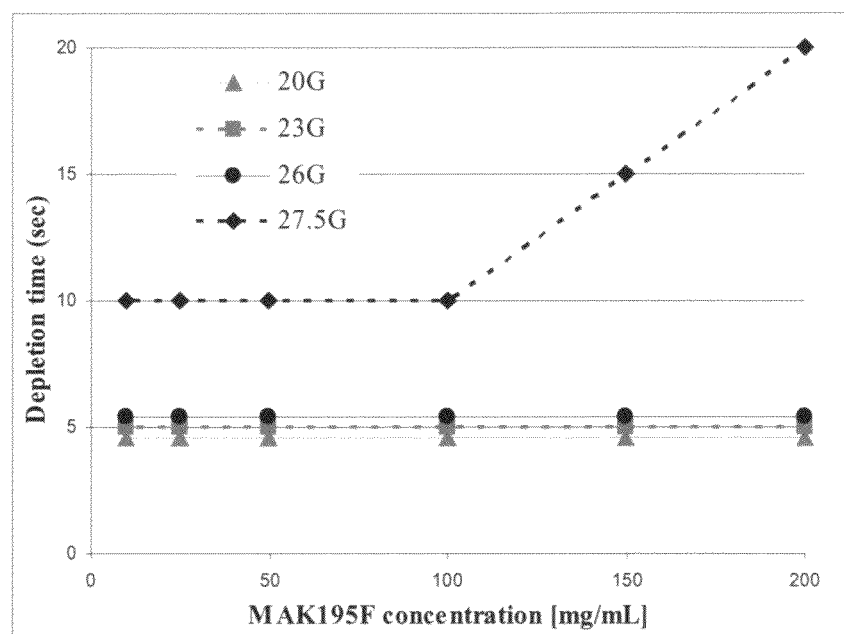
FIG. 8 shows syringeability of MAK195F crystal suspensions in dependency of crystal concentration and needle diameter.

In the following section, experiments are listed that were performed to determine the syringeability of crystalline suspensions (in PEG) of monoclonal antibody fragment MAK195F (10-200 mg/ml) using different gauge needles.
PEG Buffer:
18% PEG 4,000 m/v
0.01% Poloxamer 188
10 mM sodium phosphate buffer
pH was adjusted to 7.2 with sodium hydroxide solution Syringe depletion (1 mL filling volume) was performed as it would be manually by a patient in the course of administration. 20-27.5 G needle sizes were evaluated.
Syringes:
20/23/26 G:
Henke Sass Wolf GmbH 1 mL Norm-Ject syringes, equipped with
  Henke Sass Wolf GmbH Fine-Ject® 20 G needles
  Terumo® 23 G needles
  Neopoint® 26 G needles
27.5 G:
BD HyPak SCF™ 1 mL long syringes, equipped with 27.5 G RNS needles 38800 Le Pont du Claix The results (FIG. 8) suggest that 27.5 G needles provide a slower delivery of the crystals at high concentrations.

I. Secondary Structure

Example 52

Retention Of Native Secondary Structure Upon Crystallization/Re-dissolution of Crystals IR spectra were recorded using a Confocheck system on a Bruker Optics Tensor 27. Liquid samples were analyzed using a MicroBiolytics AquaSpec cell. Measurements of protein suspensions were performed with a Harrick BioATRII Cell™. Each sample was assessed performing at least two measurements of 120 to 500 scans at 25° C. Blank buffer spectra were subtracted from the protein spectra, respectively. Protein second derivative spectra were generated by Fourier transformation and vector normalised from 1580-1720 cm−1 for relative comparison.

Figure 4:
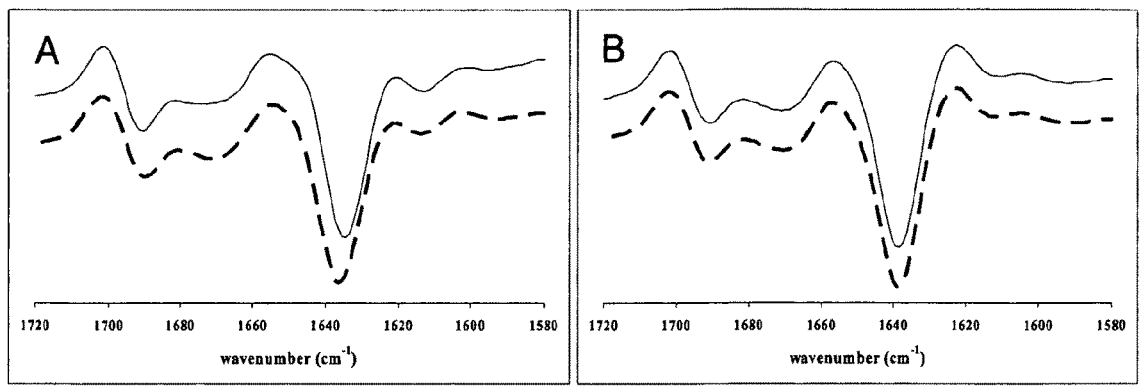
FIG. 4 shows second derivative IR spectra of MAK195F samples. A Crystal suspension; B Re-dissolved crystals. Solid lines represent samples from crystalline MAK195F, dashed lines liquid standards. A was recorded with the BioATR cell, and B with the AquaSpec cell, respectively. An offset between sample and standard was inserted for better illustration, respectively.

Re-dissolution of crystals was performed as follows: Crystal suspensions were centrifuged, the supernatant discarded, and the pellet was dissolved in 0.1 M sodium acetate buffer pH 5.2 to 10 mg/mL protein concentration. FIG. 4 depicts FT-IR second derivative spectra of crystalline MAK195F suspensions (crystallized following the process as described in Example 39 and washed following the procedure introduced in Example 41) and after re-dissolution of such pretreated crystals. The spectra demonstrate that no significant alterations of the secondary structure were observed, either in the crystalline solid state or after re-dissolution.

J. Stability Data

Example 53

12 Months Stability Data (Se Hplc, Ft-Ir, Morphology) in Peg/Phosphate Buffer

MAK195F was crystallized applying the crystallization procedure described in Example 39. The crystals were washed as described in Example 41, in this case with a buffer containing 18% (w/v) PEG 4,000, 0.01% Poloxamer 188 and 10 mM sodium phosphate pH 7.2. Subsequently, the crystals were concentrated to 5 mg/mL and 200 mg/mL protein content by centrifugation, respectively, and stored at 2-8° C. Stability data of 5/200 mg/mL crystalline MAK195F over 12 months storage at 2-8° C., clearly indicating retention of above 90% monomer.
Materials:
Dispersion Buffer:
18% PEG 4,000 m/v
0.01% Poloxamer 188
10 mM sodium phosphate buffer
pH was adjusted to 7.2 with sodium hydroxide solution
SE-HPLC

TABLE 4

5 mg/mL crystalline MAK195F after redissolution

| Time point | Aggregates (%) | Monomer (%) | Fragments (%) |
|---|---|---|---|
| T0 | 1.6 | 97.9 | 0.5 |
| 1 months | 1.8 | 97.8 | 0.4 |
| 3 months | 2.2 | 97.6 | 0.2 |
| 6 months | 2.6 | 97.0 | 0.4 |
| 9 months | 2.5 | 96.5 | 1.0 |
| 12 months | 2.6 | 96.7 | 0.7 |

TABLE 5

200 mg/mL crystalline MAK195F after redissolution

| Time point | Aggregates (%) | Monomer (%) | Fragments (%) |
|---|---|---|---|
| T0 | 1.8 | 97.7 | 0.5 |
| 1 months | 1.8 | 97.9 | 0.3 |

TABLE 5-continued 200 mg/mL crystalline MAK195F after redissolution

| Time point | Aggregates (%) | Monomer (%) | Fragments (%) |
|---|---|---|---|
| 3 months | 2.1 | 97.5 | 0.4 |
| 6 months | 2.1 | 97.3 | 0.6 |
| 9 months | 2.3 | 96.9 | 0.8 |
| 12 months | 2.2 | 97.1 | 0.7 |

A Dionex HPLC system (P680 pump, ASI 100 autosampler, UVD170U) was used. MAK195F samples were separated on two serially linked GE Superose® 12 columns, applying a flow rate of 0.5 mL/min. Detection was carried out at a wavelength of 280 nm. The running buffer consisted of 0.5 M sodium chloride in a 0.1 M potassium phosphate buffer pH 6.9.

FT-IR

IR spectra were recorded using a Confocheck system on a Bruker Optics Tensor 27. Liquid samples were analyzed using a MicroBiolytics AquaSpec cell. Measurements of protein suspensions were performed with a Harrick BioATRII Cell™. Each sample was assessed performing at least two measurements of 120 to 500 scans at 25° C. Blank buffer spectra were subtracted from the protein spectra, respectively. Protein second derivative spectra were generated by Fourier transformation and vector normalised from 1580-1720 $cm^{-1}$ for relative comparison.

Redissolution of crystals was performed as follows: Crystal suspensions were centrifuged, the supernatant discarded, and the pellet was dissolved in 0.1 M sodium acetate buffer pH 5.2 to 10 mg/mL protein concentration.

Figure 5:
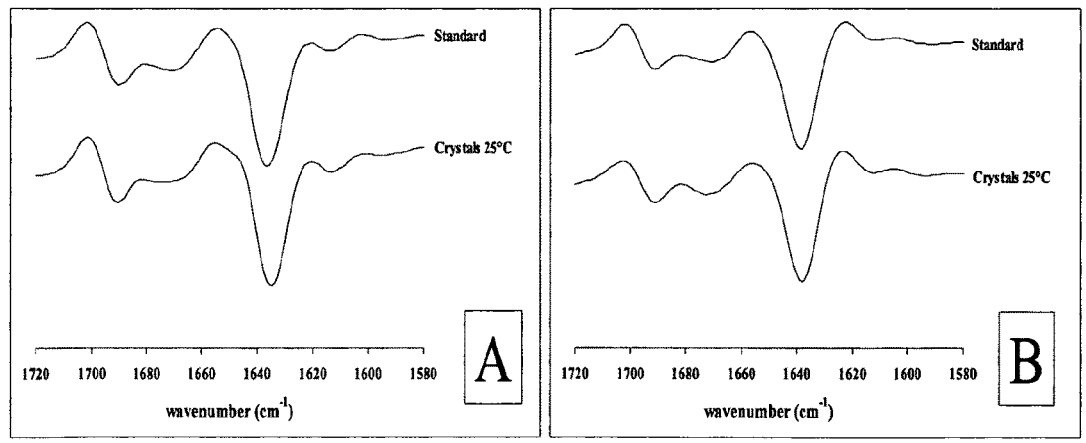
FIG. 5 shows second derivative IR spectra of MAK195F samples (200 mg/mL crystalline protein in 18% PEG 4,000 buffer) stored for 6 months at 25° C. A Crystal suspension; B Re-dissolved crystals. A was recorded with the BioATR cell, and B with the AquaSpec cell, respectively. An offset between sample and standard was inserted for better illustration, respectively.

FIG. 5 depicts FT-IR second derivative spectra of crystalline MAK195F suspensions (200 mg/mL shelf stability samples, prepared as described above and stored for 6 months at 25° C.) and after re-dissolution of such pre-treated crystals. The spectra demonstrate that no significant alterations of the secondary structure were observed upon storage at 25° C. for 6 months, neither in the crystalline solid state nor after re-dissolution.

Morphology

Aliquots of 1 to 10 μL sample volume were pipetted on an object holder plate, diluted with formulation buffer (20% PEG) and covered with a glass cover slide. The preparations were assessed using a Zeiss Axiovert 25 inverted light microscope equipped with E-PI 10× oculars and 10×, 20× and 40× objectives, respectively. After 12 months storage at 2-8° C. no significant morphological change was observed in light microscopy analysis of the crystals.

K. DSC Analytics

Example 54

DSC Analysis

Differential scanning calorimetry (DSC) was performed with unstressed samples at 200 mg/mL. Crystal suspensions as prepared in paragraph 3), liquid formulations (MAK195F in a buffer containing 0.01% Poloxamer 188, 150 mM sodium chloride and 10 mM sodium phosphate buffer, pH 7.2) and placebo 18% PEG 4,000 crystal suspension buffer were compared.

Figure 6:
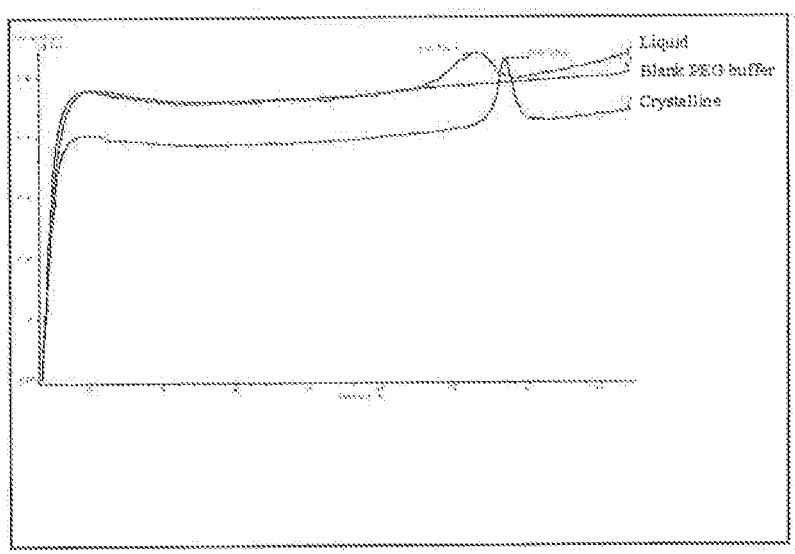
FIG. 6 shows DSC thermograms of MAK195F crystal suspension, liquid formulation (both 200 mg/mL) and a placebo suspension buffer containing PEG 4,000.

A Netzsch DSC 204 Cell equipped with a CC 200 L controller, a CC 200 supply system and a TASC 414/3A controller were used. 20 μL of the liquid samples or suspensions were transferred into Al-crucibles, and after sealing the crucibles sample analysis was performed by heating from 0-100° C. at a heating rate of 5 K/min. FIG. 6 depicts typical thermograms obtained for the samples.

The liquid solution exhibited a rather broad endotherm between 66 and 78° C. whereas, on the contrary, the crystalline suspension was characterized by a markedly sharper endothermic peak at around 77° C. No thermal events were connected to the heating of the placebo suspension buffer (FIG. 6).

The results suggest that MAK195F has higher conformational stability in the crystalline state due to the higher endothermic peak temperature in comparison to the liquid formulation and that MAK195F has a higher degree of purity and conformational homogeneity in the crystalline state than in solution due to the sharper endothermic peak (Elkordy, A. et al. (2002) Int. J. Pharmaceutics 247:79-90).

L. Scanning Electron Microscope (SEM) Characterization of MAK195F Crystals

Example 55

Scanning Electron Microscope (SEM) Characterization of MAK195F Crystals

Figure 7:
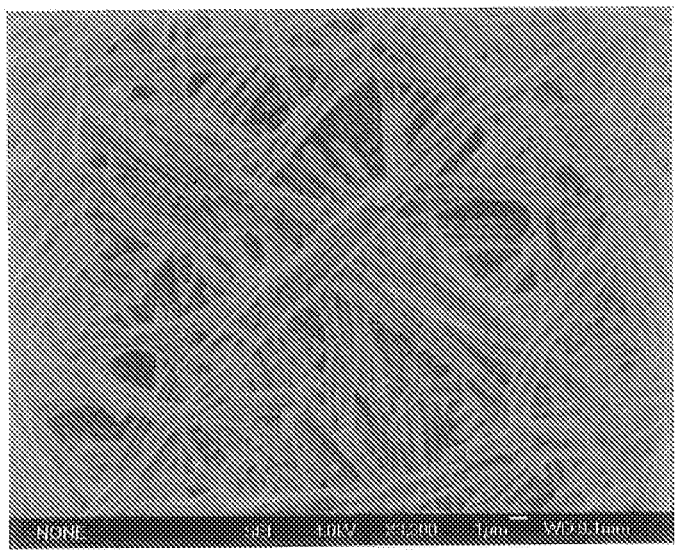
FIG. 7 shows representative picture of MAK195F crystals obtained by SEM.

An aliquot of an MAK195F crystal suspension prepared as described in Example 39 was centrifuged. After decanting the supernatant, the pellet was re-suspended in absolute ethanol. After several successive centrifugation/re-suspension in ethanol steps were performed, one drop of the suspension was transferred on an SEM sample holder and dried at room temperature. The sample was carbon sputtered and data were collected on a JEOL JSM 6500F scanning electron microscope equipped with an Oxford Instruments 7418 detector. FIG. 7 depicts a typical example of MAK195F crystals.

L. Yield Extension Applying a Continuous Process (Different Set-Up as in Existing Example 42)

Example 56

Yield Extension of the Crystallization Process, Different Set-Up Resulting in a Continuous Process The endpoint of a crystallization process can be defined as the time point when $OD_{280}$ measurements of aliquots of the supernatant of the crystallization slurry are constant, e.g., for three subsequent days. A yield extension is possible by adding a certain amount of additional PEG 4,000 (50% w/v solution in around 0.1 M sodium acetate buffer at a pH of around 5.2) to the supernatant of the crystallization slurry. Crystals of the same habit as the first crop form during the following days. Applying this procedure, the overall yield is driven beyond 90%, without introduction of precipitation.

In this example, additional precipitant and/or protein is "titrated" to a crystallization batch (optionally containing a certain amount of crystallization agent as basic level) at a pre-defined rate. Continuous crystallization over time is thereby induced, finally resulting in over 90% crystal yield.

M. Seeding of Crystallization Batches

Example 57

Seeding of MAK195F Crystallization Batches

A MAK195F crystallization batch is prepared as described in Example 39. After mixing the protein solution with the crystallization buffer, the mixture is seeded, e.g., by homogeneous seeding with pre-existent MAK195F crystals. For example, an aliquot of a crystal suspension prepared as described in Example 39, exhibiting around 60 to 70% crystal yield, might be added in, e.g., a 1/20 ratio (v/v) to the crystallization batch (in this example, 50 mL is added to 1,000 mL). Applying this strategy, total crystal yields and process durations are further optimized towards higher yields in shorter process times.

P. PK/TOX Studies

Example 58

Preparation of Samples for Pk/Tox Studies in Rats (See Below)

4 different formulations were prepared:
MAK195F liquid formulation, 50 mg/mL
MAK195F crystal suspension, 50 mg/mL, process with agitation (yielding smaller needles)
MAK195F crystal suspension, 200 mg/mL, process with agitation
MAK195F crystal suspension, 200 mg/mL, process without agitation (yielding larger needles)

a) MAK195F Liquid Formulation
Thawing of MAK195F Solution
20 mL solution of MAK195F (LOT G008.01E/PZ0105P025, c=12.4 mg/mL) was thawed in an agitated water bath at 25° C. within 2 hours.
Preparation of the 50 mg/mL Batch
20 mL MAK195F solution were concentrated to 5 mL by using a readily prepared Vivaspin 20 tube (30 kDa PES MWCO) and centrifuged at 5,000×g and 4° C. until the volume was reduced to 5 mL. The solution was sterile filtrated.
Determination of Concentration (OD280)
The concentration of the resulting MAK195F solution was determined by OD280, measuring 10 μL of protein solution diluted with 1990 mL distilled water against distilled water.
A=0.353/0.359/0.354, c=51.9 mg/mL
The solution was filled into sterile 2 mL Eppendorf reaction tubes.

| Composition | |
|---|---|
| MAK195F | 51.9 mg/mL |
| Pluronic F 68 | 0.1 mg/mL |
| sodium dihydrogen phosphate dihydrate | 1.56 mg/mL |
| sodium chloride | 8.77 mg/mL |
| sodium hydroxide | pH adjustment 7.2 | b) MAK195F crystal suspensions
1. Batch Crystallization:
Thawing of MAK195F Solution
400 mL solution of MAK195F (LOT G008.01E/PZ0105P025, c=12.4 mg/mL) was thawed in an agitated water bath at 25° C. within 2 hours. The solution was transferred into a 1000 mL beaker.
Preparation of the Buffer Exchange Device
A Vivaflow 50 (30000 MWCO, PES) cartridge was rinsed with 500 mL of distilled water until 400 mL of the water had entered the filtrate vessel.
Preparation of the Buffers
Buffer A (1 M Sodium Acetate Buffer pH 5.2)
41.02 g sodium acetate was dissolved in about 450 mL distilled water in a 500 mL graduated flask. A volume of 500 mL was adjusted by adding additional distilled water. The pH of the buffer was adjusted to 5.2 by adding concentrated acetic acid.
Buffer B (0.1M Sodium Acetate pH 5.2)
250 mL of buffer A were diluted with distilled water to an overall volume of 2500 mL in a 5000 mL beaker.
Buffer C (20% PEG 4000 in 0.1M Sodium Acetate pH 5.2)
150 mL of buffer A and 300 g PEG 4000 were transferred into a 1500 mL graduated flask and filled up with distilled water to an overall volume of 1500 mL. The buffer was then brought under a laminar air flow bench and sterile filtrated (2 pore size 0.22 μm filter disks).
Buffer Exchange of MAK195F
400 mL MAK195F solution were concentrated to 50 mL by using a readily prepared Vivaflow 50 cartridge. This concentrated solution (c=approx. 100 mg/mL) was diluted with 450 mL of buffer B in a 1000 mL beaker. Using the readily prepared Vivaflow 50 cartridge, the volume was brought back to 50 mL. This procedure was repeated once. In a last step 50 mL were diluted with 450 mL of buffer B, but the volume was not reduced, so that protein concentration should be around 10 mg/mL. The total dilution of the original MAK195F buffer is 1 to 1000.
Determination of the mAb Concentration and Adjustment to 10 mg/mL (OD280)
The concentration of the resulting MAK195F solution in buffer B was determined by OD280, measuring 40 μL of protein solution diluted with 1960 μL distilled water against distilled water.
A=0.258 c=9.4 mg/mL
Batch Preparation
470 mL of mAb solution were brought under a laminar air flow bench and were sterile filtrated (two pore size 0.22 μm filter disks). 260 mL of the solution were transferred into a 1000 mL graduated cylinder and admixed with 260 mL of buffer C. The mixture was transferred in to a 1000 mL polypropylene container bottle. The bottle was sealed with parafilm and stored at 20° C. The bottle was agitated at around 60 rpm. ("process with agitation"). 210 mL of the solution were transferred into a 1000 mL graduated cylinder and admixed with 210 mL of buffer C. The mixture was transferred in to a 1000 mL polypropylene container bottle. The bottle was sealed with parafilm and stored at 20° C. The bottle was not agitated ("process without agitation").
2. Preparation of the "Process with Agitation" Samples, 16 Days after Batch Crystallization Start:
Formulation Buffer Preparation
First, 50 mL of a 0.5 M phosphate stock solution were prepared. 3.9 g sodium dihydrogen phosphate dihydrate were dissolved in around 40 mL purified water, and the pH was brought to 7.2 with sodium hydroxide. The volume was adjusted to 50 mL. 360 g PEG 4,000, 40 mL of the stock solution and 0.2 g Pluronic F 68 were dissolved to 2000 mL with purified water.
Determination of Crystal Yield
The concentration of the resulting MAK195F crystallization batch was determined by OD280. 150 μL aliquots were centrifuged at 14,000 rpm for 20 minutes. 100 μL of the supernatant were diluted with 1900 μL distilled water and measured against distilled water.

| | | |
|---|---|---|
| Supernatant I: | A = 0.158 | |
| Supernatant II: | A = 0.154 | c = 2.3 mg/mL crystal yield 54% |

Concentration and Buffer Exchange/Filling

All centrifugation steps were performed at speeds of between 500 to 2,000 rpm in that way that pellets formed which were easily resuspendable, and no residual solid was found in the supernatant. The crystal slurry was aliquoted into 10 sterile 50 mL polypropylene tubes and centrifuged. The supernatants were discarded, the pellets resuspended in 20 mL of 18% PEG 4,000 buffer, respectively, and all tubes were pooled into four 50 mL polypropylene tubes. The tubes were again centrifuged, the supernatants discarded, and after resuspension of the pellets in 20 mL 18% PEG 4,000 buffer, respectively, the crystal slurry was pooled into 2 tubes and centrifuged. Washing and centrifugation was performed once more, and after discarding the buffer, the concentration was adjusted to 50 mg/mL with fresh buffer. The concentration of an aliquot was determined by OD280 (10 µL in 1990 µL water).

A=0.345/0.358/0.356, c=51.5 mg/mL.

This slurry was filled into two sterile 15 mL polypropylene tubes, filling volumes 2 and 3 mL. The remaining slurry was concentrated to 200 mg/mL by centrifugation. The concentration of an aliquot was determined by OD280 (5 µL in 1995 µL water).

A=0.656/0.659/0.652, c=191.4 mg/mL.

This slurry was filled into sterile 2 mL Eppendorf reaction tubes.

| Composition | |
|---|---|
| MAK195F | 51.5/191.4 mg/mL |
| PEG 4,000 | 18% m/v |
| Pluronic F 68 | 0.1 mg/mL |
| sodium dihydrogen | 1.56 mg/mL |
| phosphate dihydrate sodium hydroxide | pH adjustment 7.2 |

3. Preparation of the "Process without Agitation" Sample, 31 Days after Batch Crystallization Start:
Buffer Preparation (Buffer MAK195F with PEG)

First, 50 mL of a 0.5 M phosphate stock solution were prepared. 3.9 g sodium dihydrogen phosphate dihydrate were dissolved in around 40 mL purified water, and the pH was brought to 7.2 with sodium hydroxide. The volume was adjusted to 50 mL.

360 g PEG 4,000, 40 mL of the stock solution and 0.2 g Pluronic F 68 were dissolved to 2000 mL with purified water.
Determination of Crystal Yield The concentration of the resulting MAK195F crystallization batch was determined by OD280. 150 µL aliquots were centrifuged at 14,000 rpm for 20 minutes. 100 µL of the supernatant were diluted with 1900 µL distilled water and measured against distilled water.

| Supernatant I: | A = 0.192 | |
|---|---|---|
| Supernatant II: | A = 0.193 | c = 2.8 mg/mL crystal yield 44% |

Concentration and Buffer Exchange/Filling

All centrifugation steps were performed at speeds of between 500 to 2,000 rpm in that way that pellets formed which were easily resuspendable, and no residual solid was found in the supernatant. The crystal slurry was aliquoted into 9 sterile 50 mL poly propylene tubes and centrifuged. The supernatants were discarded, the pellets resuspended in 20 mL of 18% PEG 4,000 buffer, respectively, and all tubes were pooled into four 50 mL polypropylene tubes. The tubes were again centrifuged, the supernatants discarded, and after resuspension of the pellets in 20 mL 18% PEG 4,000 buffer, respectively, the crystal slurry was pooled into 2 tubes and centrifuged. Washing and centrifugation was performed once more, and after discarding the buffer, the concentration was adjusted to 200 mg/mL with new buffer. The concentration of an aliquot was determined by OD280 (5 µL in 1995 µL water).

A=0.685/0.652/0.651, c=193.5 mg/mL

This slurry was filled into sterile 2 mL Eppendorf reaction tubes.

| Composition | |
|---|---|
| MAK195F | 193.5 mg/mL |
| PEG 4,000 | 18% m/v |
| Pluronic F 68 | 0.1 mg/mL |
| sodium dihydrogen | 1.56 mg/mL |
| phosphate dihydrate sodium hydroxide | pH adjustment 7.2 |

SE-HPLC Data

SE-HPLC analysis of the samples revealed that all four samples contained above 97.5% monomeric species.

Example 59

Orientating Study on Local Tolerance and Toxicity of MAK195F (Afelimomab) Crystals in Male Sprague-Dawley Rats Following Single Subcutaneous Administration 1. Experimental Data The objective of this study was to examine the local tolerability of MAK195F (afelimomab) an antibody against TNFα in new types of formulation. Further, additional information about systemic toxicity and toxicokinetic data of the formulations were investigated in this study. The local tolerability and toxicicological and pathological effects of MAK195F (afelimomab) were studied in male Sprague-Dawley rats (Charles River Laboratories, 69592 L'Arbresle, France) after a single subcutaneous injection of different formulations of MAK195F (afelimomab) followed by different observation periods (see Tables 6 and 7). The administered dose volume was 1 mL/kg body weight.

TABLE 6

| Experimental Groups | |
|---|---|
| Experimental Groups | |
| 01 | Control (vehicle) |
| 02 | 50 mg/ml Afelimomab, liquid, standard formulation |
| 03 | 50 mg/ml Afelimomab, crystals, process with agitation |
| 05 | 200 mg/ml Afelimomab, crystals, process with agitation |
| 06 | 200 mg/ml Afelimomab, crystals, process without agitation |
| Group A | Observation period 2 days |
| Group B | Observation period 7 days |
| Group C | Observation period 14 days |

TABLE 7

| Grouping and rat identification (N = 1 per group) | | | |
|---|---|---|---|
| | Animal number | | |
| Group | Group A | Group B | Group C |
| 01 | 1 | 2 | 3 |
| 02 | 4 | 5 | 6 |

TABLE 7-continued

Grouping and rat identification (N = 1 per group)

| Group | Animal number | | |
|---|---|---|---|
| | Group A | Group B | Group C |
| 03 | 7 | 8 | 9 |
| 05 | 13 | 14 | 15 |
| 06 | 16 | 17 | 18 |

The animals were observed for clinical signs and mortality on day 1 at 15 min, 1, 3, 5, and 24 h p.a. and at least once daily afterwards. Body weights were measured on the days of dosing (day 1) and necropsy (day 3, 15 or 21, respectively) and twice weekly, if applicable. Blood samples for drug analysis were collected on Day 1 (4 h p.a.), and on Days 2, 3, 5, 8, and 15 as applicable. Prior to necropsy blood was collected and hematological and clinical chemistry parameters were evaluated. Blood smears were prepared of each animal prior to necropsy. At necropsy, macroscopy of body cavities was performed. Organ weight measurement was performed on liver, kidneys, thymus, spleen, and lymph nodes. Preliminary histopathology was performed on the injection site and on liver, kidneys, thymus, spleen, and lymph nodes. All animals survived the study until scheduled necropsy. No test item-related effect on body weight was observed. Hematology and clinical chemistry values were highly variable. No clearly test item-related changes were identified in haematology or clinical chemistry. No test item-related changes were noted in urinalysis. Measurement of organ weights resulted in high variability and no clearly test item-related changes in organ weights. All other changes belonged to the spectrum of spontaneous findings commonly seen in Sprague-Dawley rats of this strain and age.

Microscopic Findings were:
- No findings in Groups 01, 02
- Slight to moderate diffuse subcutaneous inflammation in Groups 03 and 05
- Minimal to slight subcutaneous edema in Groups 03 (Days 8 and 15) and 05 (Day 3)
- No findings other than minimal mixed-cellular infiltrates (Day 15) in Group 06

Preliminary immunohistochemistry results of pan-T, suppressor/cytotoxic T cells/natural killer cells, pan-B cells and pan-macrophage markers on the local reactions indicate mainly macrophages and natural killer cells involved in the subcutaneous inflammations/infiltrations. Thus, there were no hints for a local immunogenic response to the formulations used. All other changes belonged to the spectrum of spontaneous findings commonly seen in Sprague-Dawley rats of this strain and age.

The absolute levels of Afelimomab in all samples tested were low. Large variability was observed between the samples, likely because of the limited sampling frequency and the low number of animals used. In most samples, no Afelimomab could be detected in serum after 5-8 days. A similar PK profile was observed for liquid and crystal formulations, and there was no impact of crystal process (with or without agitation) on PK profiles. The observed T1/2 for most samples were in the range of 1-2 days. Details are presented in Table 8.

TABLE 8

Plasma exposure levels of MAK195F

| | Time | Concentration (µg/ml) | | | Average | |
|---|---|---|---|---|---|---|
| | (day) | Rat 4 | Rat 5 | Rat 6 | (µg/ml) | STD |
| 50 mg/kg liquid standard formulation | 0.167 | 1.40 | 1.17 | 1.38 | 1.32 | 0.13 |
| | 2 | 0.76 | 0.97 | 0.66 | 0.80 | 0.16 |
| | 3 | 0.45 | 0.67 | 0.47 | 0.53 | 0.12 |
| | 5 | | LLOQ | LLOQ | LLOQ | |
| | 8 | | LLOQ | LLOQ | LLOQ | |
| | 15 | | | LLOQ | LLOQ | |

| | Time | Concentration (µg/ml) | | | Average | |
|---|---|---|---|---|---|---|
| | (day) | Rat 7 | Rat 8 | Rat 9 | (µg/ml) | STD |
| 50 mg/kg crystals, process with agitation | 0.167 | 0.26 | 0.84 | 0.45 | 0.52 | 0.30 |
| | 2 | 0.50 | 0.76 | 0.5 | 0.59 | 0.15 |
| | 3 | 0.43 | 0.55 | 0.46 | 0.48 | 0.06 |
| | 5 | | LLOQ | LLOQ | LLOQ | |
| | 8 | | LLOQ | LLOQ | LLOQ | |
| | 15 | | | LLOQ | LLOQ | |

| | Time | Concentration (µg/ml) | | | Average | |
|---|---|---|---|---|---|---|
| | (day) | Rat 13 | Rat 14 | Rat 15 | (µg/ml) | STD |
| 200 mg/kg crystals, process with agitation | 0.167 | 1.74 | 1.57 | 1.53 | 1.61 | 0.11 |
| | 2 | 1.31 | 1.54 | 1.5 | 1.45 | 0.12 |
| | 3 | 1.29 | 1.29 | 1.1 | 1.23 | 0.11 |
| | 5 | | 0.33 | 0.22 | 0.28 | 0.08 |
| | 8 | | LLOQ | LLOQ | LLOQ | |
| | 15 | | | LLOQ | LLOQ | |

| | Time | Concentration (µg/ml) | | | Average | |
|---|---|---|---|---|---|---|
| | (day) | Rat 16 | Rat 17 | Rat 18 | (µg/ml) | STD |
| 200 mg/kg crystals, process without agitation | 0.167 | 1.49 | 1.33 | 1.35 | 1.39 | 0.09 |
| | 2 | 1.29 | 1.37 | 1.38 | 1.35 | 0.05 |
| | 3 | 1.18 | 1.75 | 1.65 | 1.53 | 0.30 |
| | 5 | | 0.52 | 0.55 | 0.54 | 0.02 |
| | 8 | | LLOQ | LLOQ | LLOQ | |
| | 15 | | | LLOQ | LLOQ | |

LLOQ = below quantitation limit

Following subcutaneous administration of MAK195F (Afelimomab) in different formulations no mortality or test item-related clinical signs were observed. Macroscopically no local reaction to the test item formulations was noted. Hematology, clinical chemistry and organ weights resulted in highly variable values with no clear relationship to the test item. The severity of local inflammatory reaction at the administration site identified by macroscopic examination was higher for crystal formulations generated with agitation (smaller needles) of both concentrations than for the crystal formulation generated without agitation (larger needles) and the standard preparation.

INCORPORATION BY REFERENCE

The contents of all cited references (including literature references, patents, patent applications, and websites) that maybe cited throughout this application are hereby expressly incorporated by reference. The practice of the present invention will employ, unless otherwise indicated, conventional techniques of small and large scale protein crystallization and purification, which are well known in the art.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

We claim:

1. A batch crystallization method for the preparation of antibody crystals of a desired substantially uniform size range, the method comprising the steps of:
   a) providing an aqueous crystallization mixture having a pH of 4 to 6.5 comprising 0.5 mg/ml to 280 mg/ml of an anti-hTNFalpha antibody fragment, a polyalkylene polyol as a crystallization agent, and about 0.02 M to 0.5 M of a buffer under conditions that enable the formation of anti-hTNFalpha antibody fragment crystals, wherein the polyalkylene polyol is present in the crystallization mixture at a final concentration in the range of 5 to 30% (w/v) of the total volume; and
   b) agitating said crystallization mixture under controlled conditions, whereby said anti-hTNFalpha antibody fragment crystals having a needle-like morphology with a length of 2 to 500 μm and a length/diameter (l/d) ratio of 1 to 100 are formed,
   wherein said anti-hTNFalpha antibody fragment is MAK195F, which is a F(ab')$_2$ fragment of antibody MAK195 produced by a hybridoma cell line having the deposit number ECACC 87050801.

2. The method of claim 1, wherein said controlled conditions correspond to agitating said crystallization mixture in a roller container at a speed in a range of from 1 to 200 rpm.

3. The method of claim 2, wherein said controlled conditions correspond to agitating said crystallization mixture in a roller container having a diameter in a range of 2 to 100 cm.

4. The method of claim 2, wherein said controlled conditions correspond to agitating said crystallization mixture in a roller container wherein 1 to 100% of the total internal volume of said roller container is filled with the crystallization mixture.

5. The method of claim 3, wherein said controlled conditions correspond to agitating said crystallization mixture in a roller container wherein 1 to 100% of the total internal volume of said roller container is filled with the crystallization mixture.

6. The method of claim 1, wherein the crystallization agent is a polyalkylene glycol.

7. The method of claim 6, wherein the crystallization agent is polyethylene glycol.

8. The method of claim 1, wherein the MAK 195F is agitated in a roller container at a speed in a range of 5 to 100 rpm for 1 to 60 days at a temperature in a range of 15 to 25° C.

9. The method of claim 8, wherein said crystals comprise a controlled mean crystal particle length in a range of 1 to 200 μm.

10. The method of any one of claims 1 to 5, wherein said controlled conditions correspond to agitating said crystallization mixture in a roller container for 30 minutes to 20 days.

11. The method of any one of claims 1 to 5, wherein said controlled conditions correspond to agitating said crystallization mixture in a roller container at a temperature in a range of −15 to +50° C.

12. The method of any one of claims 1 to 5, wherein said agitating comprises rolling, stirring, shaking and/or tumbling said crystallization mixture.

13. A batch crystallization method for crystallizing an anti-hTNFalpha antibody fragment, the method comprising the steps of:
   a) providing an aqueous crystallization mixture comprising 0.5 mg/ml to 280 mg/ml of an anti-hTNFalpha antibody fragment, a polyalkylene glycol as a crystallization agent, and 0.02 M to 0.5 M of a buffer, wherein the aqueous crystallization mixture has a pH of 4 to 6.5 and wherein the polyalkylene glycol is present in the crystallization mixture at a final concentration in the range of 5 to 30% (w/v) of the total volume; and
   b) incubating said aqueous crystallization mixture until crystals of said anti-hTNFalpha antibody fragment are formed;
   wherein the polyalkylene glycol is provided either (a) in one step or (b) in more than one step, wherein said crystals formed in a step are not removed in subsequent steps, wherein crystallization is performed under crystal size controlled conditions, wherein the crystals have a needle morphology with a length of 2 to 500 μm and a (l/d) ratio of 1 to 100, and wherein said anti-hTNFalpha antibody fragment is MAK195F, a F(ab')$_2$ fragment of antibody MAK195 produced by a hybridoma cell line having the deposit number ECACC 87050801.

14. The method of claim 13, wherein said buffer comprises an acetate buffer and/or a citrate buffer.

15. The method of claim 13, wherein said buffer comprises sodium acetate and/or sodium citrate.

16. The method of claim 13, wherein the polyalkylene glycol has an average molecular weight in the range of 400 to 10,000 g/mol.

17. The method of claim 16, wherein the polyalkylene glycol is polyethylene glycol.

18. The method of claim 13, wherein the polyalkylene glycol is polyethylene glycol.

19. The method of claim 13, wherein said controlled conditions comprise agitating said crystallization mixture in a roller container at a speed in a range of from 1 to 200 rpm.

20. The method of claim 19, wherein said controlled conditions comprise agitating said crystallization mixture in a roller container wherein 1 to 100% of the total internal volume of said roller container is filled with the crystallization mixture.

21. The method of claim 13, wherein said controlled conditions comprise agitating said crystallization mixture in a roller container having a diameter in a range of 2 to 100 cm.

22. The method of claim 13, wherein said controlled conditions comprise agitating said crystallization mixture in a roller container wherein 1 to 100% of the total internal volume of said roller container is filled with the crystallization mixture.

23. The method of any one of claims 13 or 19 to 20, wherein said controlled conditions comprise agitating said crystallization mixture in a roller container for 30 minutes to 20 days.

24. The method of any one of claims 13 or 19 to 20, wherein said controlled conditions comprise agitating said crystallization mixture in a roller container at a temperature in a range of −15 to +50° C.

25. The method of any one of claims 13 or 19 to 20, wherein said agitating comprises rolling, stirring, shaking and/or tumbling said crystallization mixture.

26. The method of any one of claims 1-5 and 13, wherein at least one of the following additional crystallization conditions are met:
   a) incubation is performed for 1 hour to 250 days; and
   b) incubation is performed at a temperature between −15° C. and +50° C.

27. The method of claim 26, further comprising the step of drying said crystals.

28. The method of claim 26, wherein the crystallization mixture comprises crystals and a natural mother liquor, and wherein the method further comprises the step of exchanging the natural mother liquor with an artificial mother liquor.

29. The method of any one claims 1-5 and 13, further comprising the step of drying said crystals.

30. The method of any one of claims 1-5, and 13, wherein the crystallization mixture comprises a batch volume in the range of 1 ml to 20,000 liters.

31. Antibody crystals obtained by the method of any one of claims 1 to 5.

32. A composition comprising a crystal of an anti-hTNFalpha antibody fragment, a polyalkylene polyol, and a buffer, wherein said crystal has a needle morphology with a length of 2 to 500 µm and a length/diameter (l/d) ratio of 1 to 100, and wherein the anti-hTNFalpha antibody fragment is MAK195F, which is a F(ab')$_2$ fragment of antibody MAK195 produced by a hybridoma cell line having the deposit number ECACC 87050801.

33. An injectable liquid composition comprising the composition of claim 32, wherein the antibody fragment is present at a concentration in a range of 10 to 400 mg/ml.

34. A crystal slurry composition comprising the composition of claim 32, wherein the antibody fragment is present in a concentration greater than 100 mg/ml.

35. A pharmaceutical composition comprising: (a) the composition according to claim 32, and (b) at least one pharmaceutical excipient.

36. The pharmaceutical composition of claim 35, wherein said antibody fragment is present in a concentration greater than 200 mg/ml.

37. The pharmaceutical composition of claim 35, wherein said pharmaceutical formulation is provided as a solid, a semisolid, or a liquid formulation.

38. A pharmaceutical composition comprising the composition according to claim 32, wherein the bioavailability and safety of the crystals is not decreased relative to a liquid composition of the hTNF antibody fragment.

39. The composition of claim 32, wherein the crystal is obtained by a batch crystallization method comprising the steps of a) providing an aqueous crystallization mixture having a pH of 4 to 6.5 comprising 0.5 mg/ml to 280 mg/ml of the anti-hTNFalpha antibody fragment, and a polyalkylene polyol as a crystallization agent, and 0.02 M to 0.5 M of a buffer under conditions that enable the formation of the antibody fragment crystals; and b) agitating said crystallization mixture under controlled conditions, whereby antibody crystals having a needle-like morphology with a length of 2 to 500 µm and a length/diameter (l/d) ratio of 1 to 100 are formed.

40. The composition of claim 39, wherein said controlled conditions correspond to agitating said crystallization mixture in a roller container at a speed in a range of from 1 to 200 rpm.

41. The composition of claim 39 or 40, wherein said controlled conditions correspond to agitating said crystallization mixture in a roller container for 30 minutes to 20 days.

42. The composition of claim 39 or 40, wherein said controlled conditions correspond to agitating said crystallization mixture in a roller container at a temperature in a range of −15 to +50° C.

43. A composition comprising a crystal of an anti-hTNFalpha antibody fragment, wherein the crystal is obtained by the method of any one of claims 1 to 5, 13, and 19 to 20, wherein said anti-hTNFalpha antibody fragment is MAK195F, which is a F(ab')$_2$ fragment of antibody MAK195 produced by a hybridoma cell line having the deposit number ECACC 87050801.

44. A pharmaceutical composition comprising: (a) the composition according to claim 32, and (b) at least one pharmaceutical excipient, wherein the excipient embeds or encapsulates said crystals.

45. The pharmaceutical composition of claim 44, wherein said antibody fragment is present in a concentration greater than 1 mg/ml.

46. The pharmaceutical composition of claim 35, wherein said antibody fragment is present in a concentration greater than 1 mg/ml.

47. The pharmaceutical composition of claim 44, wherein said antibody fragment is present in a concentration greater than 200 mg/ml.

48. The pharmaceutical composition of claim 35 or 44, wherein said composition is a solid comprising 0.1 to 99.9% (w/w) of the MAK195F antibody crystals.

49. The pharmaceutical composition of claim 35 or 44, wherein said excipient comprises at least one polymeric biodegradable or nonbiodegradable carrier and/or at least one oil or lipid carrier.

50. The pharmaceutical composition according to claim 49, wherein said biodegradable or nonbiodegradable carrier comprises at least one polymer selected from the group consisting of poly (acrylic acid), poly (cyanoacrylates), poly (amino acids), poly (anhydrides), poly (depsipeptide), poly (esters), poly (lactic acid), poly (lactic-co-glycolic acid) or PLGA, poly (β-hydroxybutryate), poly (caprolactone), poly (dioxanone); poly (ethylene glycol), poly (hydroxypropyl) methacrylamide, poly[(organo) phosphazene, poly (ortho esters), poly (vinyl alcohol), poly (vinylpyrrolidone), maleic anhydride alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

51. A method for treating a mammal, the method comprising the step of administering to the mammal an effective amount of the antibody crystals obtained by the method of any one of claims 1 to 5, 13, and 19 to 20, wherein said anti-hTNFalpha antibody fragment is MAK195F, a F(ab')$_2$ fragment of antibody MAK195 produced by a hybridoma cell line having the deposit number ECACC 87050801.

52. A method for treating a mammal, the method comprising the step of administering to the mammal an effective amount of the composition of claim 35.

53. A method for treating a mammal, the method comprising the step of administering to the mammal an effective amount of the composition of claim 44.

54. The method of claim 52 or 53, wherein the composition is administered by parenteral route, oral route, or by injection.

55. A method of treating a hTNFalpha-related disorder in a subject, the method comprising the step of administering a therapeutically effective amount of the MAK195F antibody crystals of claim 31.

56. The method of claim 55, wherein said hTNFalpha-related disorder is selected from the group consisting of an autoimmune disease, in particular rheumatoid arthritis, rheumatoid spondylitis, osteoarthritis and gouty arthritis, an allergy, multiple sclerosis, autoimmune diabetes, autoimmune uveitis and nephrotic syndrome; an infectious disease, transplant rejection or graft-versus-host disease, malignancy, pulmonary disorder, intestinal disorder, cardiac disorder, inflammatory bone disorders, bone resorption disease, alcoholic hepatitis, viral hepatitis, fulminant hepatitis, coagulation disturbances, burns, reperfusion injury, keloid formation, scar tissue formation, pyrexia, periodontal disease, obesity and radiation toxicity; a spondyloarthropathy, a pulmonary disorder, a coronary disorder, a metabolic disorder, anemia, pain, a hepatic disorder, a skin disorder, a nail disorder, or vasculitis, Behcet's disease, ankylosing spondylitis, asthma, chronic obstructive pulmonary disease (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriasis, psoriatic arthritis, and chronic plaque psoriasis, age-related cachexia, Alzheimer's disease, brain edema, inflammatory brain injury, chronic fatigue syndrome, dermatomyositis, drug reactions, edema in and/or around the spinal cord, familial periodic fevers, Felty's syndrome, fibrosis, glomerulonephritides (e.g. post-streptococcal glomerulonephritis or IgA nephropathy), loosening of prostheses, microscopic polyangiitis, mixed connective tissue disorder, multiple myeloma, cancer and cachexia, multiple organ disorder, myelo dysplastic syndrome, orchitism osteolysis, pancreatitis, including acute, chronic, and pancreatic abscess, periodontal disease polymyositis, progressive renal failure, pseudogout, pyoderma gangrenosum, relapsing polychondritis, rheumatic heart disease, sarcoidosis, sclerosing cholangitis, stroke, thoracoabdominal aortic aneurysm repair (TAAA), TNF receptor associated periodic syndrome (TRAPS), symptoms related to Yellow Fever vaccination, inflammatory diseases associated with the ear, chronic ear inflammation, or pediatric ear inflammation, uveitis, sciatica, prostatitis, endometriosis, choroidal neovascularization, lupus, Sjogren's syndrome, and wet macular degeneration.

57. The method of claim 55, wherein said hTNFalpha-related disorder is selected from the group consisting of an Acquired Immunodeficiency Disease Syndrome, Acquired Immunodeficiency Related Diseases, Acquired pernicious anaemia, Acute coronary syndromes, Acute and chronic pain, Acute Idiopathic Polyneuritis, Acute immune disease associated with organ transplantation, Acute or chronic immune disease associated with organ transplantation, Acute Inflammatory Demyelinating Polyradiculoneuropathy, Acute ischemia, Acute liver disease, Acute rheumatic fever, Acute transverse myelitis, Addison's disease, Adult (acute) respiratory distress syndrome, Adult Still's Disease, Alcoholic cirrhosis, Alcohol-induced liver injury, Allergic diseases, Allergy, Alopecia, Alopecia greata, Alzheimer's disease, Anaphylaxis, Ankylosing spondylitis, Ankylosing spondylitis associated lung disease, Anti-Phospholipid Antibody Syndrome, Aplastic anemia, Arteriosclerosis, Arthropathy, Asthma, Atheromatous disease/arteriosclerosis, Atherosclerosis, Atopic allergy, Atopic eczema, Atopic dermatitis, Atrophic autoimmune hypothyroidism, Autoimmune bullous disease, Autoimmune dermatitis, Autoimmune diabetes, Autoimmune disorder associated with *Streptococcus* infection, Autoimmune Enteropathy, Autoimmune haemolytic anaemia, Autoimmune hepatitis, Autoimmune hearingloss, Autoimmune Lymphoproliferative Syndrome (ALPS), Autoimmune mediated hypoglycaemia, Autoimmune myocarditis, Autoimmune neutropenia, Autoimmune premature ovarian failure, Autoimmune thrombocytopenia (AITP), Autoimmune thyroid disease, Autoimmune uveitis, Bronchiolitis obliterans, Behcet's disease, Blepharitis, Bronchiectasis, Bullous pemphigoid, Cachexia, Cardiovascular Disease, Catastrophic Antiphospholipid Syndrome, Celiac Disease, Cervical Spondylosis, *Chlamydia*, Choleosatatis, Chronic active hepatitis, Chronic eosinophilic pneumonia, Chronic fatigue syndrome, Chronic immune disease associated with organ transplantation, Chronic ischemia, Chronic liver diseases, Chronic mucocutaneous candidiasis, Cicatricial pemphigoid, Clinically isolated Syndrome (CIS) with Risk for Multiple Sclerosis, Common varied immunodeficiency, common variable hypogammaglobulinaemia, Connective tissue disease associated interstitial lung disease, Conjunctivitis, Coombs positive haemolytic anaemia, Childhood Onset Psychiatric Disorder, Chronic obstructive pulmonary disease (COPD), Crohn's disease, Cryptogenic autoimmune hepatitis, Cryptogenic fibrosing alveolitis, Dacryocystitis, Depression, Dermatitis scleroderma, Dermatomyositis, Dermatomyositis/polymyositis associated lung disease, Diabetic retinopathy, Diabetes mellitus, Dilated cardiomyopathy, Discoid lupus erythematosus, Disk herniation, Disk prolaps, Disseminated intravascular coagulation, Drug-induced hepatitis, Drug-induced interstitial lung disease, Drug induced immune hemolytic anemia, Endocarditis, Endometriosis, Endophthalmitis, Enteropathic synovitis, Episcleritis, Erythema multiforme, Erythema multiforme major, Female infertility, Fibrosis, Fibrotic lung disease, Gestational pemphigoid, Giant cell arteritis (GCA), Glomerulonephritides, Goitrous autoimmune hypothyroidism (Hashimoto's disease), Goodpasture's syndrome, Gouty arthritis, Graft versus host disease (GVHD), Grave's disease, Group B streptococci (GBS) infection, Guillain-Barre Syndrome (GBS), haemosiderosis associated lung disease, Hay Fever, Heart failure, Hemolytic anemia, Henoch-Schoenlein purpurea, Hepatitis B, Hepatitis C, Hughes Syndrome, Huntington's chorea, Hyperthyroidism, Hypoparathyroidism, Idiopathic leucopaenia, Idiopathic hrombocytopaenia, Idiopathic Parkinson's Disease, Idiopathic interstitial pneumonia, Idiosyncratic liver disease, IgE-mediated Allergy, Immune hemolytic anemia, Inclusion Body Myositis, Infectious diseases, Infectious ocular inflammatory disease, Inflammatory bowel disease, Inflammatory demyelinating disease, Inflammatory heart disease, Inflammatory kidney disease, Insulin dependent diabetes mellitus, Interstitial pneumonitis, IPF/UIP, Iritis, Juvenile chronic arthritis, Juvenile pernicious anaemia, Juvenile rheumatoid arthritis, Kawasaki's disease, Keratitis, Keratojuntivitis sicca, Kussmaul disease or Kussmaul-Meier Disease, Landry's Paralysis, Langerhan's Cell Histiocytosis, Linear IgA disease, Livedo reticularis, Lyme arthritis, Lymphocytic infiltrative lung disease, Macular Degeneration, Male infertility idiopathic or NOS, Malignancies, Microscopic vasculitis of the kidneys, Microscopic Polyangiitis, Mixed connective tissue disease associated lung disease, Morbus Bechterev, Motor Neuron Disorders, Mucous membrane pemphigoid, Multiple sclerosis (all subtypes: primary progressive, secondary progressive, relapsing remitting etc.), Multiple Organ failure, Myalgic encephalitis/Royal Free Disease, Myasthenia Gravis, Myelodysplastic Syndrome, Myocardial infarction, Myocarditis, Nephrotic syndrome, Nerve Root Disorders, Neuropathy, Non-alcoholic Steatohepatitis, Non-A Non-B Hepatitis, Optic Neuritis, Organ transplant rejection, Osteoarthritis, Osteolysis, Ovarian cancer, Ovarian failure, Pancreatitis, Parasitic diseases, Parkinson's disease, Pauciarticular JRA, Pemphigoid, Pemphigus foliaceus, Pemphigus vulgaris, Peripheral artery occlusive disease (PAOD), Peripheral vascular disease (PVD), Peripheral artery disease (PAD), Phacogenic uveitis, Phlebitis, Polyarteritis nodosa (or periarteritis nodosa), Polychondritis, Polymyalgia Rheumatica, Poliosis, Polyarticular JRA, Polyendocrine Deficiency Syndrome, Polymyositis, Polyglandular deficiency type I and polyglandular deficiency type II, polymyalgia rheumatica (PMR), Postinfectious interstitial lung disease, Post-inflammatory interstitial lung disease, Post-Pump Syndrome, Premature ovarian failure, Primary biliary cirrhosis, Primary myxoedema, Primary parkinsonism, Primary sclerosing cholangitis, Primary sclerosing hepatitis, Primary vasculitis, Prostate and rectal cancer and hematopoietic malignancies (leukemia and lymphoma), Prostatitis, Psoriasis, Psoriasis type 1, Psoriasis type 2, Psoriatic arthritis, Psoriatic arthropathy, Pulmonary hypertension secondary to connective tissue disease, Pulmonary manifestation of polyarteritis nodosa, Pure red cell aplasia, Primary Adrenal Insufficiency, Radiation fibrosis, Reactive arthritis, Reiter's disease, Recurrent Neuromyelitis Optica, Renal disease NOS, Restenosis, Rheumatoid arthritis, Rheumatoid arthritis associated interstitial lung disease, Rheumatic heart disease, SAPHO (synovitis, acne, pustulosis, hyperostosis, and osteitis), Sarcoidosis, Schizophrenia, Schmidt's syndrome, *Scleroderma*, Secondary Amyloidosis, Shock lung, Scleritis, Sciatica, Secondary Adrenal Insufficiency, Sepsis syndrome, Septic arthritis, Septic shock, Seronegative arthopathy, Silicone associated connective tissue disease, Sjogren's disease associated lung disease, Sjorgren's syndrome, Sneddon-Wilkinson Dermatosis, Sperm autoimmunity, Spondyloarthropathy, Spondilitis ankylosans, Stevens-Johnson Syndrome (SJS), Still's disease, Stroke, Sympathetic ophthalmia, Systemic inflammatory response syndrome, Systemic lupus erythematosus, Systemic lupus erythematosus associated lung disease, Systemic sclerosis, Systemic sclerosis associated interstitial lung disease, Takayasu's disease/arteritis, Temporal arteritis, Th2 Type and Th1 Type mediated diseases, Thyroiditis, Toxic shock syndrome, Toxoplasmic retinitis, toxic epidermal necrolysis, Transverse myelitis, TRAPS (Tumor Necrosis Factor Receptor), Type B insulin resistance with acanthosis nigricans, Type 1 allergic reaction, Type-1 autoimmune hepatitis (classical autoimmune or lupoid hepatitis), Type-2 autoimmune hepatitis (anti-LKM antibody hepatitis), Type II Diabetes, Ulcerative colitic arthropathy, Ulcerative colitis, Urticaria, Usual interstitial pneumonia (UIP), Uveitis, Vasculitic diffuse lung disease, Vasculitis, Vernal conjunctivitis, Viral retinitis, Vitiligo, Vogt-Koyanagi-Harada syndrome (VKH syndrome), Wegener's granulomatosis, Wet macular degeneration, Wound healing, and *Yersinia* and salmonella associated arthropathy.

* * * * *